United States Patent [19]

Corvi

[11] Patent Number: 5,879,499

[45] Date of Patent: Mar. 9, 1999

[54] METHOD OF MANUFACTURE OF A MULTI-LUMEN CATHETER

[75] Inventor: Timothy J. Corvi, Belmont, Calif.

[73] Assignee: Heartport, Inc., Redwood City, Calif.

[21] Appl. No.: 664,716

[22] Filed: Jun. 17, 1996

[51] Int. Cl.[6] .......................... A61M 25/10; A61M 25/16
[52] U.S. Cl. ........................... 156/175; 156/86; 156/173; 156/294; 604/96; 604/282
[58] Field of Search ...................... 604/282, 96; 156/173, 156/175, 166, 172, 86, 85, 293, 294

[56] References Cited

U.S. PATENT DOCUMENTS

| | | |
|---|---|---|
| 243,396 | 6/1881 | Pfarre . |
| 3,416,531 | 12/1968 | Edwards . |
| 3,671,979 | 6/1972 | Moulopoulos . |
| 3,769,960 | 11/1973 | Robinson . |
| 4,000,739 | 1/1977 | Stevens . |
| 4,056,854 | 11/1977 | Boretos et al. . |
| 4,122,858 | 10/1978 | Schiff . |
| 4,173,981 | 11/1979 | Mortensen et al. . |

(List continued on next page.)

FOREIGN PATENT DOCUMENTS

| | | |
|---|---|---|
| 0 218 275 | 4/1987 | European Pat. Off. . |
| 0 350 302 | 7/1989 | European Pat. Off. . |
| 0 414 350 | 6/1990 | European Pat. Off. . |
| WO 91/01689 | 2/1991 | WIPO . |
| WO 91/08791 | 6/1991 | WIPO . |
| WO 91/17720 | 11/1991 | WIPO . |
| WO 92/17118 | 10/1992 | WIPO . |
| WO 95/05860 | 2/1995 | WIPO . |

OTHER PUBLICATIONS

Andersen et al., "Transluminal implantation of artificial heart valves," *European Heart Journal,* 1992;13:704–708.
Buckberg, "Strategies and logic of cardioplegic delivery to prevent, avoid, and reverse ischemic and reperfusion damage," *J Thorac Cardio Vasc Surg,* 1987;93:127–129.
Cosgrove, "Management of calcified aorta: An alternative method of occlusion," *Ann Thorac Surg,* 1983;36:718–719.
Crooke et al., "Biventricular distribution of cold blood cardioplegic solution administered by different retorgrade techniques," *J Card Thorac Surg.* 1991;102(4):631–636.
Erath et al., "Balloon catheter occlusion of the acsending aorta," *Ann Thorac Surg,* 1983;35:560–561.
Foster et al., "Proximal control of arota with a balloon catheter," *Surg. Gynecology & Obstetrics,* 1971:693–694.
Gundry et al., "A comparison of retrograde of cardioplegia versus antegrade cardioplegia in the presence of coronary artery obstruction," *Ann Thorac Surg,* 1984;38(2):124–127.
Ishizaka, "Myocardial protection by retrograde cardiac perfusion with cold modified Krebs solution through coronary sinus complete ischemic arrest for 120 minutes," *J Jpn Assn Thorac Surg,* 1977;25(12):1592–1601.
Lust et al., "Improved protection of chronically inflow–limited myocardium with retrograde coronary sinus cardioplegia," *Circulation III,* 1988;78(5):217–233.
"Occlusion Balloon Catheter: Instructions for Use," Meditech Boston Scientific Corporation Rev. Mar. 1991.
Ogawa, "Aortic arch reconstruction without aortic cross-–clamping using separate extracorporeal circulation," *J Jpn Assn Thorac Surg,* 1993;2185–2190.

(List continued on next page.)

*Primary Examiner*—Jeff H. Aftergut
*Attorney, Agent, or Firm*—Jens E. Hoekendijk; Jeffry J. Grainger

[57] ABSTRACT

A process for forming a multi-lumen catheter which includes the steps of providing a multi-lumen first tube, winding a flexible filament onto the first multi-lumen tube, and positioning a second tube over the wound filament layer of the first tube is disclosed for manufacturing the multi-lumen catheter. The second tube is melted and bonded to the first tube and an occluding member is mounted onto the second tube to occlude a patient's ascending aorta when the occluding member is expanded.

4 Claims, 58 Drawing Sheets

U.S. PATENT DOCUMENTS

| | | |
|---|---|---|
| 4,276,874 | 7/1981 | Wolvek et al. . |
| 4,287,892 | 9/1981 | Schiff . |
| 4,302,261 | 11/1981 | Simkins . |
| 4,343,672 | 8/1982 | Kanao . |
| 4,527,549 | 7/1985 | Gabbay . |
| 4,531,936 | 7/1985 | Gordon . |
| 4,540,399 | 9/1985 | Litzie et al. . |
| 4,577,543 | 3/1986 | Wilson . |
| 4,592,340 | 6/1986 | Boyles . |
| 4,601,713 | 7/1986 | Fuqua . |
| 4,664,125 | 5/1987 | Pinto . |
| 4,665,604 | 5/1987 | Dubowik . |
| 4,697,574 | 10/1987 | Karcher et al. . |
| 4,705,507 | 11/1987 | Boyles . |
| 4,741,328 | 5/1988 | Gabbay . |
| 4,764,324 | 8/1988 | Burnham . |
| 4,785,795 | 11/1988 | Singh . |
| 4,804,365 | 2/1989 | Litzie et al. . |
| 4,842,590 | 6/1989 | Tanabe et al. . |
| 4,877,035 | 10/1989 | Bogen et al. . |
| 4,889,137 | 12/1989 | Kolobow . |
| 4,899,787 | 2/1990 | Ouchi et al. . |
| 4,902,272 | 2/1990 | Milder et al. . |
| 4,902,273 | 2/1990 | Choy et al. . |
| 4,943,275 | 7/1990 | Stricker . |
| 4,944,729 | 7/1990 | Buckberg et al. . |
| 5,011,469 | 4/1991 | Buckberg et al. . |
| 5,015,232 | 5/1991 | Maglinte . |
| 5,024,668 | 6/1991 | Peters et al. . |
| 5,061,257 | 10/1991 | Martinez et al. . |
| 5,069,661 | 12/1991 | Trudell . |
| 5,116,305 | 5/1992 | Milder et al. . |
| 5,163,905 | 11/1992 | Michael . |
| 5,167,628 | 12/1992 | Boyles . |
| 5,171,218 | 12/1992 | Fonger et al. . |
| 5,176,619 | 1/1993 | Segalowitz . |
| 5,176,660 | 1/1993 | Truckai . |
| 5,186,713 | 2/1993 | Raible . |
| 5,190,520 | 3/1993 | Fenton, Jr. et al. . |
| 5,195,942 | 3/1993 | Weil et al. . |
| 5,219,326 | 6/1993 | Hattler . |
| 5,250,038 | 10/1993 | Melker et al. . |
| 5,254,097 | 10/1993 | Schock et al. . |
| 5,270,005 | 12/1993 | Raible . |
| 5,290,230 | 3/1994 | Ainsworth et al. . |
| 5,300,025 | 4/1994 | Wantink . |
| 5,304,132 | 4/1994 | Jang . |
| 5,308,320 | 5/1994 | Safar et al. . |
| 5,312,344 | 5/1994 | Grinfeld et al. . |
| 5,322,509 | 6/1994 | Rickerd . |
| 5,330,433 | 7/1994 | Fonger et al. . |
| 5,334,142 | 8/1994 | Paradis . |
| 5,334,169 | 8/1994 | Brown et al. . |
| 5,374,245 | 12/1994 | Mahurkar . |
| 5,421,825 | 6/1995 | Farcot . |
| 5,423,745 | 6/1995 | Todd et al. . |
| 5,429,597 | 7/1995 | DeMello et al. . |
| 5,433,700 | 7/1995 | Peters . |
| 5,451,207 | 9/1995 | Yock . |
| 5,464,394 | 11/1995 | Miller et al. . |
| 5,472,435 | 12/1995 | Sutton . |
| 5,478,309 | 12/1995 | Sweezer et al. . |
| 5,538,513 | 7/1996 | Okajima . |
| 5,549,557 | 8/1996 | Steinke et al. . |
| 5,591,142 | 1/1997 | Van Erp . |
| 5,697,905 | 12/1997 | d'Ambrosio . |
| 5,702,373 | 12/1997 | Samson . |

OTHER PUBLICATIONS

Okita et al. "Utilization of triple–lumen balloon catheter for occlusion of the ascending aorta during distal aortic arch surgery with hypothermic retrograde cerebral circulation technique through left thoracotomy," *J Card Surg*, 1995;10:699–702.

Peters, "The promise of cardioscopic surgery," *Austra/As J Card Thorac Surg*, 1993;2(3):152–154.

Razi, "The challenge of calcific aortitis," *J Card Thorac Surg*, 1993;8:102–107.

Rossi, "Long–term cardiopulmonary bypass by peripheral cannulation in a model of total heart failure," *J Thorac Card Vasc Surg*, 1990;100:914–921.

Sabiston, *Textbook of Surgery*, $10^{th}$ Ed. 1972, pp. 2021–2023,2114–2121.

Sakaguchi et al., "Aortic valve replacement and coronary artery bypass," *J Jpn Assn Thorc Surg*, 1993;41(6):1063–1068.

Takahashi, Retrograde coronary sinus perfusion for myocardial protection in aortic valve surgery, *J Jpn Assn Thorac Surg*, 1982;30(3):306–318.

Uchida et al., "Percutaneous cardiomyotomy and valvulotomy with angioscopic guidance," *Am Heart J*, 1991;121(4, part 1):1221–1224.

Uchida et al., "Percutaneous fiberoptic antioscopy of the cardiac valves," *Am Heart J*, 1991;121(6 part 1):1791–1798.

Yamaguchi, "A case of reoperation using a balloon catheter with blocked pars ascendes aortae," *Kyogu Geka*, 1991;42(11):961–964.

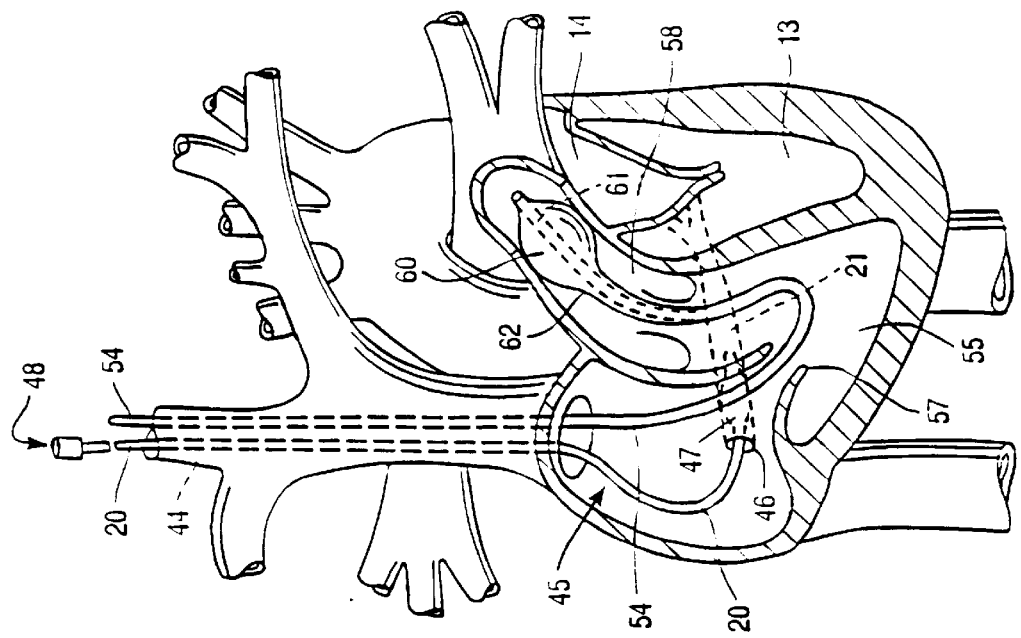
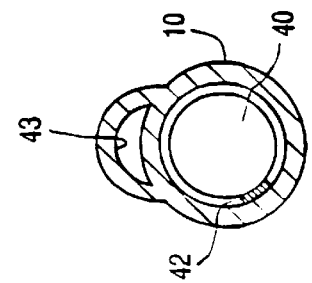
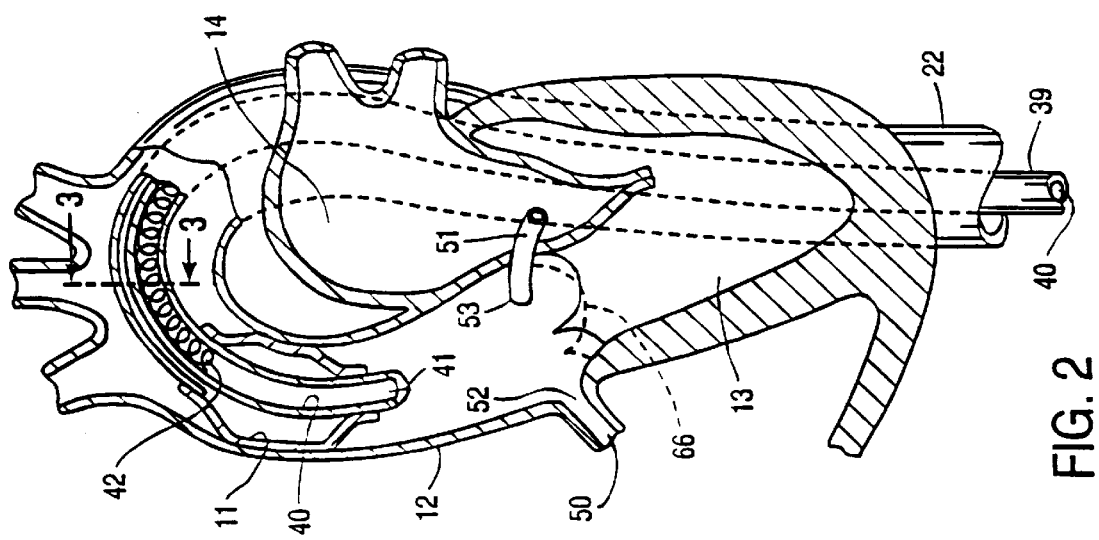

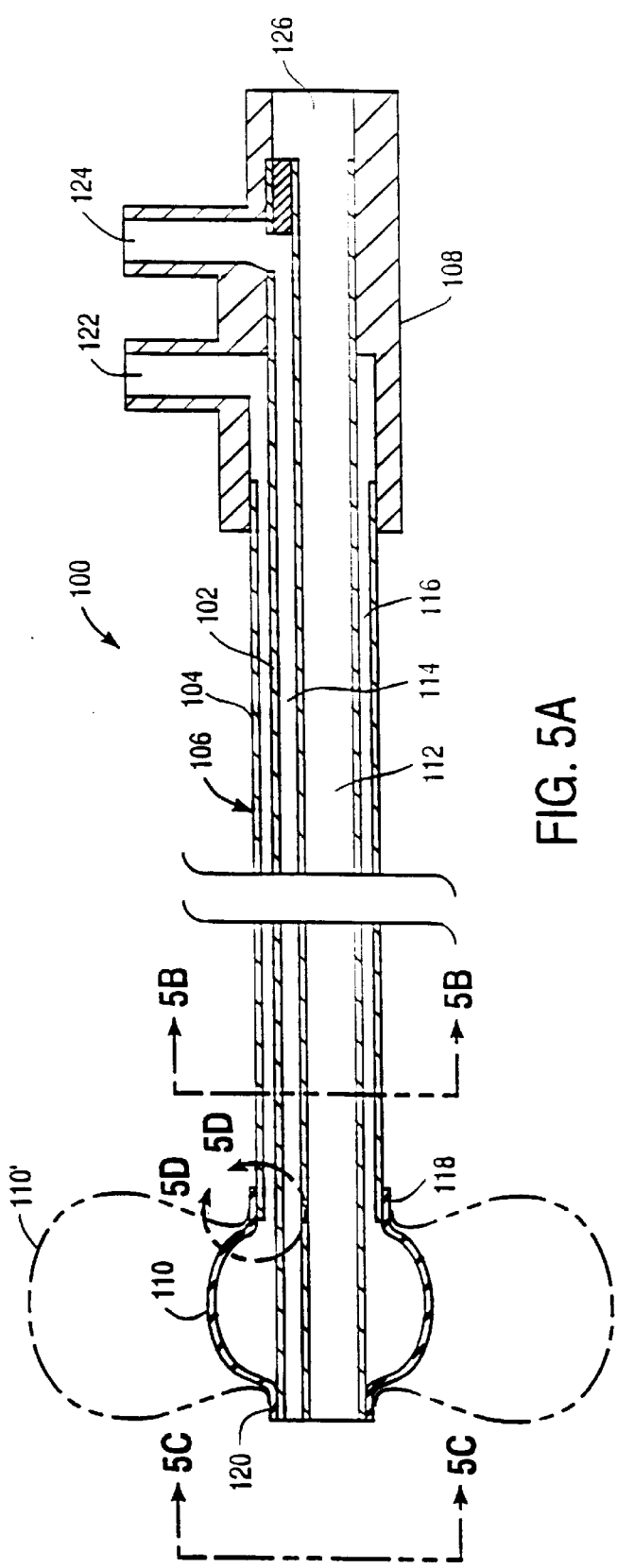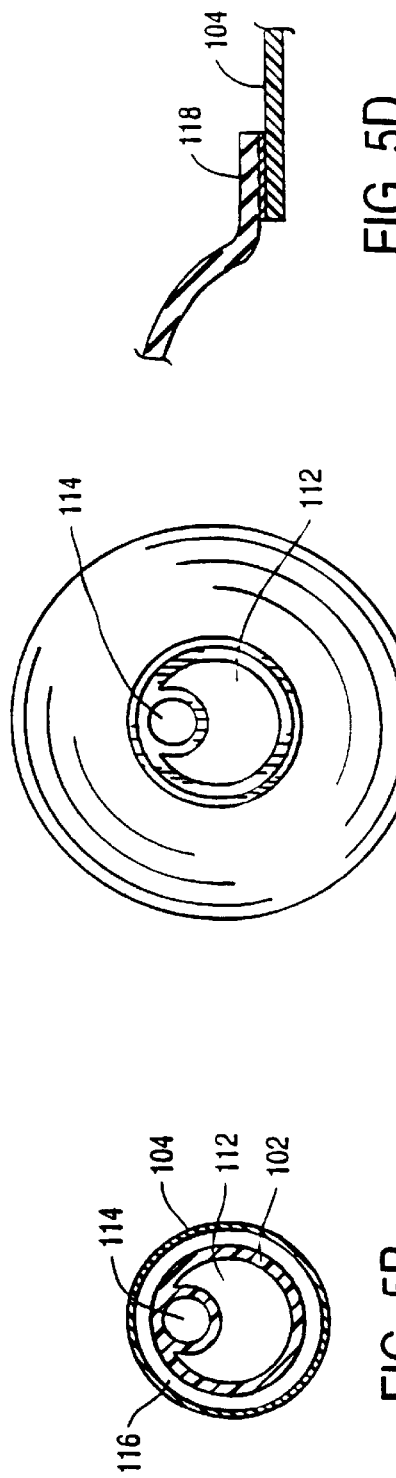

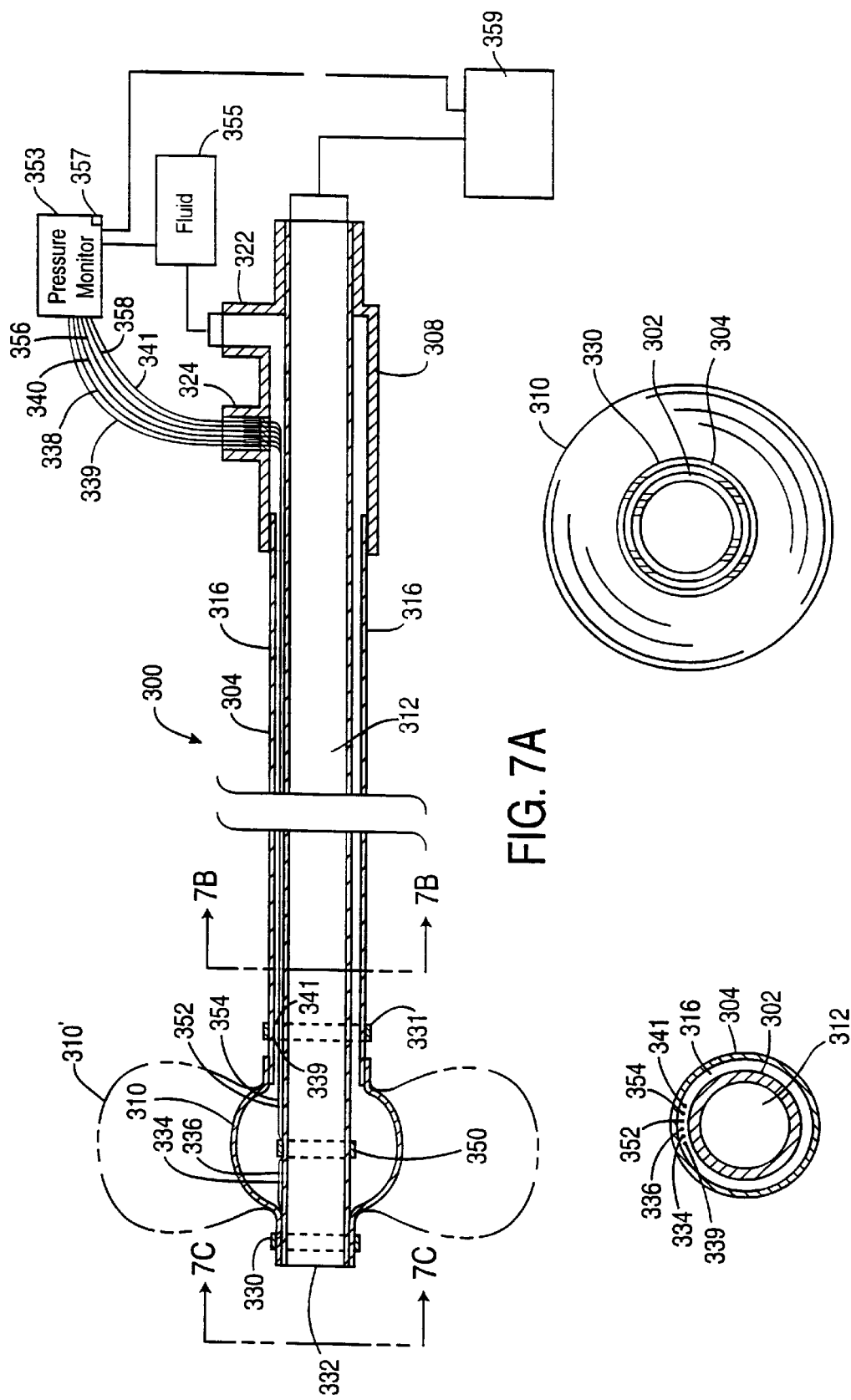

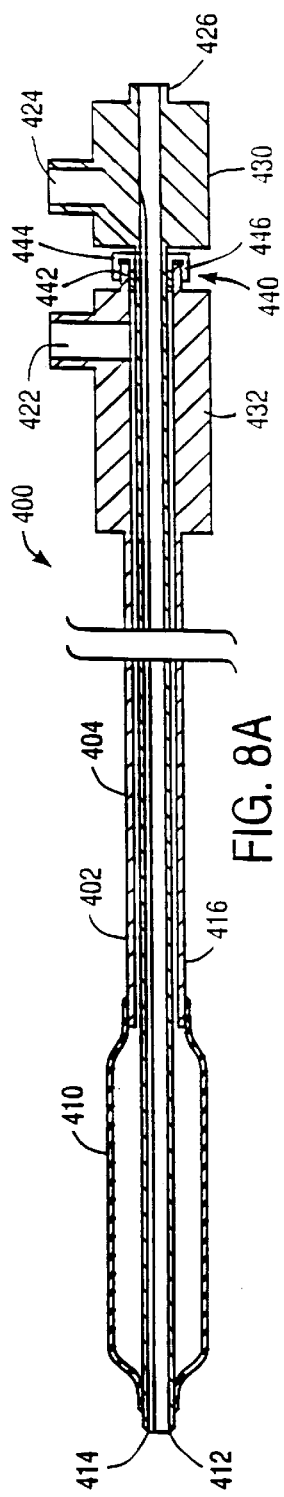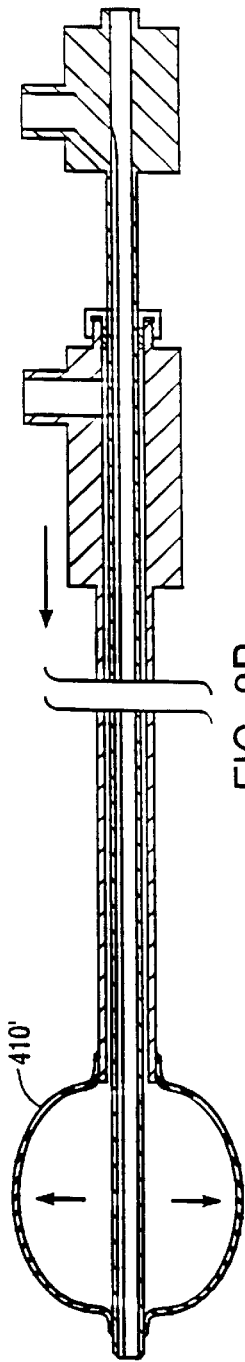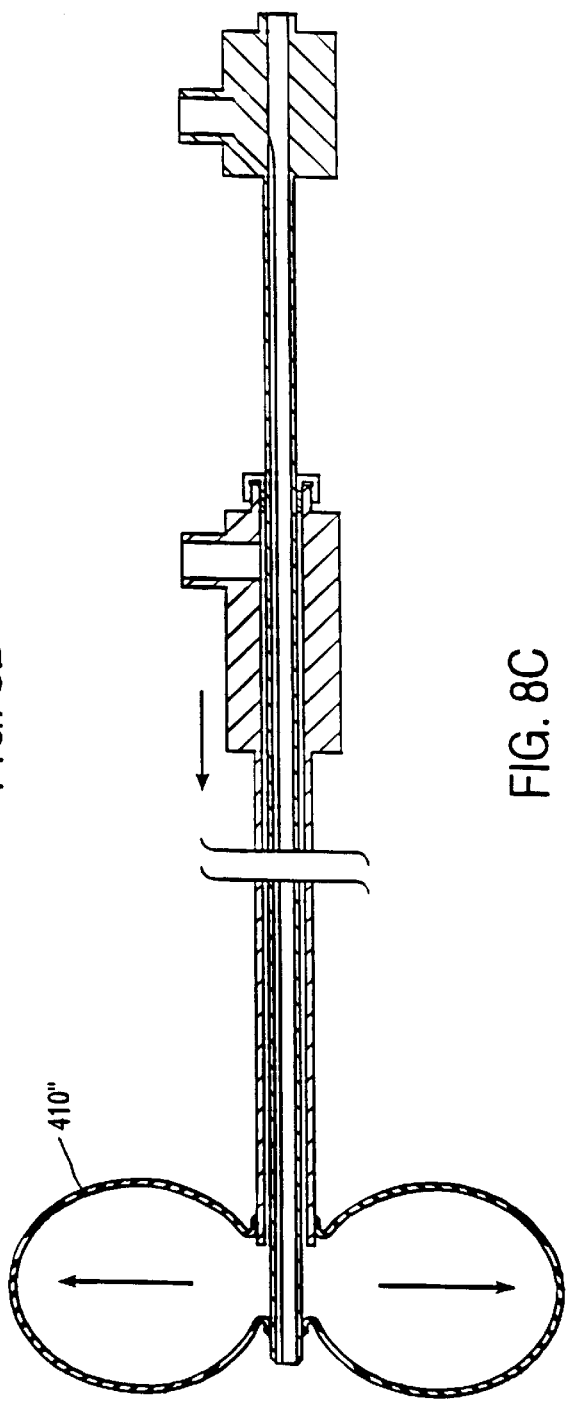

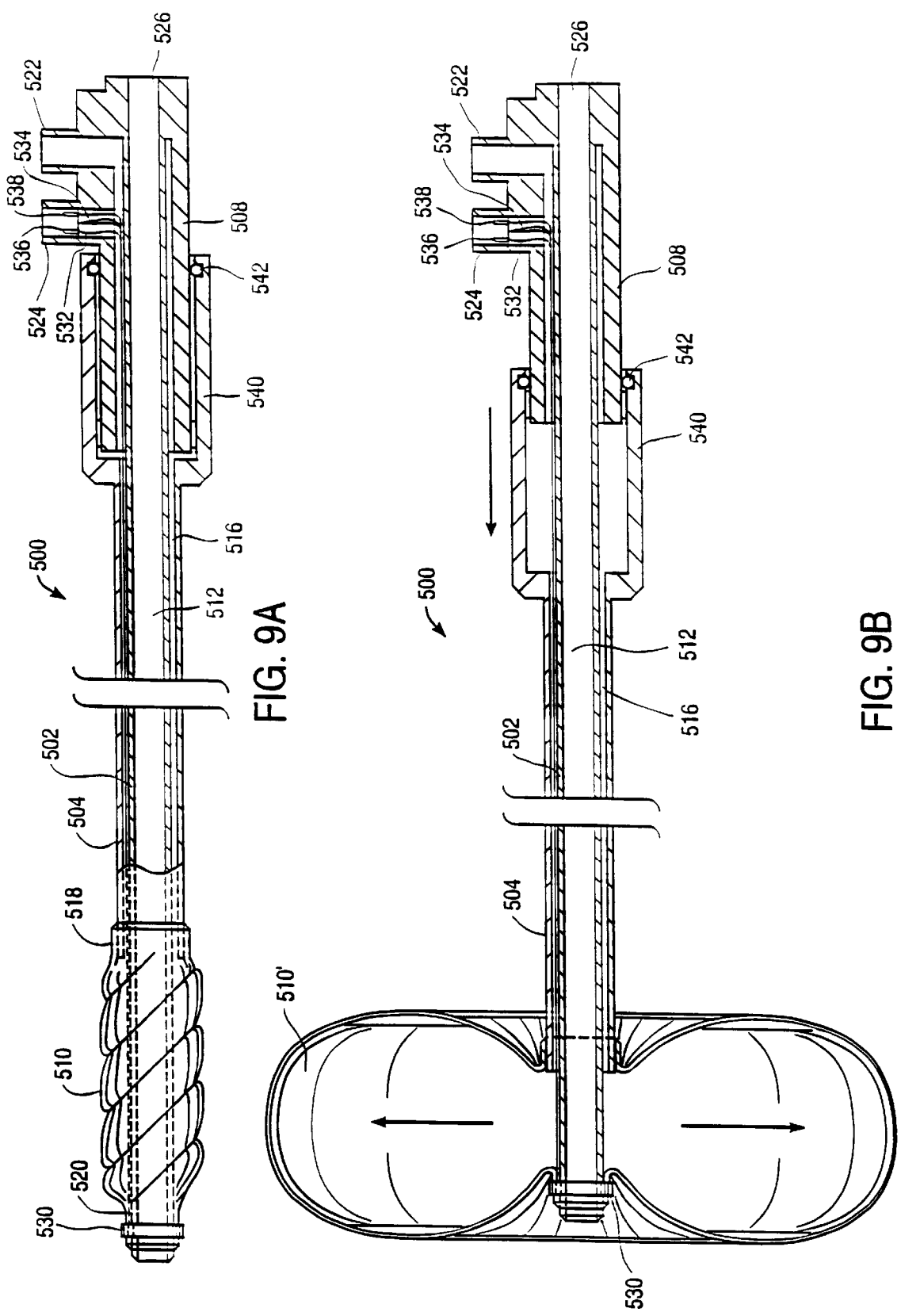

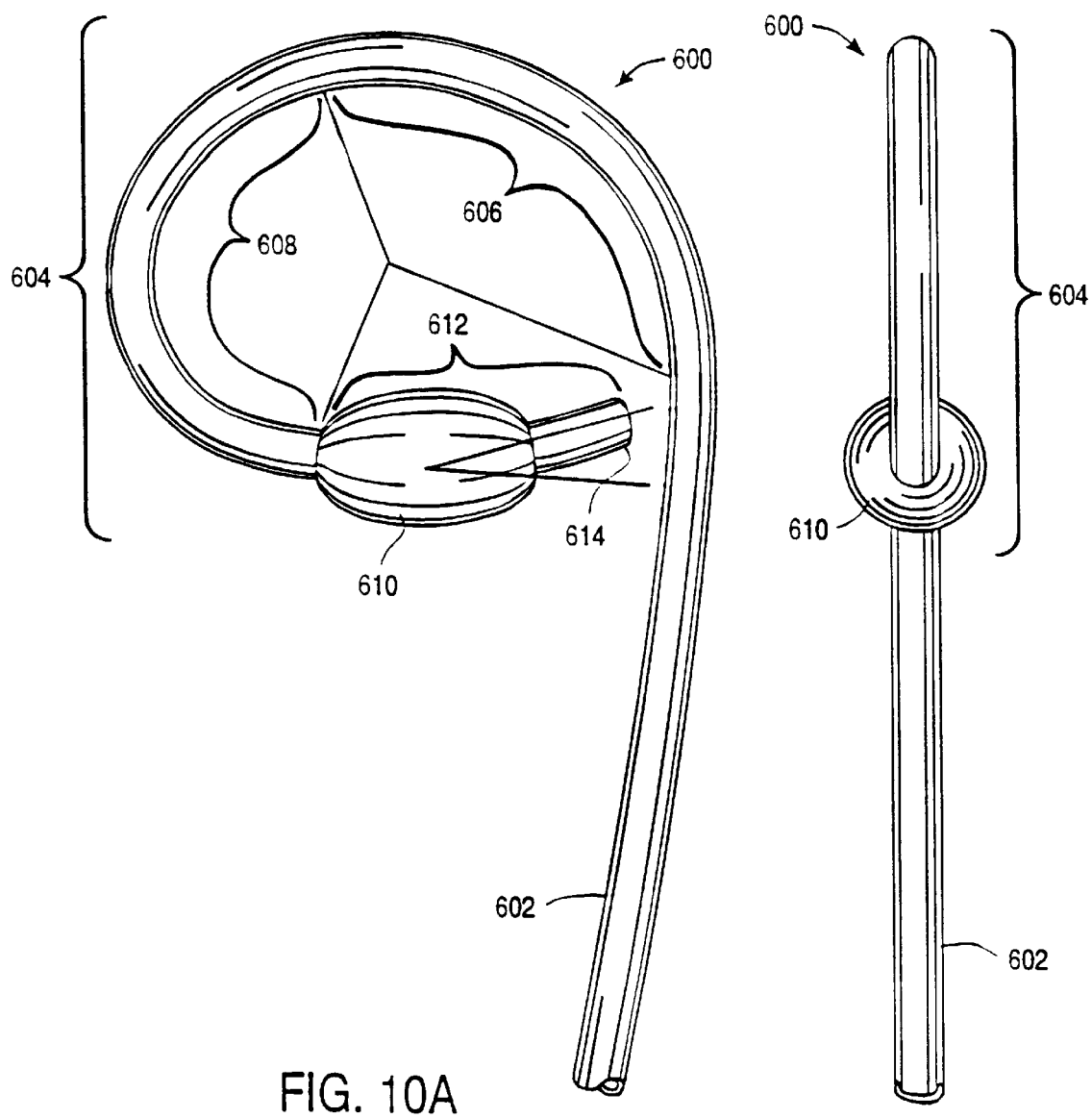
FIG. 10A
FIG. 10B
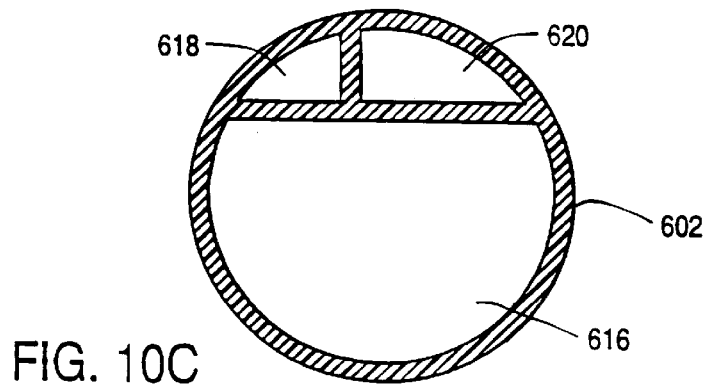
FIG. 10C

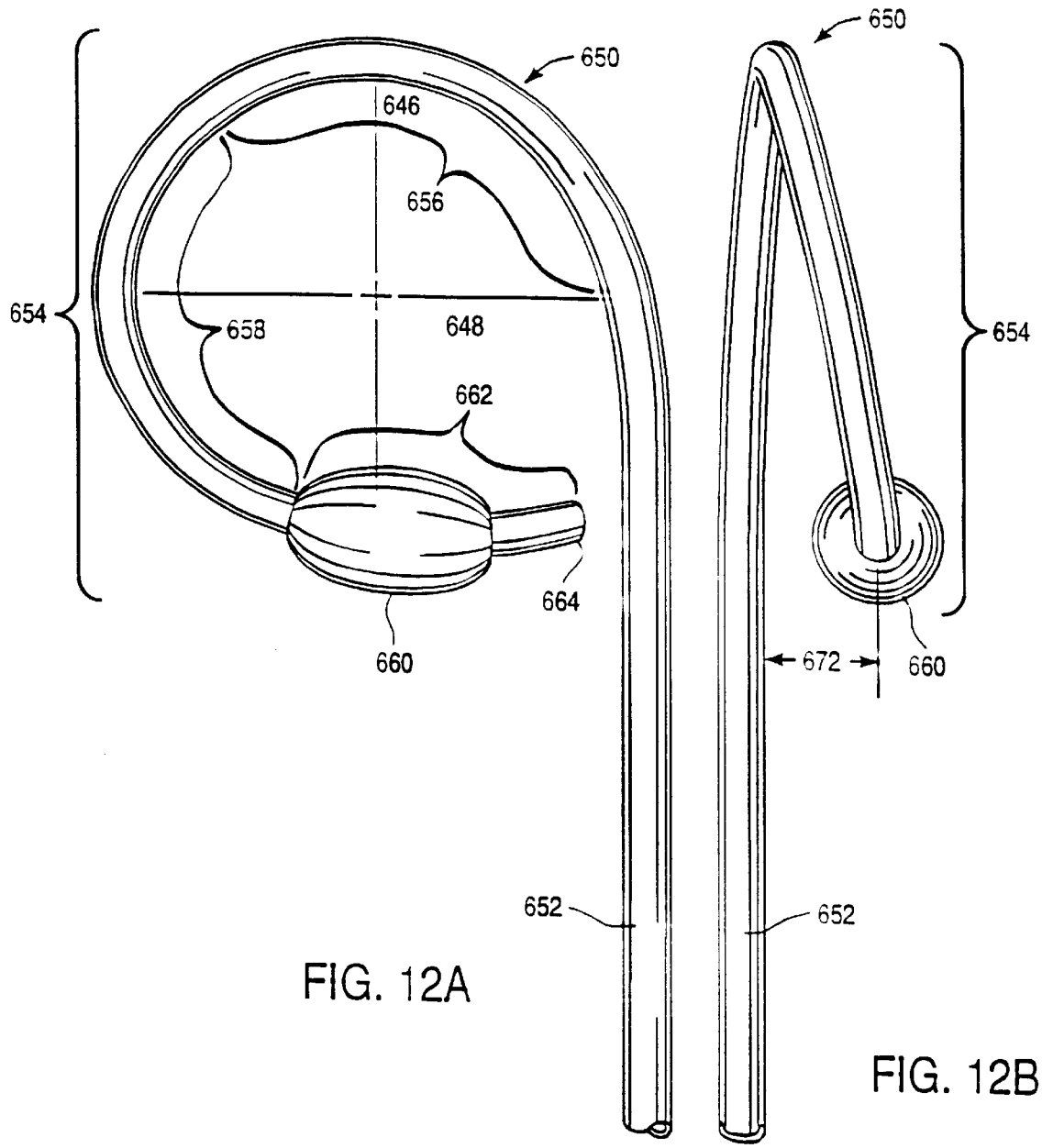
FIG. 12A
FIG. 12B
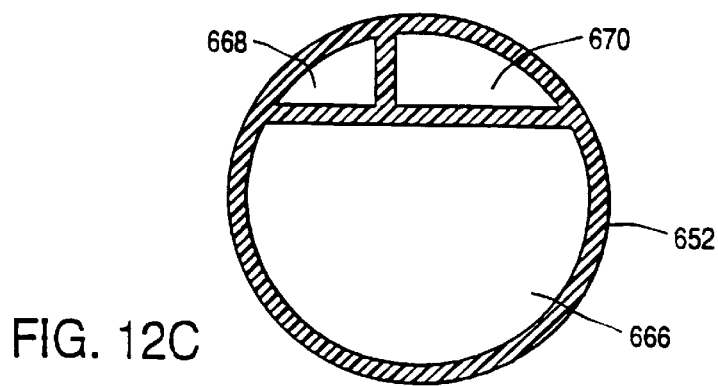
FIG. 12C

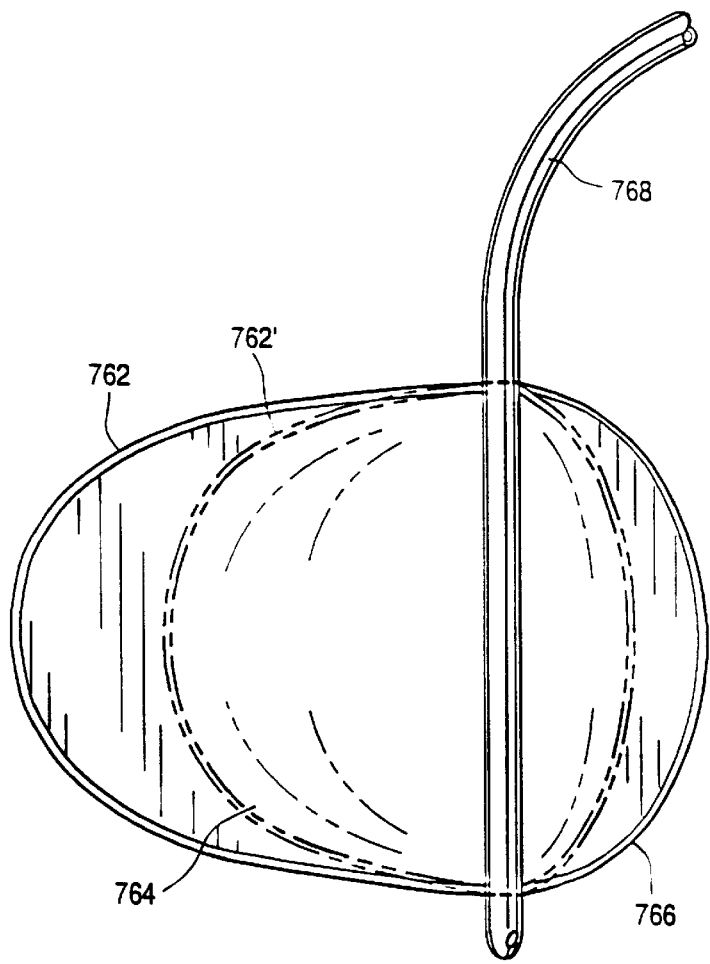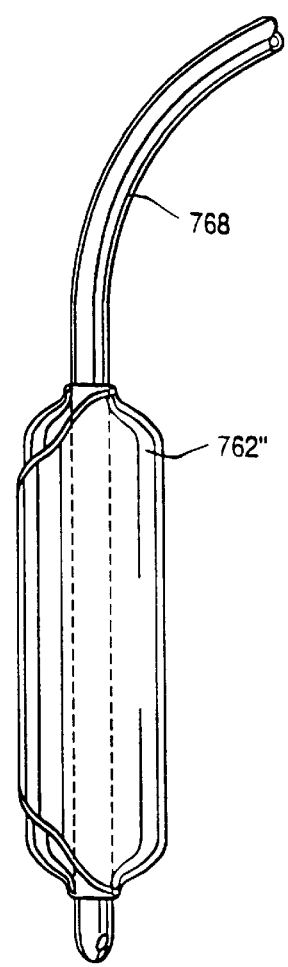
FIG. 19A        FIG. 19C
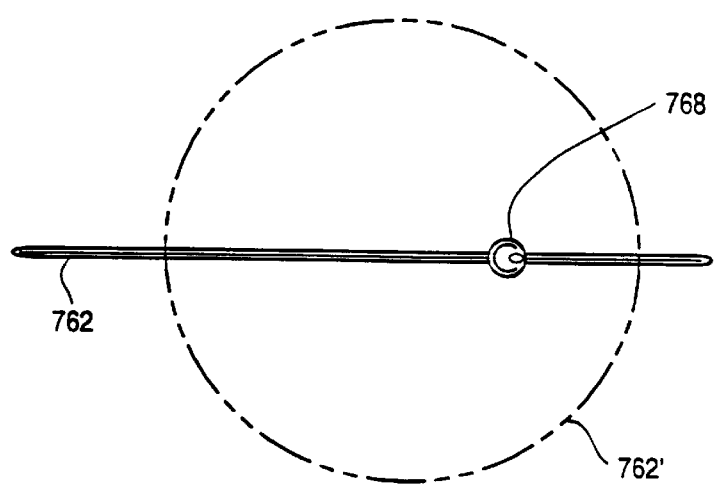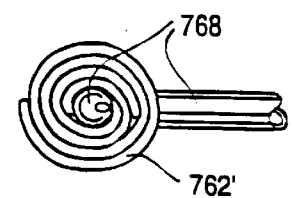
FIG. 19B        FIG. 19D

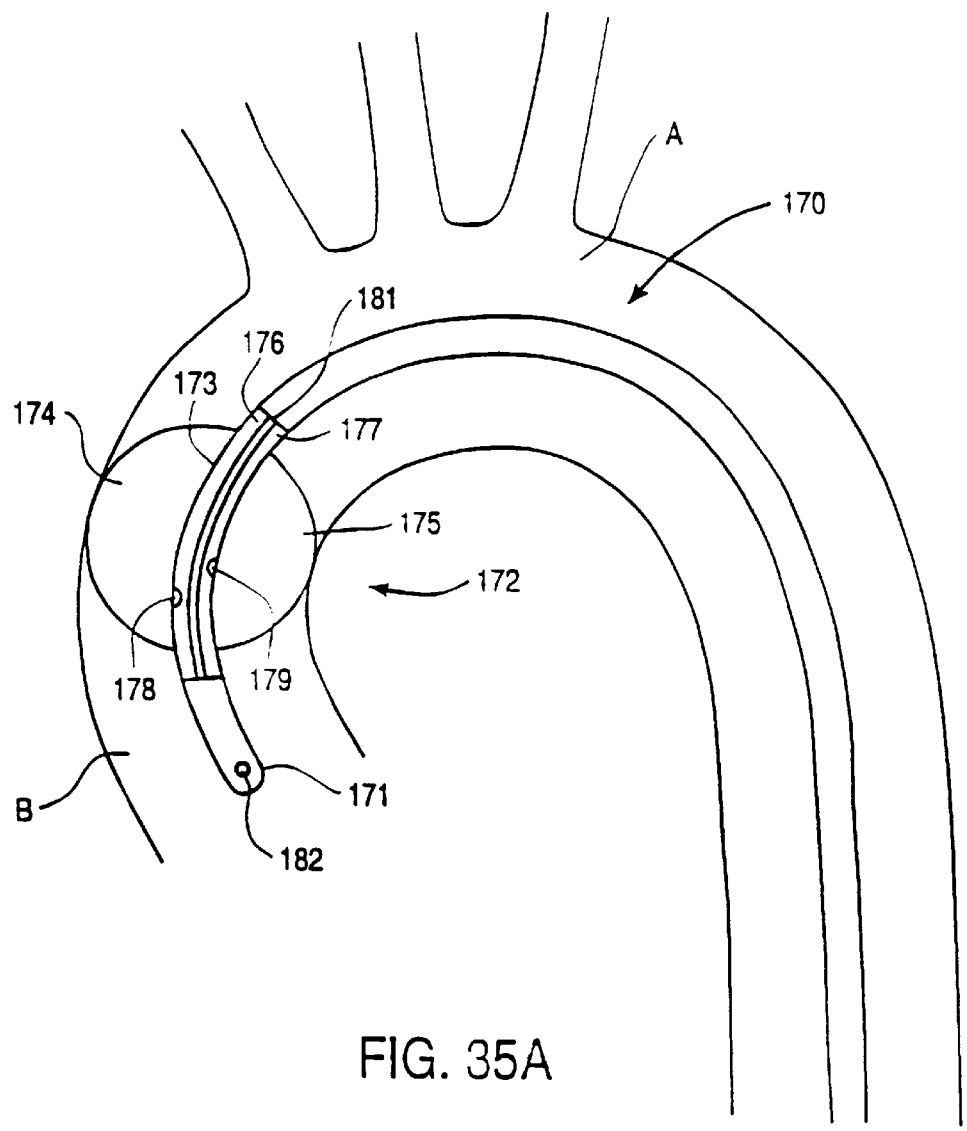
FIG. 35A
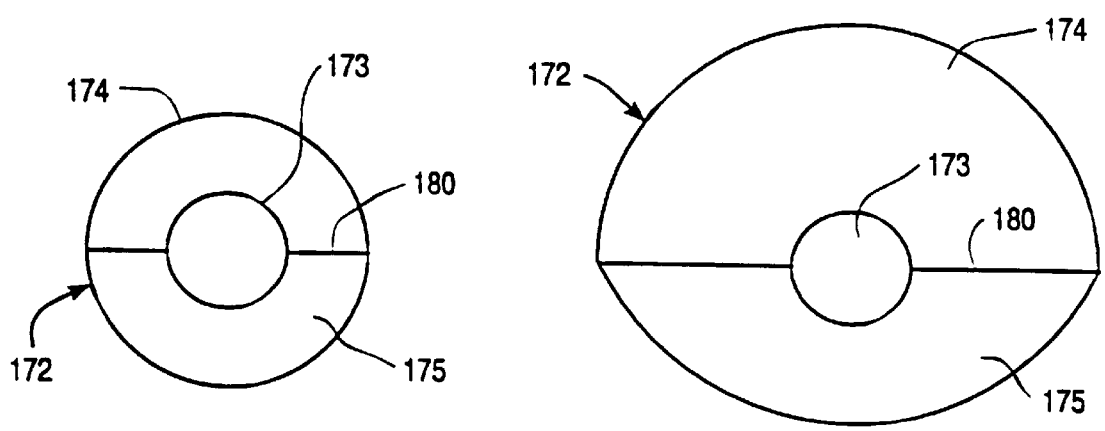
FIG. 35B
FIG. 35C

FIG. 40
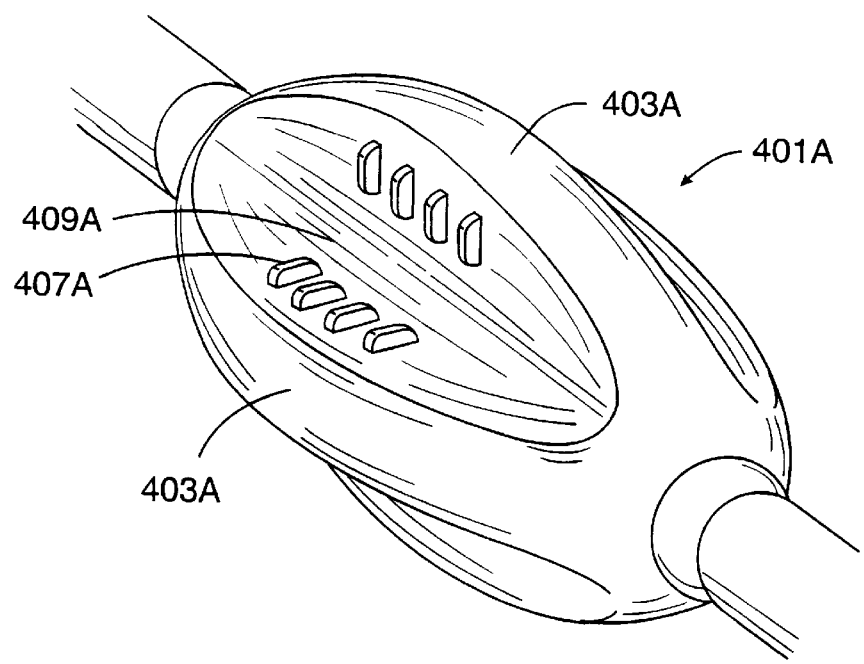
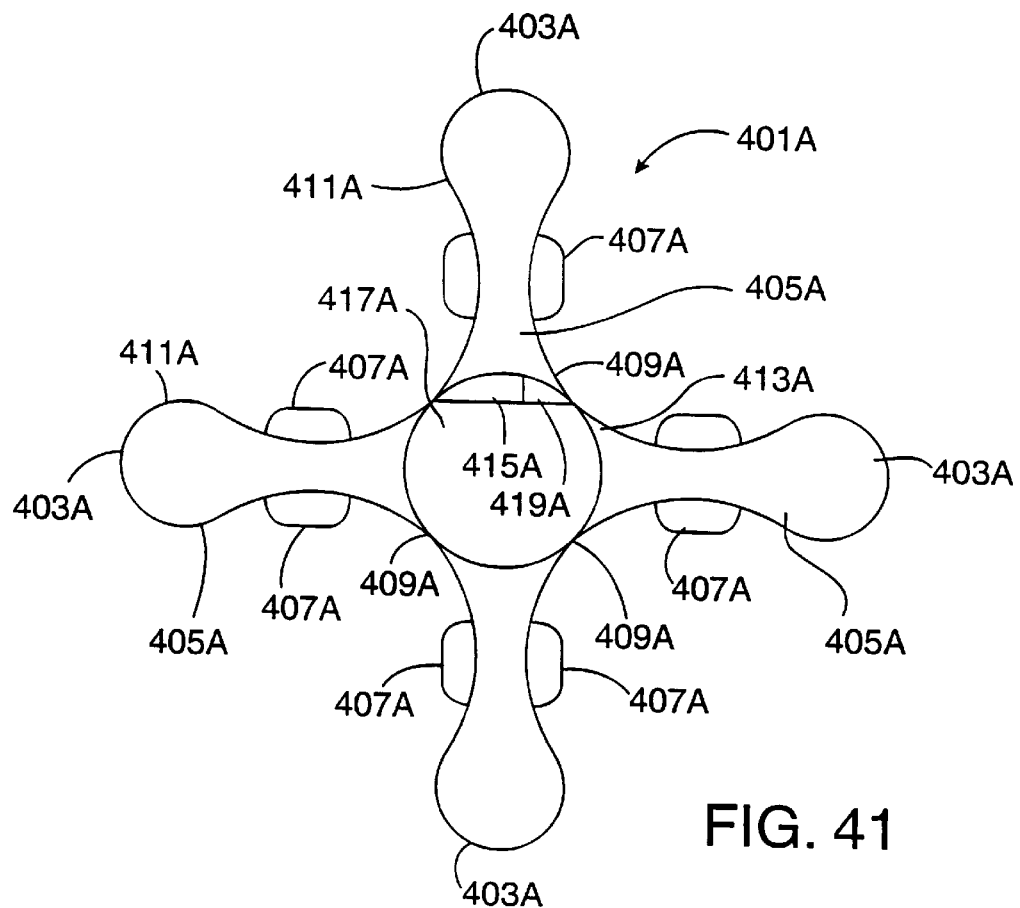
FIG. 41

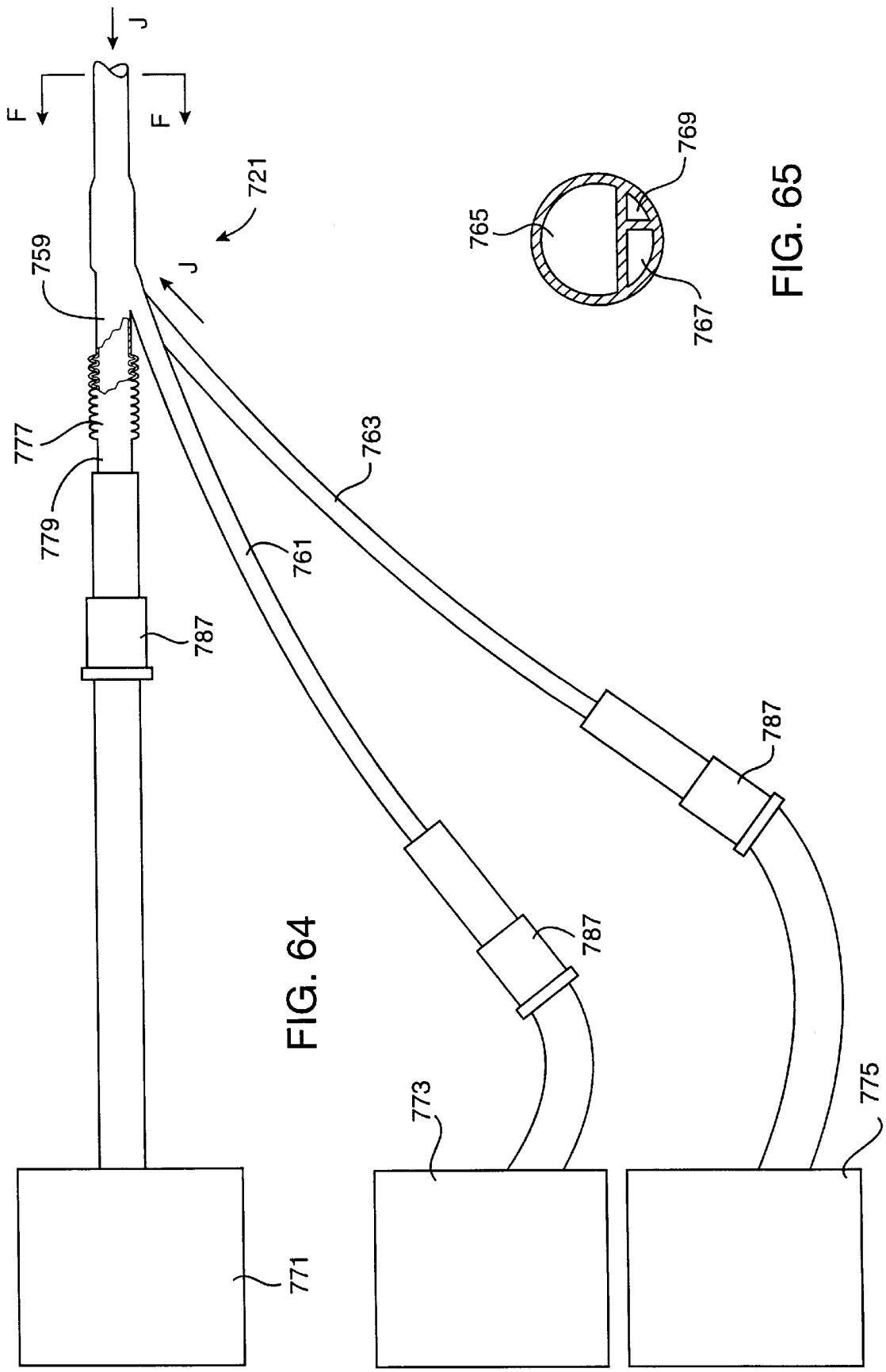

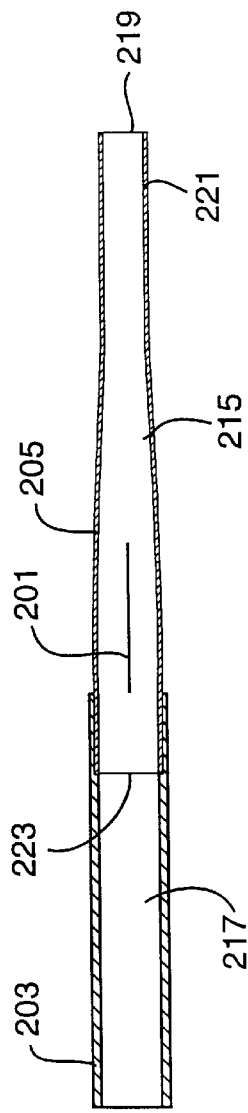
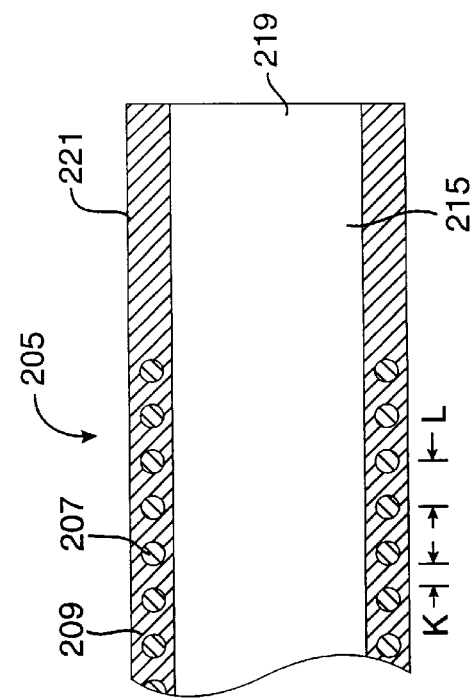
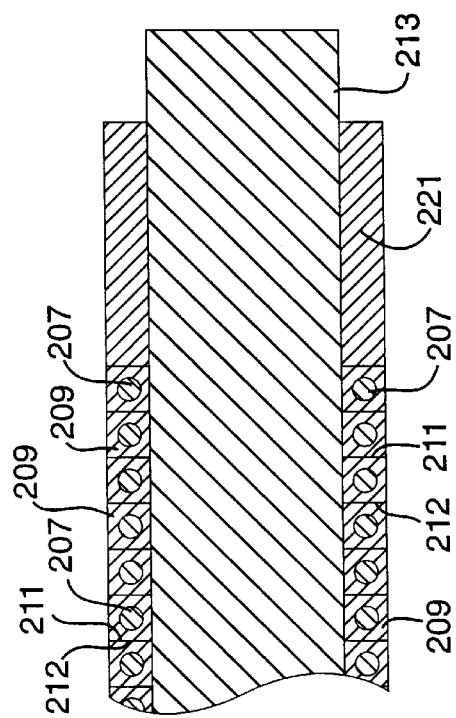
FIG. 66
FIG. 67
FIG. 68

METHOD OF MANUFACTURE OF A MULTI-LUMEN CATHETER

CROSS-REFERENCE TO RELATED APPLICATIONS

This application is related to U.S. patent application Ser. No. 08/612,230 by Snow et al., filed Mar. 7, 1996, which is a continuation-in-part of Ser. No. 08/486,216, filed Jun. 7, 1995 which is a continuation-in-part of copending U.S. patent application Ser. No. 08/282,192, filed Jul. 28, 1994, now U.S. Pat. No. 5,584,803 which is a continuation-in-part of application Ser. No. 08/162,742, filed Dec. 3, 1993, now abandoned, which is a continuation-in-part of application Ser. No. 08/123,411, filed Sep. 17, 1993, now abandoned, which is a continuation-in-part of application Ser. No. 07/991,188, now abandoned, filed Dec. 15, 1992, which is a continuation-in-part of application Ser. No. 07/730,559, filed Jul. 16, 1991, which issued as U.S. Pat. No. 5,370,685 on Dec. 6, 1994. This application is also related to copending U.S. patent application Ser. No. 08/427,384, filed Nov. 30, 1993, now U.S. Pat. No. 5,725,496, which is a divisional application of U.S. patent application Ser. No. 08/159,815 now U.S. Pat. No. 5,433,700, which is a U.S. counterpart of Australian Patent Application No. PL 6170, filed Dec. 3, 1992. This application is also related to copending U.S. patent application Ser. No. 08/281,962, filed Jul. 28, 1994, now abandoned, which is a continuation-in-part of application Ser. No. 08/163,241, filed Dec. 6, 1993, now U.S. Pat. No. 5,571,215, which is a continuation-in-part of application Ser. No. 08/023,778, filed Feb. 22, 1993 now U.S. Pat. No. 5,452,733. This application is also related to copending U.S. patent application Ser. No. 08/281,891, filed Jul. 28, 1994, now U.S. Pat. No. 5,735,290 which is a continuation-in-part of application Ser. No. 08/023,778, filed Feb. 22, 1993, now U.S. Pat. No. 5,452,733. This application is also related to copending U.S. patent application Ser. No. 08/213,760, filed Mar. 16, 1994 now U.S. Pat. No. 5,458,574. The complete disclosures of all of the aforementioned U.S. patent applications and patents are hereby incorporated herein by reference for all purposes.

FIELD OF THE INVENTION

The present invention is directed to reinforced hollow tubes and their methods of manufacture and use. A specific application of the present invention is for arterial return and venous drainage cannulas for a cardiopulmonary bypass system. The present invention is also specifically directed to an arterial return cannula and an aortic occlusion catheter for arresting a patient's heart and placing the patient on cardiopulmonary bypass.

BACKGROUND OF THE INVENTION

Cannulas for cardiopulmonary bypass systems have thin walls to optimize flow rates through the cannula for a given cannula size. Wall thickness is particularly important when using the system for arresting a patient's heart and placing the patient on cardiopulmonary bypass described in co-pending U.S. patent application Ser. No. 08/570,286, filed Dec. 11, 1995 by Valley et al., which is incorporated herein by reference. Venous blood is withdrawn through a venous cannula and directed to an oxygenator. The oxygenated blood is then returned to the patient's arterial system through an arterial cannula. An aortic occlusion catheter is used to block blood flow through the ascending aorta and deliver cardioplegic fluid to arrest the heart of the patient for performing surgery on the heart and great vessels. The aortic occlusion catheter is inserted through a lumen in the arterial cannula which is the same lumen through which arterial blood is returned.

An advantage of the system described above is that only one opening in the patient's arterial system is required for both delivery of cardioplegic fluid and return of arterial blood. In order to achieve the necessary blood and cardioplegic fluid flow rates, however, the wall of the arterial cannula must be minimized while retaining enough structural integrity to prevent kinking and cracking. The present invention is particularly useful in providing a thin walled cannula which may be used as an arterial return cannula for the system described above.

A known method of making a reinforced cannula is to dip a mandrel in a polymer solution and wrap a metal wire over the polymer. The mandrel is then dipped again to encase the metal wire between two layers of polymer.

Another known method of making a reinforced cannula is to extrude a polymer tubing, wrap a metal wire around the polymer tubing, and extrude another polymer layer over the metal wire.

A problem with the known methods of manufacturing a reinforced cannula is that the spacing between adjacent wires must be relatively large to ensure that the polymer flows between adjacent coils so that the two polymer layers bond together to form an integrated structure. Unfortunately, the relatively large spacing requires a relativley thick polymer layer to provide the necessary strength since the wire has a large pitch. The relatively thick polymer layer is also required to ensure that a sufficient amount of polymer is provided to fill the relatively large space. The resulting cannula has a relatively thick wall.

Thus, a specific object of the present invention is to provide a new method of manufacturing reinforced tubing and, in particular, cannulas for venous withdrawal and arterial return of blood for a cardiopulmonary bypass system.

As mentioned above, an aortic occlusion catheter is passed through the arterial return cannula when practicing the invention disclosed in U.S. patent application Ser. No. 08/570,286. It is also advantageous to minimize the size of the aortic occlusion catheter for the same reasons as it is advantageous to minimize the size of the arterial return cannula. A limiting factor when reducing the size of the aortic occlusion catheter is that the catheter cannot kink when extending around the aortic arch. Thus, another object of the present invention is to provide an aortic occlusion catheter which minimizes the catheter size while providing a catheter which resists kinking.

SUMMARY OF THE INVENTION

The present invention solves the problems associated with prior art methods of making venous and arterial cannulas by providing a method which produces thin walled cannulas which retain adequate structural characteristics.

The method begins with coating an elongate member, preferably with a polymer, thereby forming a coated elongate member. A preferred method of coating the material is to coextrude the material over the elongate member. The coated elongate member is then wound around a mandrel and heated so that the coating on adjacent parts of the wound elongate member bond together. The coated elongate member is then mounted to a cannula body. In a preferred method, the coated elongate member is formed so that opposing sides of the coated elongate member engage one another when the coated elongate member is wrapped around the mandrel. A preferred shape is square. An advantage of the present invention is that the coating does not need to flow between adjacent elongate members since the coated elongate members are configured to have sides which engage one another. In another aspect of the invention, the coated elongate member is compressed after being wound around the mandrel. The coated elongate member is preferably compressed with a heat shrink tube placed over the coated elongate member before heating. The shrink tube compresses the polymer to further ensure bonding between adjacent portions of the coated elongate member. A further polymer layer may also be provided on the radially inner or outer wall to increase the strength of the resulting reinforced tube.

In another aspect of the present invention, an arterial return cannula is provided with an aortic occlusion catheter slidably coupled thereto. The catheter has an occluding member movable between collapsed and expanded shapes. The expanded shape is sized and configured to occlude a patient's ascending aorta. The aortic occlusion catheter has a lumen fluidly coupled to an outlet positioned distal to the occluding member for delivering cardioplegic fluid to a patient's ascending aorta. The arterial return cannula has first and second sections. The first section has a first lumen and the second section has second and third lumens fluidly coupled to the first lumen. The catheter extends through the second lumen and into the first lumen. The third lumen is coupled to a source of oxygenated blood from a cardiopulmonary bypass system.

The first section is rotatable with respect to the second section so that tubing and the like which is coupled to the cannula and catheter can be positioned to prevent kinking. The cannula and catheter are preferably coupled to an arterial blood supply, inflation fluid, a source of cardioplegic solution, and a pressure monitor. The rotational connection between the first and second sections permits the operator to orient the first and second sections so that tubing extending from the cannula and catheter does not kink.

In another aspect of the present invention, a catheter is provided having a reinforced portion which resists kinking. In a preferred embodiment, the catheter is an aortic occlusion catheter having first and second lumens. The catheter has a reinforcing member extending around the first lumen and not the second. It is preferred to wrap the reinforcing member only around the first lumen so that the second lumen can be easily pierced to provide an inflation lumen for inflating a balloon. The catheter is preferably twisted so that the first and second lumens form helical paths. By forming the catheter in this manner, the catheter is not susceptible to kinking in any particular direction. An advantage of using the reinforcing member is that the catheter size can be reduced while the These and other aspects of the invention will become apparent with the following description of the preferred embodiments.

BRIEF DESCRIPTION OF THE DRAWINGS

FIG. 2 is a schematic partly cut-away representation of a patient's heart with the endoaortic partitioning catheter of the present invention placed within the ascending aorta.

FIG. 3 is a transverse cross-sectional view of the occluding catheter shown in FIG. 2 taken along the lines 3—3.

FIG. 4. is an enlarged view, partially in section, of the retrograde cardioplegia delivery catheter and the pulmonary venting catheter shown in FIG. 1.

FIG. 5A is a longitudinal cross section of a first embodiment of the endoaortic partitioning catheter of the present invention. FIG. 5B is a lateral cross section of the catheter of FIG. 5A taken along the lines 5B—5B. FIG. 5C is a lateral cross section of the catheter of FIG. 5A taken along the lines 5C—5C. FIG. 5D is a detail drawing showing the construction of section 5D—5D of the catheter of FIG. 5A.

FIG. 7A is a longitudinal cross section of a third embodiment of the endoaortic partitioning catheter having piezoelectric pressure transducers. FIG. 7B is a lateral cross section of the catheter of FIG. 7A taken along the lines 7B—7B. FIG. 7C is a lateral cross section of the catheter of FIG. 7A taken along the lines 7C—7C.

FIG. 8A is a longitudinal cross section of a fourth embodiment of the endoaortic partitioning catheter having a variable length occlusion balloon with the occlusion balloon deflated. FIG. 8B is a longitudinal cross section of the catheter of FIG. 8A with the occlusion balloon inflated in an elongated position. FIG. 8C is a longitudinal cross section of the catheter of FIG. 8A with the occlusion balloon inflated in a shortened position.

FIG. 9A is a side view, partially in section, of a fifth embodiment of the endoaortic partitioning catheter having a twisted low-profile occlusion balloon. FIG. 9B is a longitudinal cross section of the catheter of FIG. 9A with the occlusion balloon inflated.

FIG. 10A is a front view of a sixth embodiment of the endoaortic partitioning catheter having a precurved distal end. FIG. 10B is a side view of the catheter of FIG. 10A. FIG. 10C is a lateral cross section of the catheter of FIG. 10A taken along the lines 10C—10C.

FIG. 12A is a front view of a seventh embodiment of the endoaortic partitioning catheter having a precurved distal end. FIG. 12B is a side view of the catheter of FIG. 12A. FIG. 12C is a lateral cross section of the catheter of FIG. 12A taken along the lines 12C—12C.

FIG. 19A is a front view of an eleventh embodiment of the endoaortic partitioning catheter having a nondistensible aortic occlusion balloon. FIG. 19B is an end view of the catheter of FIG. 19A. FIG. 19C is a side view of the catheter of FIG. 19A with the occlusion balloon wrapped around the catheter shaft. FIG. 19D is an end view of the catheter of FIG. 19C.

FIGS. 35A–35C illustrate an endoaortic partitioning catheter having a steerable distal tip with a multichamber balloon for centering the catheter tip within the ascending aorta.

FIG. 40 is an isometric view of a second preferred balloon having a first, low friction portion and a second, high friction portion.

FIG. 41 is an end view of the balloon of FIG. 40.

FIG. 64 is a side view of a trifurcated end of the shaft with one of the independent shafts having a bellows connection.

FIG. 65 is a cross-sectional view of the three lumen portion of the shaft of FIG. 64 along line F—F.

FIG. 66 is a cross-sectional view of a cannula having a reinforced section coupled to a body.

FIG. 67 is a cross-sectional view of a coated elongate member wrapped around a mandrel.

FIG. 68 is a cross-sectional view of the coated elongate member of FIG. 67 after heating and removal from the mandrel.

DETAILED DESCRIPTION OF THE INVENTION

The invention provides a cardiac access system including an endovascular device for partitioning the ascending aorta, as well as a system for selectively arresting the heart, which are useful in performing a variety of cardiovascular, pulmonary, neurosurgical, and other procedures. The procedures with which the invention will find use include repair or replacement of aortic, mitral, and other heart valves, repair of septal defects, pulmonary thrombectomy, electrophysiological mapping and ablation, coronary artery bypass grafting, angioplasty, atherectomy, treatment of aneurysms, myocardial drilling and revascularization, as well as neurovascular and neurosurgical procedures. The invention is especially useful in conjunction with minimally-invasive cardiac procedures, in that it allows the heart to be arrested and the patient to be placed on cardiopulmonary bypass using only endovascular devices, obviating the need for a thoracotomy or other large incision. Moreover, even in conventional open-chest procedures, the endovascular aortic partitioning device of the invention will frequently find use where an external cross-clamp would raise substantial risks of embolus release due to calcification or other aortic conditions.

Figure 1:
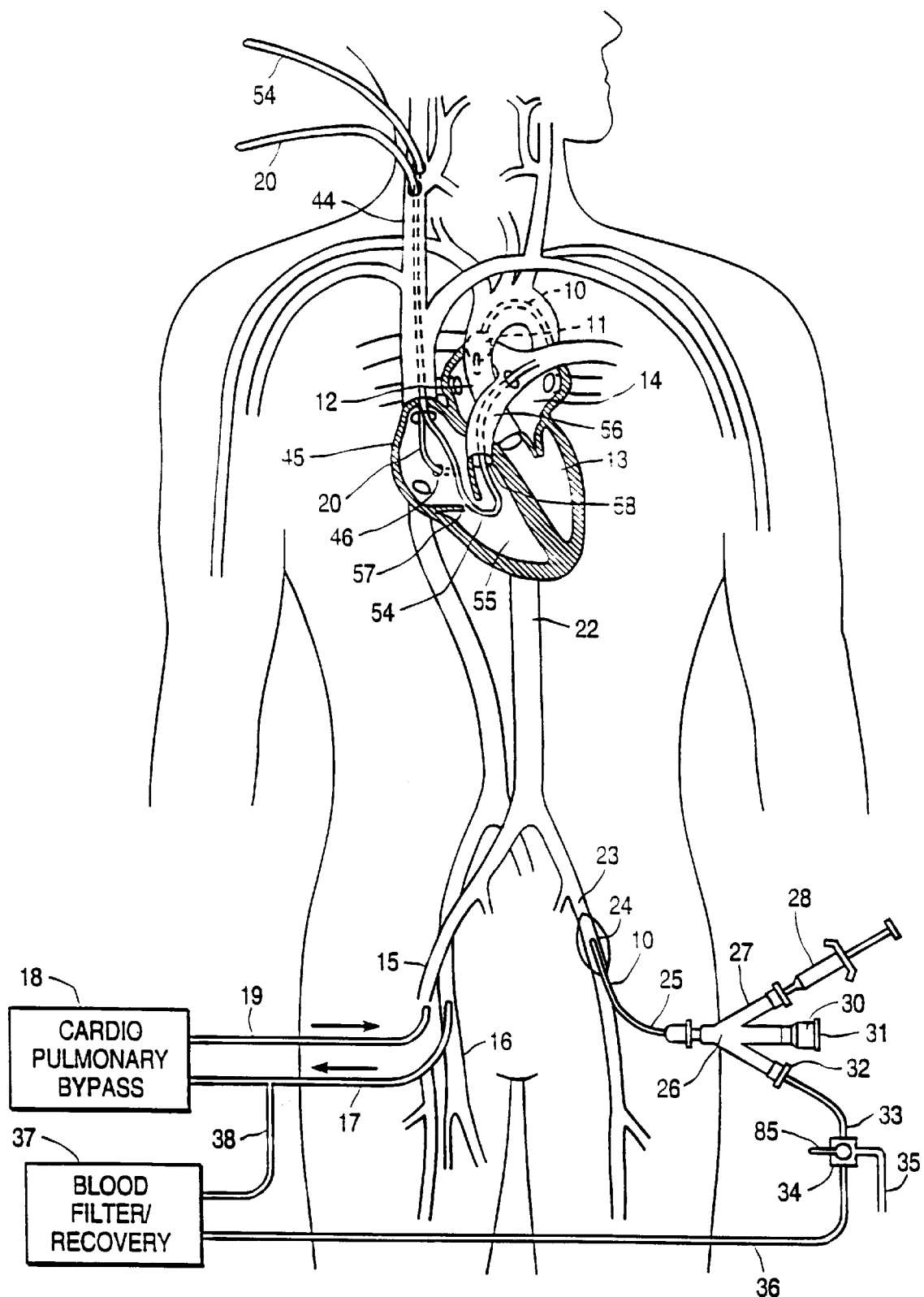
FIG. 1 schematically illustrates a cardiac access system employing the endoaortic partitioning catheter of the present invention.

Reference is made to FIG. 1 which schematically illustrates the overall cardiac accessing system of the invention and the individual components thereof. The accessing system includes an elongated aortic occlusion or endoaortic partitioning catheter 10 which has an expandable member 11 on a distal portion of the catheter which, when inflated as shown, occludes the ascending aorta 12 to separate or partition the left ventricle 13 and upstream portion of the ascending aorta from the rest of the patient's arterial system and securely positions the distal end of the catheter within the ascending aorta. A cardiopulmonary bypass system 18 removes venous blood from the femoral vein 16 through the blood withdrawal catheter 17 as shown, removes $CO_2$ from the blood, oxygenates the blood, and then returns the oxygenated blood to the patient's femoral artery 15 through the return catheter 19 at sufficient pressure so as to flow throughout the patient's arterial system except for the portion blocked by the expanded occluding member 11 on the aortic occluding catheter 10. The aortic occluding catheter 10 has an infusion lumen 40 for antegrade delivery of a fluid containing cardioplegic agents directly into the aortic root 12 and subsequently into the coronary arteries 52, 53 (shown in FIG. 2) to paralyze the patient's myocardium. Optionally, a retrograde cardioplegia balloon catheter 20 may be disposed within the patient's venous system with the distal end of the catheter extending into the coronary sinus 21 (shown in FIG. 4) to deliver a fluid containing cardioplegic agents to the myocardium in a retrograde manner through the patient's coronary venous system to paralyze the entire myocardium.

The elongated occluding catheter 10 extends through the descending aorta to the left femoral artery 23 and out of the patient through a cut down 24. The proximal extremity 25 of the catheter 10 which extends out of the patient is provided with a multi-arm adapter 26 with one arm 27 adapted to receive an inflation device 28. The adapter 26 is also provided with a second arm 30 with main access port 31 through which passes instruments, a valve prosthesis, an angioscope, or to direct blood, irrigation fluid, cardioplegic agents and the like to or from the system. A third arm 32 is provided for monitoring aortic root infusion pressure at the distal end of the catheter and/or for directing blood, irrigation fluid, and the like to or from the system. In the system configuration of FIG. 1, the third arm 32 of the multi-arm adapter 26 is connected to a cardiopulmonary bypass line 33 to vent the patient's heart, particularly the left ventricle, and to recover the blood removed and return it to the patient via the cardiopulmonary bypass system. A suitable valve 34 is provided to open and close the bypass line 33 and direct the fluid passing through the bypass line to a discharge line 35 or a line 36 to a blood filter and recovery unit 37. A return line may be provided to return any filtered blood to the cardiopulmonary bypass system 18 or other blood conservation system.

The details of the aortic occlusion catheter 10 and the disposition of the distal extremity thereof within the aorta are best illustrated in FIGS. 2 and 3. As indicated, the catheter 10 includes an elongated catheter shaft 39 which has a first inner lumen 40 for infusion of a cardioplegic agent in fluid communication with the main access port 31 in the second arm of the adapter 26. Additionally, the infusion lumen 40 may be adapted to facilitate the passage of instruments, a valve prosthesis, an angioscope, irrigation fluid, and the like therethrough and out the distal port 41 in the distal end thereof. A supporting coil 42 may be provided in the distal portion of the first inner lumen 40 to prevent the catheter shaft 39 from kinking when it straightened for initial introduction into the arterial system or when it is advanced through the aortic arch. The shaft 39 is also provided with a second inner lumen 43 which is in fluid communication with the interior of the occluding balloon 11.

In one embodiment of the system, a retrograde cardioplegia balloon catheter 20, which is shown in more detail in FIG. 4, is introduced into the patient's venous system through the right internal jugular vein 44 and is advanced through the right atrium 45 and into the coronary sinus 21 through the coronary sinus discharge opening 46 in the right atrium. The retrograde catheter 20 is provided with a balloon 47 on a distal portion of the catheter 20 which is adapted to occlude the coronary sinus 21 when inflated. A liquid containing a cardioplegic agent, e.g. an aqueous KCl solution, is introduced into the proximal end 48 of the catheter 20, which extends outside of the patient, under sufficient pressure so that the fluid containing the cardioplegic agent can be forced to pass through the coronary sinus 21, through the capillary beds (not shown) in the patient's myocardium, through the coronary arteries 50 and 51 and ostia 52 and 53 associated with the respective coronary arteries into the blocked off portion of the ascending aorta 12 as shown.

A pulmonary venting catheter 54 is also shown in FIG. 4 disposed within the right internal jugular vein 44 and extending through the right atrium 45 and right ventricle 55 into the pulmonary trunk 56. Alternatively, the pulmonary venting catheter 54 may be introduced through the left jugular. The catheter 54 passes through tricuspid valve 57 and pulmonary valve 58. An inflatable occluding balloon 60 may be provided as shown on a distal portion of the pulmonary venting catheter 54 which is inflated to occlude the pulmonary trunk 56 as shown. The pulmonary venting catheter 54 has a first inner lumen 61 which extends from the distal end of the catheter to the proximal end of the catheter which vents fluid from the pulmonary trunk 56 to outside the patient's body either for discharge or for passage to the blood recovery unit and thereby decompresses the left atrium 14 through the pulmonary capillary beds (not shown). The catheter 54 has a second inner lumen 62 which is adapted to direct inflation fluid to the interior of the inflatable balloon 60.

To set up the cardiac access system, the patient is initially placed under light general anesthesia. The withdrawal catheter 17 and the return catheter 19 of the cardiopulmonary bypass system 18 are percutaneously introduced into the right femoral vein 16 and the right femoral artery 15, respectively. An incision 24 is also made in the left groin to expose the left femoral artery 23 and the aortic occluding catheter 10 is inserted into the left femoral artery through an incision therein and advanced upstream until the balloon 11 on the distal end of the occluding catheter 10 is properly positioned in the ascending aorta 12. Note that bypass could similarly be established in the left groin and the aortic occlusion catheter put into the right femoral artery. The retrograde perfusion catheter 20 is percutaneously inserted by a suitable means such as the Seldinger technique into the right internal jugular vein 44 or the subclavian vein and advanced into the right atrium 45 and guided through the discharge opening 46 into the coronary sinus.

The pulmonary venting catheter 54 is advanced through the right or left internal jugular vein 44 or the subclavian vein (whichever is available after introduction of retrograde perfusion catheter 20) into the right atrium 45, right ventricle 55, and into the pulmonary trunk 56. The occluding balloon 60 may be inflated if necessary by inflation with fluid passing through the lumen 62 to block the pulmonary trunk 56 and vent blood therein through the lumen 61 where it is discharged through the proximal end of the catheter which extends outside of the patient. Alternatively, the occluding balloon 60 may be partially inflated with air or $CO_2$ during introduction for flow-assisted placement. The venting of the pulmonary trunk 56 results in the decompressing of the left atrium 14 and, in turn, the left ventricle. In the alternative, the venting catheter 54 may be provided with means on the exterior thereof, such as expanded coils as described in U.S. Pat. No. 4,889,137 (Kolobow), which hold open the tricuspid and pulmonary valves and perform the same function of decompressing the left atrium. See also the article written by F. Rossi et. al. in the Journal of Thoracic Cardiovascular Surgery, 1900;100:914–921, entitled "Long-Term Cardiopulmonary Bypass By Peripheral Cannulation In A Model Of Total Heart Failure", which is incorporated herein in its entirety by reference.

The operation of the cardiopulmonary bypass unit 18 is initiated to withdraw blood from the femoral vein 16 through catheter 17, remove $CO_2$ from and add oxygen to the withdrawn blood and then pump the oxygenated blood through the return catheter 19 to the right femoral artery 15. The balloon 11 may then be inflated to occlude the ascending aorta 12, causing the blood pumped out of the left ventricle (until the heart stops beating due to the cardioplegic fluid as discussed hereinafter) to flow through the discharge port 41 into the first inner lumen 40 of the occluding catheter. The blood flows through the inner lumen 40 and out the third arm 32 of the adapter 26 into the bypass line 33 and then into the blood filter and blood recovery unit 37 through the valve 34 and line 36. For blood and irrigation fluids containing debris and the like, the position of the valve 34 may be changed to direct the fluid through the discharge line 35.

In a first embodiment of the method, a liquid containing a cardioplegic agent such as KCl is directed through the infusion lumen 40 of the catheter 10 into the aortic root 12 and subsequently into the coronary arteries 52, 53 to paralyze the patient's myocardium. Alternatively, if a retroperfusion catheter 20 is provided for delivery of the cardioplegic agent, the balloon 47 on the distal extremity of the catheter 20 is inflated to occlude the coronary sinus 21 to prevent fluid loss through the discharge opening 46 into the right atrium 45. A liquid containing a cardioplegic agent such as KCl is directed through the catheter 20 into the coronary sinus 21 and the pressure of the cardioplegic fluid within the coronary sinus 21 is maintained sufficiently high, (e. g. 40 mm Hg) so that the cardioplegic fluid will pass through the coronary veins, crossing the capillary beds to the coronary arteries 50 and 51 and out the ostia 52 and 53. The cardioplegic fluid pressure within the coronary sinus 21 should be maintained below 75 mm Hg to avoid pressure damage to the coronary sinus 21. Once the cardioplegic fluid passes through the capillary beds in the myocardium, the heart very quickly stops beating. At that point the myocardium is paralyzed and has very little demand for oxygen and can be maintained in this state for long periods of time with minimal damage.

With the cardiopulmonary bypass system in operation, the heart completely paralyzed and not pumping, the left atrium and ventricle decompressed and the ascending aorta blocked by the inflated balloon 11 on the occluding catheter 10, the heart is appropriately prepared for a cardiac procedure.

Inflation of the inflatable member 11 on the distal end of the delivery catheter 10 fixes the distal end of the occluding catheter 10 within the ascending aorta 12 and isolates the left ventricle 13 and the upstream portion of the ascending aorta from the rest of the arterial system downstream from the inflatable member. The passage of any debris or emboli, solid or gaseous, generated during a cardiovascular procedure to regions downstream from the site would be precluded by the inflated balloon 11. Fluid containing debris or emboli can be removed from the region between the aortic valve and the occluding balloon 11 through the inner lumen 40 of catheter 10. A clear, compatible fluid, e.g. an aqueous based fluid such as saline delivered through the inner lumen 40 or the cardioplegic fluid discharging from the coronary ostia 52 and 53, may be maintained in the region wherein the cardiovascular procedure is to be performed to facilitate use of an angioscope or other imaging means that allows for direct observation of the cardiac procedure. Preferably, the fluid pressure in the left ventricle 13 is maintained sufficiently higher than that in the left atrium to prevent blood from the left atrium from seeping into the left ventricle and interfering with the observation of the procedure.

FIG. 5A shows a longitudinal cross section of a first preferred embodiment of the endoaortic partitioning catheter 100 of the present invention. The endoaortic partitioning catheter 100 of FIG. 5A is made with a coaxial construction, which indicates that the catheter 100 is constructed of a first, inner tube 102 within a second, outer tube 104. The inner tube 102 and the outer tube 104 of the catheter 100 combine to form an elongated shaft 106 that runs from a proximal hub 108 to the distal end of the catheter 100 having an aortic occlusion balloon 110 mounted thereon. The length of the shaft 106 is such that the catheter 100 can be introduced into the patient's aorta by way of an arterial cutdown or the Seldinger technique into a peripheral artery, such as the femoral or brachial artery, and advanced into the ascending aorta. For introduction by way of a femoral artery or iliac artery the length of the shaft 106 is preferably 80 to 125 cm. For introduction by way of a brachial artery, the carotid artery or through a penetration directly into the aorta, the length of the shaft 106 is preferably 20 to 80 cm.

In the embodiment of FIG. 5A, the inner tube 102 of the catheter 100 is a two lumen tube, having a crescent-shaped cardioplegia infusion lumen 112 which wraps around a circular distal pressure lumen 114, as shown in cross section in FIGS. 5B and 5C. The cardioplegia infusion lumen 112 and the distal pressure lumen 114 are open at the distal end of the catheter 100. The cardioplegia infusion lumen 112 preferably has a cross sectional area sufficient for delivering a mixture of warm or cooled, oxygenated blood and cardioplegia solution at a rate of from about 200 ml/min to 400 ml/min with an infusion pressure not to exceed 300 mm Hg. In one presently preferred embodiment, the cross sectional area of the cardioplegia infusion lumen 112 is approximately 5.74 mm$^2$ (0.00889 in$^2$) for a catheter with a length of about 120–130 cm. The cross sectional area of the cardioplegia infusion lumen 112 necessary to deliver the desired flow rate will vary somewhat depending on the length of the catheter shaft 106 and the ratio of blood to cardioplegic solution in the mixture. The distal pressure lumen 114 preferably has a cross sectional area sufficient to transmit the pressure within the aortic root along the length of the catheter shaft 106 without excessive damping of the pressure wave. In a preferred embodiment having a shaft length of about 120–130 cm, a distal pressure lumen 114 having an internal diameter of 0.61 mm, and therefore a cross sectional area of 0.29 mm$^2$ (0.00045 in$^2$), provides the desired pressure signal transmission.

The outer tube 104 of the catheter 100 fits coaxially around the inner tube 102 with an annular space between the two tubes providing a balloon inflation lumen 116, as shown in cross section in FIG. 3C. The external diameter of the catheter 100 can be made within the range of 8–23 French (Charrière scale), preferably in the range of 8–12 French. In one preferred embodiment of the catheter 100, the outer tube 104 has an external diameter of 3.4–3.5 mm or approximately 10.5 French (Charrière scale). In a second preferred embodiment of the catheter 100, the outer tube 104 has an external diameter of 3.2–3.3 mm or approximately 10 French (Charrière scale). An aortic occlusion balloon 110 is mounted on the distal end of the catheter 100. The aortic occlusion balloon 110 has a proximal balloon neck 118 which is sealingly attached to the outer tube 104 and a distal balloon neck 120 which is sealingly attached to the inner tube 102 of the catheter 100 so that the balloon inflation lumen 116 communicates with the interior of the balloon 110. Preferably, the balloon inflation lumen 116 has a cross sectional area of approximately 0.5–1.0 mm$^2$ (0.00077–0.00155 in$^2$) to allow rapid inflation and deflation of the aortic occlusion balloon 110. In a particular presently preferred embodiment with the described configuration, the balloon inflation lumen 116 has a cross sectional area of approximately 0.626 mm$^2$ (0.00097 in$^2$) which allows the occlusion balloon 110 be inflated to a recommended maximum volume of 40 cc with saline solution or saline solution mixed with a radiopaque contrast agent at an inflation pressure of 35 psi in 40 seconds or less, preferably in 20 seconds or less. Whether inflating by hand or using a mechanical inflation device, the inflation of the balloon is preferably volume-limited so that, although the transient, peak inflation pressure reaches approximately 35 psi, the inflation pressure decreases to about 10–12 psi to maintain balloon inflation when the balloon reaches its desired inflation volume. The balloon inflation lumen 116 also allows the occlusion balloon 110 be deflated in 60 seconds or less, preferably in 40 seconds or less. The occlusion balloon 110 can be inflated and deflated by hand using an ordinary syringe or it can be inflated and deflated using an inflation device which provides a mechanical advantage or that is powered by compressed air or an electric motor.

FIG. 5D is a detail drawing showing the construction of section 5D—5D of the catheter 100 of FIG. 5A. The proximal balloon neck 118 is bonded to the distal end of the outer tube 104 in a lap joint. The bond between the proximal balloon neck 118 and the outer tube 104 and the bond between the distal balloon neck 120 and the inner tube 102 can be formed by adhesive bonding, by solvent bonding or by heat bonding depending on the materials chosen for each component. Alternatively, the outer tube 104 can be formed from a single continuous extrusion with the material of the aortic occlusion balloon 110.

The proximal hub 108 of the catheter 100 has a luer fitting balloon inflation port 122 that is sealingly connected to the balloon inflation lumen 116, a luer fitting pressure monitoring port 124 that is sealingly connected to the distal pressure lumen 114, and an infusion port 126 that is sealingly connected to the cardioplegia infusion lumen 112. The proximal hub 108 may be joined to the proximal ends of the inner tube 102 and the outer tube 104 by adhesive bonding, by insert molding or by other known processes.

In the embodiment of FIG. 5A, the aortic occlusion balloon 110 is shown as having a generally spherical geometry in the unexpanded state 110, as well as a generally spherical geometry in the expanded or inflated state 110'. Other possible geometries for the balloon in the unexpanded state 110 include cylindrical, oval or football-shaped, eccentric, asymmetric or other shaped balloons. Some of these variations are further described below. In this preferred embodiment the balloon 110 is made of an elastomeric material that expands elastically from the uninflated to the inflated state. Preferred materials for the balloon 110 include latex, silicone, and polyurethane, chosen for their elasticity, strength and biocompatibility for short term contact with the blood and body tissues.

Figure 6A:
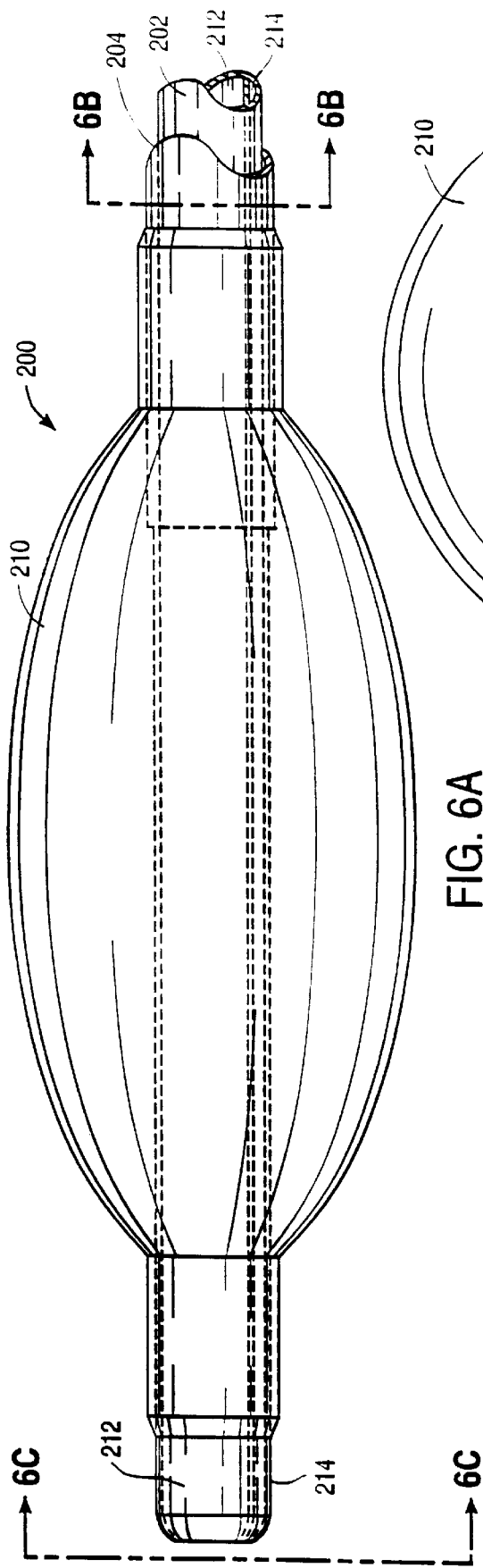
FIG. 6A is a lateral side view of a second embodiment of the endoaortic partitioning catheter.

FIG. 6A shows a lateral side view of a second preferred embodiment of the endoaortic partitioning catheter 200. In this embodiment the inner tube 202 has been made with a D-shaped cardioplegia infusion lumen 212 and a D-shaped distal pressure lumen 214. The choice of D-shaped lumens in the inner tube 202, makes it possible to maximize the diametrical clearance within the cardioplegia infusion lumen 212 for a given cross sectional area, as compared to the crescent-shaped cardioplegia infusion lumen 112 of FIG. 5C. This variation of the catheter 200 may be preferable when catheters or other instruments are to be introduced to the heart and its associated blood vessels through the cardioplegia infusion lumen 212.

As shown in FIG. 6A, the occlusion balloon 210 of this embodiment has an ellipsoidal or football-shaped deflated profile which is imparted by the balloon molding process. The wall thickness of the molded balloon 210 in its deflated state is typically about 0.090–0.130 mm. Typically, the deflated balloon 210 has a diameter of approximately 12 mm before it is folded, although deflated balloon diameters of 3 to 20 mm are possible. The inflated balloon 210' assumes a roughly spherical shape with a maximum diameter of approximately 40 mm when inflated. The football shape of the molded balloon has been shown to be advantageous in that the deflated balloon 210 has a deflated profile which is less bulky and smoother than for other balloon geometries tested. This allows the deflated balloon 210 to be folded and more easily inserted through a percutaneous puncture into the femoral artery or through an introducer sheath or a dual function arterial cannula and introducer sheath. In this embodiment as well, the balloon 210 is preferably made of an elastomeric material such as latex, silicone, or polyurethane. In one particular embodiment, the football-shaped balloon has an internal geometry determined by a positive dip molding mandrel with a radius of curvature in the central portion of the balloon of approximately 1.0 inch with a maximum diameter in the center of the balloon of about 0.5 inch. The curvature of the central portion of the balloon has a smoothly radiused transition, for example with a radius of about 0.25 inch, to the proximal and distal balloon sleeves, which are sized to fit snugly onto the exterior of the chosen diameter catheter shaft.

FIG. 7A shows a longitudinal cross section of a third preferred embodiment of the endoaortic partitioning catheter 300. The catheter 300 of this embodiment has a coaxial construction having a single lumen inner tube 302 surrounded by a single lumen outer tube 304. The single lumen inner tube 302 has a circular cardioplegia infusion lumen 312 that is connected on its proximal end to the infusion port 326 of the proximal hub 308 of the catheter 300. The cardioplegia infusion lumen 312 is open at the distal end of the catheter 300. The single lumen outer tube 304 of the catheter 300 fits coaxially around the inner tube 302 with an annular space between the two tubes providing a balloon inflation lumen 316. The balloon inflation lumen 316 is connected on its proximal end to the balloon inflation port 322 of the proximal hub 308.

In this embodiment, the aortic root pressure monitoring function is fulfilled by a distal pressure transducer 330 mounted at the distal tip 332 of the catheter 300. The distal pressure transducer 330 electronically monitors the aortic root pressure and transmits a signal along signal wires 334 and 336 to electrical connections 338 and 340 within an electrical connector 324 on the proximal hub 308 of the catheter 300. The electrical connector is adapted to be connected to an electronic pressure monitor which displays an analog or digital indication of the pressure at the distal end 332 of the catheter 300. The distal pressure transducer 330 is preferably a piezoelectric pressure transducer which creates a voltage signal indicative of the external fluid pressure exerted on the transducer 330. Examples of piezoelectric materials suitable for construction of the distal pressure transducer 330 include piezoelectric polymers such as polyvinylidene bifluoride or Kynar™ (Elf Atochem SA), or piezoelectric ceramics such as lead barium titanate, zirconium barium titanate or other commercially available piezoelectric materials. The geometry of the distal pressure transducer 330 may be a ring encircling the distal tip 332 of the catheter 300, as shown in FIGS. 7A and 7B. Alternatively, a small patch of the piezoelectric material may be mounted on one side of the distal tip 332 of the catheter 300. The distal pressure transducer 330 preferably has a pressure sensing range from about −75 to 300 mm Hg or greater (−1.5 to 5.7 psi) so as to be able to measure root pressure during cardioplegia infusion and during venting of the aortic root.

Optionally, a balloon pressure monitoring transducer 350 may also be mounted within the balloon 310 of the catheter 300 for monitoring the inflation pressure of the balloon 310. The balloon pressure monitoring transducer 350 electronically monitors the balloon inflation pressure and transmits a signal along signal wires 352 and 354 to electrical connections 356 and 358 within the electrical connector 324 on the proximal hub 308 of the catheter 300. The balloon pressure monitoring transducer 350 is preferably a piezoelectric pressure transducer which creates a voltage signal indicative of the external fluid pressure exerted on the transducer 350, made for example from one the piezoelectric polymers or piezoelectric ceramics designated above in connection with the distal pressure transducer 330. The balloon pressure monitoring transducer 350 preferably has a pressure sensing range from about −760 to 300 mm Hg or greater (−15 to 35 psi) so as to be able to measure balloon pressure during inflation and deflation of the occlusion balloon 310. The balloon pressure monitoring transducer 350 can be used to monitor internal balloon pressure to make sure that the occlusion balloon 310 has been inflated to proper pressure to insure reliable occlusion of the ascending aorta. The balloon pressure monitoring transducer 350 can also be used to determine when the occlusion balloon 310 has contacted the interior wall of the ascending aorta by monitoring for a spike in the inflation pressure within the balloon or for an inflection point in the pressure/volume curve while inflating. A safe inflation volume can be determined for each individual patient by a protocol wherein the occlusion balloon 310 is inflated until it contacts the interior wall of the ascending aorta, then a set volume of inflation fluid is added to create a reliable seal to occlude the aortic lumen. Alternatively, the protocol for inflation could include determining when the occlusion balloon 310 contacts the aortic wall and incrementally increasing the pressure a set amount to form a seal.

In a specific embodiment, the pressure transducer 350 monitors the pressure in the balloon 310 and transmits the pressure information to a pressure monitor 353 via signal wires 352, 354 and electrical connections 356, 358. The pressure monitor 353 is also coupled to a source of inflation fluid 355 for determining an amount of inflation fluid injected into the balloon 310. The pressure monitor 353 is configured to determine the rate of pressure increase relative to the fluid volume injected in the balloon 351 from the fluid source 355. The pressure monitor 353 determines when a pressure spike in the pressure vs. fluid volume is detected. The pressure spike generally indicates that the balloon 310 has engaged the aortic lumen at which point the pressure increases more rapidly with respect to the fluid volume. The slope of the pressure spike which triggers the pressure monitor 353 depends upon a number of factors including the size, shape and elasticity of the balloon 310. It is contemplated that the magnitude of the pressure spike may be determined empirically by testing balloons with various size passageways. After the pressure spike is detected, the pressure monitor 353 sends a signal to the source of inflation fluid 355 to either add a predetermined amount of fluid or to add fluid until a predetermined increase in pressure is sensed. The predetermined amount of fluid and/or predetermined increase in pressure both add an additional amount of holding force to prevent migration of the balloon while minimizing distention of the aorta.

In yet another aspect of the invention, the catheter includes a proximal pressure transducer 331 which monitors the pressure on a proximal side of the balloon 351 and transmits a signal to the pressure monitor 353 via wires 339, 341. The pressure transducer 330 and proximal pressure transducer 331 are coupled to the pressure monitor 353 which monitors the pressures and, furthermore, determines a pressure differential between the transducers 330, 331. The pressure monitor 353 preferably includes an alarm 357, which may be a visual or audible alarm, which tells the user that the pressure differential measured by the transducers 330, 331 exceeds a predetermined threshold.

When the pressure differential exceeds the predetermined threshold, the pressure on one or both sides of the balloon 351 is adjusted so that the pressure differential does not exceed the predetermined threshold. When the catheter 300 is used in conjunction with cardiopulmonary bypass as explained above, the catheter 300 delivers cardioplegic fluid through the infusion port from a source of cardioplegic fluid 359. The delivery of cardioplegic fluid from the source of cardioplegic fluid 359 may be adjusted so that the pressure differential does not exceed the predetermined threshold. Alternatively, the pressure on the proximal side of the balloon may be adjusted so that the pressure differential is below the threshold differential pressure. The above described embodiments having the pressure transducers 330, 350, 331 and pressure monitors 353 described in conjunction with the embodiment of FIG. 7A may be used with any other occluding member or balloon and are generally directed to techniques for minimizing migration of occluding members. Furthermore, although the use of pressure transducers 330, 350, 331 is preferred, any other devices for measuring the balloon and fluid pressures may be used without departing from the scope of the invention.

The signal wires 334, 336, 339, 341, 352, 354 from the pressure transducers 330, 350, 331 extend through the annular inflation lumen 316 between the inner tube 302 and the outer tube 304. The signal wires 334, 336, 352, 354, 339, 341 may be laid loosely in the inflation lumen 316 with some slack, or they may be spiraled around the inner tube 302 so that they do not adversely affect the bending characteristics of the catheter 300. Alternatively, the signal wires may be embedded in the wall of the inner tube 302, either during the extrusion process or in a post-extrusion operation. In order to have electrical impedance to match the impedance of the transducers 330, 350 and/or the electronic pressure monitor 353, the signal wires may be provided as parallel pairs, twisted pairs or coaxial cables, as required.

The use of a distal pressure transducer 330 for monitoring aortic root pressure eliminates the need for a separate pressure monitoring lumen in the catheter as provided in the embodiments of FIGS. 5A and 6A. This allows a reduction in the catheter external diameter without sacrificing catheter performance in terms of the cardioplegia flow rate in the infusion lumen 312 and the speed of balloon inflation and deflation through the balloon inflation lumen 316. A 10 French (3.3 mm external diameter) catheter constructed according to this design provides a flow rate and balloon inflation performance comparable to a 10.5 French (3.5 mm external diameter) catheter constructed with a separate pressure monitoring lumen. Reducing the external diameter of the catheter in this way has a number of clinical advantages. The smaller diameter catheter will be easier to introduce into a patient's femoral, brachial or other artery by either the Seldinger technique or by an arterial cutdown or by insertion through an introducer sheath. It will also be possible to introduce the smaller diameter catheter into smaller arteries, as encountered in smaller patients, particularly female and pediatric patients. This will increase the clinical applicability of the catheter and the method for its use to a greater patient population. In all patients, the smaller diameter catheter will cause less trauma to the artery it is introduced through, thereby reducing the likelihood of complications, such as bleeding or hematoma at the arterial access site. The smaller diameter catheter will also be particularly advantageous when used in conjunction with the dual function arterial cannula and introducer sheath described below in relation to FIGS. 31–34 because the smaller diameter shaft will occupy less of the blood flow lumen of the cannula, allowing higher blood flow rates at lower pressures. With these improvements, the external diameter of an endoaortic partitioning catheter for use with warm blood cardioplegia can be reduced to 8 to 10 French (2.7–3.3 mm external diameter) and for use with crystalloid cardioplegia can be reduced to 7 to 9 French (2.3–3.0 mm external diameter). Although use of the pressure transducers have been described in connection with the inflatable balloon of FIG. 7A, the pressure transducers may be used with any other occluding member without departing from the scope of the invention.

Further improvements in reducing the effective diameter of the catheter during introduction or removal of the catheter from the peripheral arterial access site can be accomplished by making the occlusion balloon self-collapsing around the catheter. Two embodiments of coaxial-construction catheters with self-collapsing occlusion balloons are shown in FIGS. 8A–8C and 9A–9B.

FIG. 8A shows a transverse cross section of a coaxial-construction endoaortic partitioning catheter 400 in which the inner tube 402 and the outer tube 404 are axially movable with respect to one another. The inner tube 402 has a cardioplegia infusion lumen 412 and a pressure monitoring lumen 414. The inner tube 402 is connected to a first proximal hub 430 with luer fitting connections 426 and 424 in communication with the cardioplegia infusion lumen 412 and the pressure monitoring lumen 414, respectively. The outer tube 404 fits coaxially around the inner tube 402 with an annular space between the two tubes providing a balloon inflation lumen 416. The outer tube 404 is connected to a second proximal hub 432 with a luer fitting connection 422 for the balloon inflation lumen 416. The inner tube 402 passes through the second proximal hub 432 exiting through a sliding fluid seal 440 that allows axial movement of the inner tube 402 with respect to the second proximal hub 432 and the outer tube 404.

In one preferred embodiment the sliding fluid seal 440 is a type of compression fitting known in the industry as a Tuohy-Borst adapter. The Tuohy-Borst adapter 440 has a compressible tubular or ring-shaped elastomeric seal 442 that fits within a bore 446 on the proximal end of the second proximal hub 432. A threaded compression cap 444 fits onto the proximal end of the second proximal hub 432. When the compression cap 444 is tightened, it compresses the elastomeric seal 442 axially, which causes the lumen 448 of the seal 442 to narrow and seal against the inner tube 402. The Tuohy-Borst adapter 440 can also be used to lock the position of the inner tube 402 with respect to the second proximal hub 432 and the outer tube 404 by tightening the compression cap 444 until the friction between the elastomeric seal 442 and inner tube 402 effectively locks them together to prevent axial movement between the two.

Figure 8D:
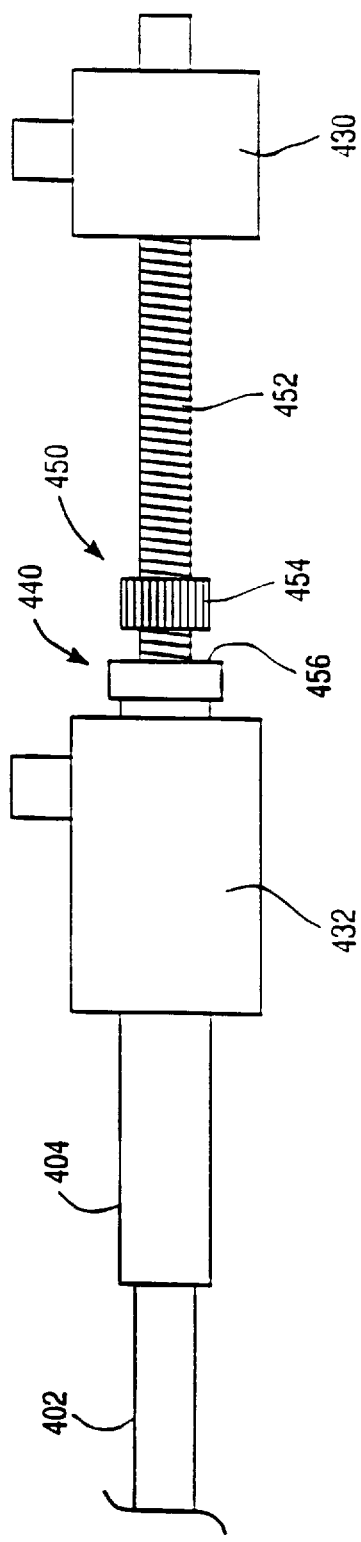
FIG. 8D shows the proximal end of an alternate embodiment of the catheter of FIG. 8A.

In a second preferred embodiment, shown in FIG. 8D, a sliding fluid seal 440 is combined with a locking mechanism 450 to lock the inner tube 402 with respect to the outer tube 404 to prevent axial movement between the two. The locking mechanism 450 may comprise a threaded shaft 452 in alignment with the inner tube 402 and a lock nut 454 threaded onto the shaft 452. By turning the lock nut 454 on the threaded shaft 452, the user can adjust the position of the inner tube 402 relative to the outer tube 404 to increase or decrease the length of the occlusion balloon 410 when inflated. The sliding fluid seal 440 may be a Tuohy-Borst adapter as described above or, because a separate locking mechanism 450 is provided, it may be a simple sliding seal, such as an O-ring or wiper seal 456, as illustrated.

Figure 6C:
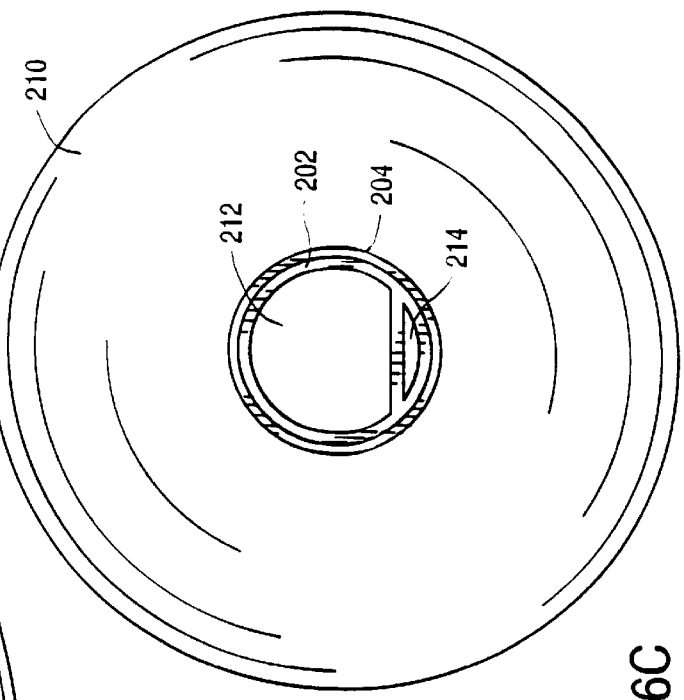
FIG. 6C is a lateral cross section of the catheter of FIG. 6A taken along the lines 6C—6C.
Figure 6B:
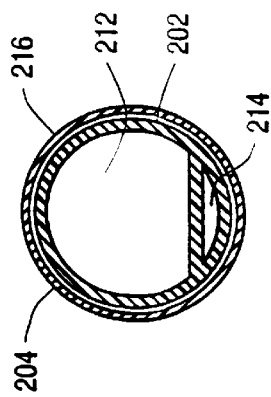
FIG. 6B is a lateral cross section of the catheter of FIG. 6A taken along the lines 6B—6B.

When the balloon 410 is deflated the inner tube 402 can be moved to its furthest distal position and locked with respect to the outer tube 404, as shown in FIG. 6A. This stretches the wall of the occlusion balloon 410 collapsing the deflated balloon tightly around the inner tube 402 to reduce the deflated profile for easy introduction through the peripheral arterial access site or through an introducer sheath. Once the occlusion balloon 410 has been advanced to the desired location in the ascending aorta, the locking mechanism 440 can be released so that the balloon 410 can be inflated. FIG. 6B shows the endoaortic partitioning catheter 400 of FIG. 1A with the inner tube 402 in an intermediate position with respect to the outer tube 404 and the occlusion balloon 410' inflated. In this position, the inner tube 402 and the outer tube 404 keeps a tension on the ends of the occlusion balloon 410' which elongates the balloon somewhat in the axial direction. This results in the balloon 410' having a somewhat oblong inflated profile which is smaller in diameter and longer axially than the typical spherical shape of a freely inflated balloon. FIG. 6C shows the endoaortic partitioning catheter 400 of FIGS. 1A and 1B with the inner tube 402 in its farther proximal position with respect to the outer tube 404 and the occlusion balloon 410" inflated. In this position, the inner tube 402 and the outer tube 404 places a compressive force on the ends of the occlusion balloon 410" which restricts the expansion of the balloon somewhat in the axial direction. This results in the balloon 410" having an inflated profile which achieves the full diameter of a freely inflated balloon diameter, but is somewhat shorter in the axial direction. This feature allows the user to select the inflated diameter of the balloon and the axial length of the balloon, and therefore the length of contact with the aortic wall, within certain ranges, as well as allowing the balloon to be more fully collapsed when deflated for insertion and removal. The range of useful balloon diameters of the occlusion balloon 410 for use in an adult human ascending aorta is from above 20 to 40 cm. Other ranges of balloon diameters may be needed for pediatric patients or nonhuman subjects.

This feature will find particular utility when the endoaortic partitioning catheter 400 is used while performing surgery or other interventional procedures on the aortic valve, or within the aortic root or ascending aorta. To facilitate the surgery, it will be important to provide as much clearance as possible between the inflated occlusion balloon 410" and the aortic valve to allow manipulation of instruments within the ascending aorta while at the same time being sure that the occlusion balloon 410" does not occlude the brachiocephalic artery. In this case, the inner tube 402 would be adjusted to its farthest proximal position with respect to the outer tube 404 before the occlusion balloon 410" is inflated in order to restrict the size of the balloon 410" as much as possible in the axial direction.

FIG. 9A shows a transverse cross section of a coaxial-construction endoaortic partitioning catheter 500 in which the inner tube 502 and the outer tube 504 are rotatable with respect to one another. The inner tube 502 has a cardioplegia infusion lumen 512 connected to a luer fitting connection 526 on the proximal hub 508. The outer tube 504 fits coaxially around the inner tube 502 with an annular space between the two tubes providing a balloon inflation lumen 516 which communicates with a luer fitting connection 522 on the proximal hub 508. The outer tube 504 is connected to a rotating collar 540 which is rotatably and slidably mounted on the distal end of the proximal hub 508. There is an O-ring seal 542 or other type of fluid tight seal between the rotating collar 540 and the proximal hub 508. An aortic occlusion balloon 510 is mounted on the distal end of the catheter 500 with the proximal balloon neck 518 sealingly attached to the outer tube 504 and the distal balloon neck 520 sealingly attached to the inner tube 502 of the catheter 500 so that the balloon inflation lumen 516 communicates with the interior of the balloon 510. The occlusion balloon 510 is preferably made of an elastomeric material, such as latex, silicone or polyurethane. A piezoelectric distal pressure transducer 530 mounted at the distal tip of the catheter 500 electronically monitors the aortic root pressure and transmits a signal along signal wires 532 and 534 to electrical connections 536 and 538 within an electrical connector 524 on the proximal hub 508 of the catheter 500.

In order to collapse the occlusion balloon 510 to its lowest possible deflated profile for introduction or withdrawal of the catheter 500 through a peripheral arterial access site or through an introducer sheath, the rotating collar 540 can be rotated with respect to the proximal hub 508 to twist the deflated occlusion balloon 510 around the inner tube 502. In addition, the rotating collar 540 can also be moved proximally with respect to the proximal hub 508 to tension the balloon to create an even lower deflated profile. After the catheter has been introduced and maneuvered to the desired position, the rotating collar 540 is counter rotated to release the balloon from its twisted state before inflation. The catheter 500 with the fully inflated occlusion balloon 510' is shown in FIG. 9B. When the catheter is to be withdrawn after use, the occlusion balloon 510 is deflated and the rotating collar 540 is again rotated and moved proximally with respect to the proximal hub 508 to twist the deflated occlusion balloon 510 around the inner tube 502 to create a lower deflated profile for removal of the catheter 500.

In each of the previously described embodiments, the shaft of the catheter, whether it has a coaxial construction or a multilumen construction, may take one of a variety of forms. In the simplest form, the shaft of the catheter may be a straight length of flexible tubing, made from a highly flexible plastic or elastomer, such as polyurethane, polyethylene, polyvinylchloride or a polyamide polyether block copolymer, preferably in the range of 35 to 72 Shore D durometer. Another variation of this embodiment would be to provide a straight shaft with zones of varying stiffness graduated from a stiff proximal section to a highly flexible distal section. The variable stiffness shaft could be made by welding tubing segments of different stiffness polymers end-to-end to create two, three or more zones of stiffness. In one illustrative embodiment, the catheter shaft could be made with a stiff proximal section of a polyamide polyether block copolymer with a hardness of 63 to 72 Shore D durometer, an intermediate section of a softer grade of the same polymer with a hardness of 55 to 63 Shore D durometer, and a distal section of a very soft grade of the polymer with a hardness of 35 to 55 Shore D durometer. In addition, an especially flexible soft tip with a hardness of 25 to 35 Shore D durometer may be molded or heat bonded to the distal end of the catheter shaft. Alternatively, the shaft can be made with continuously graduated stiffness from the proximal to distal end using a process such as total intermittent extrusion to gradually change the stiffness along the length of the catheter shaft. In a coaxial-construction catheter either or both of the inner tube and the outer tube may be made with varying stiffness to achieve the overall effect of a graduated stiffness catheter. Furthermore, either or both of the inner tube and the outer tube may be reinforced with wire or filament braiding or coils for increased stiffness, torque control or kink resistance.

The polymeric material of the shaft is preferably loaded with a radiopaque filler, such as bismuth subcarbonate, bismuth oxychloride, bismuth trioxide, barium sulfate or another radiopaque material. The shaft is preferably loaded with a level of between about 10 and 30 percent of radiopaque filler by weight, preferably about 20%. The soft tip may be loaded with a higher percent of radiopaque filler, such as about 30 to 35 percent by weight for greater fluoroscopic visibility. Instead of or in addition to the radiopaque filler, radiopaque markers, for example rings of gold, platinum, tin, tantalum or tungsten alloys may be attached to the catheter shaft at various points along the length, especially at the tip of the catheter for fluoroscopic visibility.

In such an embodiment, the highly flexible catheter would be advanced through the patient's descending aorta and into the ascending aorta with a stiffer guidewire and/and or a dilator placed in the infusion lumen of the catheter to provide stiffness for advancing and maneuvering the catheter into position. With the varying stiffness embodiment, the stiffness of the proximal shaft segment will assist in advancing and maneuvering the catheter into position. If desired, a curved guidewire or dilator may be used to assist in forming the catheter shaft to the curve of the aortic arch. Once the catheter is in position, the balloon would be inflated to occlude the ascending aorta and the guidewire or dilator withdrawn to free the infusion lumen for infusing cardioplegic fluid.

In another approach, the catheter shaft may be made of a somewhat stiffer polymer so that the distal segment of the catheter can be precurved to a configuration that assists in maneuvering the occlusion balloon into the correct position within the ascending aorta. As with the straight catheter shaft previously described, the precurved catheter shaft may also be made with varying degrees of stiffness graduated from a stiff proximal segment to a flexible distal segment. The shaft would be made of slightly higher durometer grades of a flexible plastic or elastomer, such as polyurethane, polyethylene, polyvinylchloride or a polyamide polyether block copolymer, preferably in the range of 55 to 72 Shore D durometer. A short, very flexible tip of a low durometer polymer, preferably in the range of 25 to 35 Shore D durometer, can be added to the distal end to make it less traumatic to the arterial walls and the aortic valve which it may come in contact with. Two variations of precurved catheter shafts are shown in FIGS. 10A–10C and 11A–11C. For the purposes of illustration, these embodiments are shown as built in a multilumen construction, but the precurved shafts can as well be made in one of the coaxial constructions previously described.

One preferred embodiment of an aortic partitioning catheter 600 with a precurved shaft is shown in FIG. 10A. In this embodiment the distal portion 604 of the catheter shaft 602 is configured to facilitate placement of the occlusion balloon 610 into the ascending aorta. The curve of the catheter shaft 602 also stabilizes the catheter in the proper position to prevent migration or dislodgement of the inflated occlusion balloon. The distal portion 604 of the catheter shaft 602 has a curve of approximately 270°–300° of arc. The curve of the catheter shaft 602 is a compound curve having a first segment 606 of approximately 135° of arc with a radius of curvature of approximately 75–95 mm. Contiguous with the first segment is a second segment 608 of approximately 135° of arc with a tighter radius of curvature of approximately 40–50 mm. Continuing from the second segment is a third segment 612 of approximately 25–50 mm in length adjacent to the distal end 614 of the catheter. The occlusion balloon 610 is mounted on the third segment 612 of the catheter shaft near the distal end 614 of the catheter 600. The third segment 612 of the catheter 600 may be straight, so that the total arc subtended by the catheter curve 604 is approximately 270°. Alternatively, the third segment 612 of the catheter 600 may be angled upward at a point about midway along the third segment 612, as shown in FIG. 10A, creating a total arc of curvature of about 300°. The upward angle of the third segment 612 helps the catheter 600 to follow a dilator or guidewire as it passes over the curve of the aortic arch during catheter introduction. The angle of the third segment 612 also helps to prevent the distal tip 614 of the catheter 600 from contacting the interior wall of the aorta as it passes over the aortic arch thereby reducing the likelihood of irritating or damaging the aortic wall or of dislodging calculi or other sources of potential emboli. The curve of the catheter is generally coplanar, as shown in the side view in FIG. 10B. The specifics of this catheter curve are given as an illustrative example of one preferred embodiment. The precise angles and lengths of the curve may be varied according to the geometry of the patient's anatomy based on fluoroscopic observation of the aortic arch.

A cross section of the catheter shaft is shown in FIG. 10C. The catheter shaft 602 is made from a multilumen extrusion of a flexible plastic or elastomer, such as polyurethane, polyethylene, polyvinylchloride or a polyamide polyether block copolymer, preferably in the range of 55 to 72 Shore D durometer. In one preferred embodiment, the multilumen catheter shaft 602 has a cardioplegia infusion lumen 616, a distal pressure monitoring lumen 618, and a balloon inflation lumen 620. The balloon inflation lumen 620 is in fluid communication with the interior of the inflatable occlusion balloon 610. The infusion lumen 616 and the distal pressure monitoring lumen 618 each connect with separate ports at or near the distal tip 614 of the catheter 600, distal to the occlusion balloon 610. For use with blood/cardioplegia techniques, the catheter shaft 602 preferably has an external diameter of 3.5 to 4 mm or 10.5 to 12 French (Charrière scale). For use with crystalloid cardioplegia techniques, the catheter shaft 602 may be made smaller, with an external diameter of 3.3 mm or 10 French (Charrière scale) or smaller.

Figure 11:
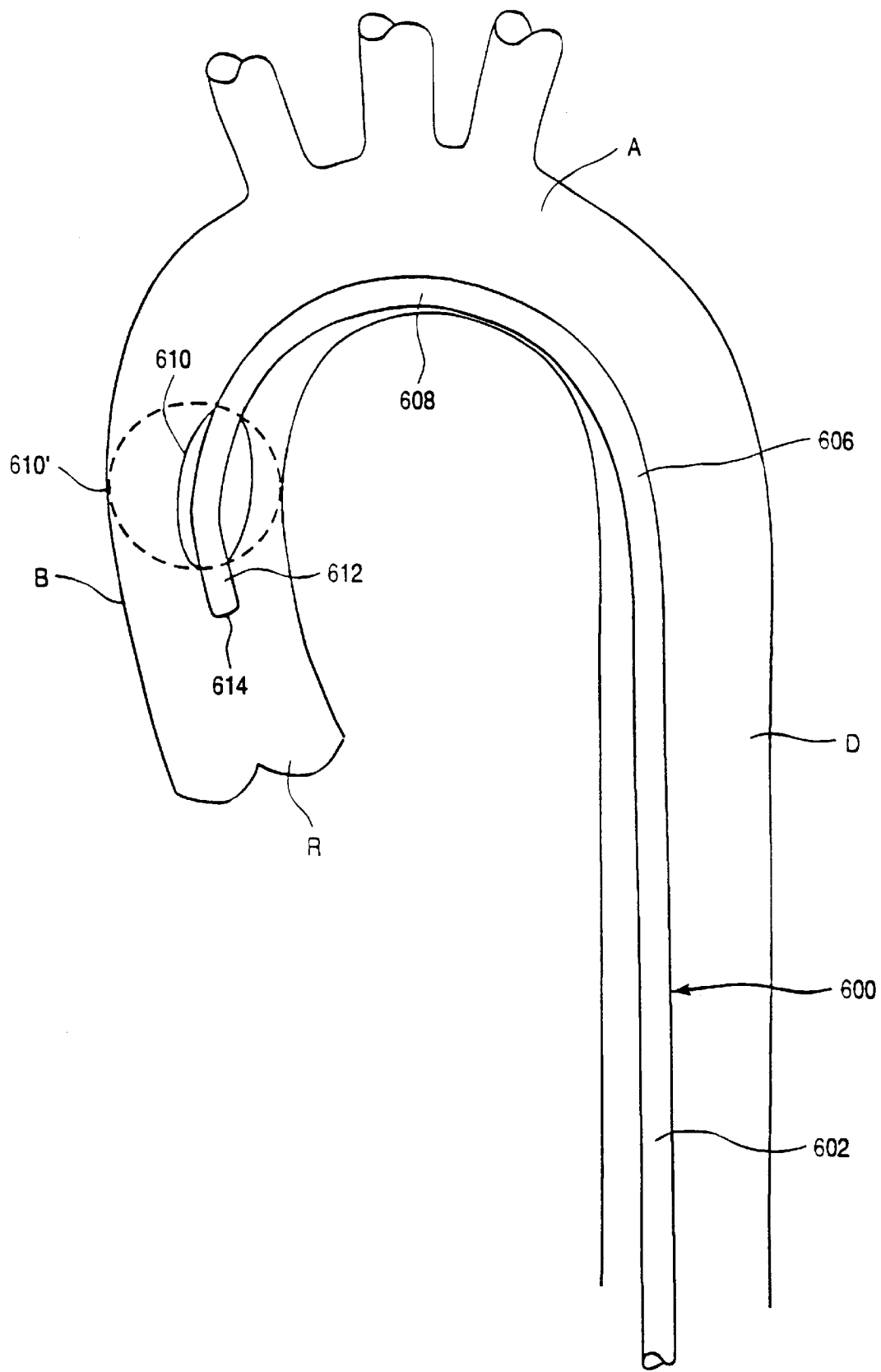
FIG. 11 is a schematic partly cut-away representation of a patient's aortic arch with the endoaortic partitioning catheter of FIG. 10A positioned in the ascending aorta.

FIG. 11 is a schematic partly cut-away representation of a patient's aortic arch A with the endoaortic partitioning catheter 600 of FIG. 10A positioned in the ascending aorta B. In use, the distal curve 604 in the catheter shaft 602 of FIG. 10A is initially straightened out by inserting a guidewire and a dilator (not shown) into the infusion lumen 616 of the catheter 600 to facilitate insertion of the catheter 600 into a peripheral arterial access site such as the femoral artery. The catheter 600 is advanced until the distal end 614 of the catheter 600 is at the apex of the aortic arch A. Then, the dilator is withdrawn as the catheter 600 is advanced over the aortic arch A to allow the curved distal portion 604 of the catheter 600 to resume its curve within the ascending aorta B. When the catheter 600 is in proper position in the ascending aorta B, the second segment 608 of the curved shaft conforms to the aortic arch A to hold the distal tip 614 of the catheter centered just above the aortic root R. The first curved segment 606 of the catheter shaft resides in the descending aorta D, somewhat straightened by its contact with the aortic walls. If the patient has a relatively straight ascending aorta B, as observed fluoroscopically, a straight third segment 612 of the curved shaft is preferred for proper centering of the catheter tip 614 when the occlusion balloon 610' is inflated. If the ascending aorta B is curved, a curved or angled distal segment 612, such as the one illustrated in FIG. 10A, is preferred.

Another preferred embodiment of an aortic partitioning catheter 650 with a precurved shaft is shown in FIG. 12A. In this embodiment also the distal portion 654 of the catheter shaft 652 is configured to facilitate placement of the occlusion balloon 660 into the ascending aorta and to stabilize the catheter in the proper position to prevent migration or dislodgement of the inflated occlusion balloon 660', but with a slightly different geometry to accommodate variations in the patient's anatomy. The distal portion 654 of the catheter shaft 652 has an approximately elliptical curve which subtends approximately 270–300 degrees of arc. The minor axis 646 of the ellipse is parallel to the shaft 652 of the catheter and has a length of about 50 to 65 mm. The major axis 648 of the ellipse is perpendicular to the shaft 652 of the catheter and has a length of about 55 to 70 mm. The elliptical curve can also be viewed as having a first segment 656 with a larger radius of curvature, a second segment 658 with smaller radius of curvature and a third segment 662 on which the occlusion balloon 660 is mounted. The curved distal portion 654 of the catheter 650 is somewhat out of plane with the catheter shaft, angling or spiraling anteriorly from the plane of the catheter shaft by about 10°–20°, as shown in FIG. 12B. In one presently preferred embodiment, the distal tip 664 of the catheter 650 has an offset 672 from the plane of the catheter shaft 652 of approximately 14 mm. The offset 672 of the spiral curve helps to center the catheter tip 664 within the ascending aorta in patients in whom the ascending aorta is angled anteriorly. The preferred degree of offset 672 can vary significantly depending on patient anatomy, with an anticipated range of from 0 to 25 mm of offset 672 to accommodate most patients. Again, this catheter curve is given as an example of one preferred embodiment. The precise angles and lengths of the curve should be chosen according to the geometry of the patient's anatomy based on fluoroscopic observation of the aortic arch. Providing the catheters in a family of curves which are variations of the curves shown in FIGS. 10A and 12A, etc. will allow the user to select the proper catheter curve for the patient after observing the geometry of the aorta fluoroscopically.

A cross section of the catheter shaft is shown in FIG. 12C. The catheter shaft 652 is made from a multilumen extrusion of a flexible plastic or elastomer, such as polyurethane, polyethylene, polyvinylchloride or a polyamide polyether block copolymer, preferably in the range of 55 to 72 Shore D durometer. In this illustrative embodiment, the multilumen catheter shaft 652 has a cardioplegia infusion lumen 666, a distal pressure monitoring lumen 668, and a balloon inflation lumen 670. The balloon inflation lumen 670 is in fluid communication with the interior of the inflatable occlusion balloon 660. The infusion lumen 666 and the distal pressure monitoring lumen 668 each connect with separate ports at or near the distal tip of the catheter 664, distal to the occlusion balloon 660. The catheter shaft 652 can be made in a range of sizes, for instance with an external diameter of 3.5 to 4 mm or 10.5 to 12 French (Charrière scale) for use with blood/cardioplegia techniques, or with an external diameter of 3.3 mm or 10 French (Charrière scale) or smaller for use with crystalloid cardioplegia techniques.

Figure 13:
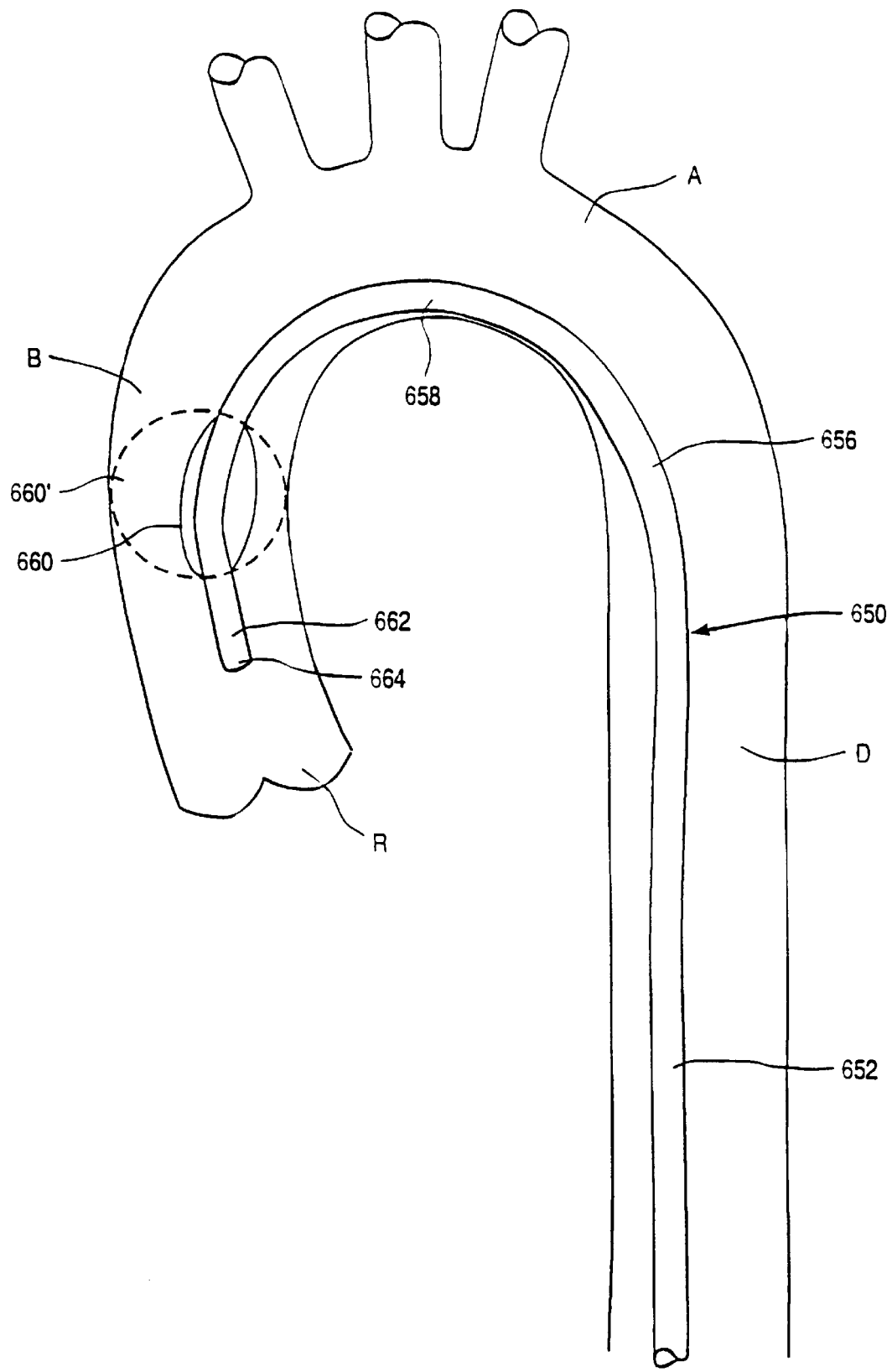
FIG. 13 is a schematic partly cut-away representation of a patient's aortic arch with the endoaortic partitioning catheter of FIG. 12A positioned in the ascending aorta.

FIG. 13 is a schematic partly cut-away representation of a patient's aortic arch A with the endoaortic partitioning catheter 650 of FIG. 12A positioned in the ascending aorta B. In use, a guidewire and a dilator (not shown) are inserted into the infusion lumen 666 to straighten out the distal curve 654 of the catheter 650. The catheter 650 is introduced into a peripheral arterial access site such as the femoral artery and advanced until the distal end 664 of the catheter 650 is at the apex of the aortic arch A. Then, the dilator is withdrawn as the catheter is advanced over the aortic arch A to allow the distal portion 652 of the catheter 650 to resume its curve within the ascending aorta B. When the catheter 650 is in proper position in the ascending aorta B, the second segment 658 of the curved shaft conforms to the aortic arch A to hold the distal tip 664 of the catheter centered just above the aortic root R. Due to its curvature, the second segment 658 of the catheter shaft tends to hug the inside curve of the aortic arch A which helps to prevent the catheter shaft from occluding or interfering with blood flow into the brachiocephalic artery or other arteries which have their takeoff from the aortic arch. The first curved segment 656 of the catheter shaft 652 resides in the descending aorta D, somewhat straightened by its contact with the aortic walls. The angled or spiral curve of the catheter shaft 652 assists in centering the distal tip 664 of the catheter 650 within the lumen of the ascending aorta B which is often angled anteriorly within the patient.

In order to reduce the external diameter of the catheter shaft in the embodiments of FIGS. 10A–10C and 12A–12C, particularly for use in conjunction with the dual purpose arterial cannula and introducer sheath described below in reference to FIGS. 31–34, while maintaining the maximum flow rate performance in the catheter, it is desirable to reduce the wall thickness of the multilumen extrusion as much as possible. In order to improve the kink resistance of the thin-walled catheter shaft in the precurved distal portion (604 in FIG. 10A, 654 in FIG. 12A) it has been found to be advantageous to dip coat the precurved distal portion with a soft, flexible polymer. For example a coating approximately 0.005–0.020 inches thick of a polyurethane with a hardness of 80 Shore A durometer on the precurved distal portion of the catheter shaft has been shown to significantly improve the kink resistance of the catheter shaft. If the coating is applied before mounting the polyurethane occlusion balloon on the catheter shaft, the coating also improves the heat bondability of the occlusion balloon to the shaft. Coating only the distal portion of the catheter shaft has the advantage that it does not increase the external diameter of the catheter shaft in the proximal portion which will reside within the blood flow lumen of the dual purpose arterial cannula and introducer sheath during perfusion. Since the proximal portion of the catheter shaft is not precurved and because it resides in the relatively straight descending aorta during use, it is not necessary to fortify the kink resistance of the shaft in this region.

One important function of the catheter curves shown in FIGS. 10A and 12A is for centering the tip of the catheter within the ascending aorta before and after the occlusion balloon is inflated to insure even distribution of the cardioplegic fluid to the coronary arteries when it is injected through the infusion lumen into the aortic root. In many cases, the compound curve of the catheter is needed to maintain the catheter tip within the center of the aortic lumen. It has been found that in some cases a simple 180° U-shaped curve results in off-center placement of the catheter tip despite the concentricity of the inflated balloon because of the curve of the ascending aorta. Another approach to centering the distal tip of the catheter within the lumen of the ascending is illustrated by the embodiment of the aortic partitioning catheter 700 shown in FIG. 14.

Figure 14:
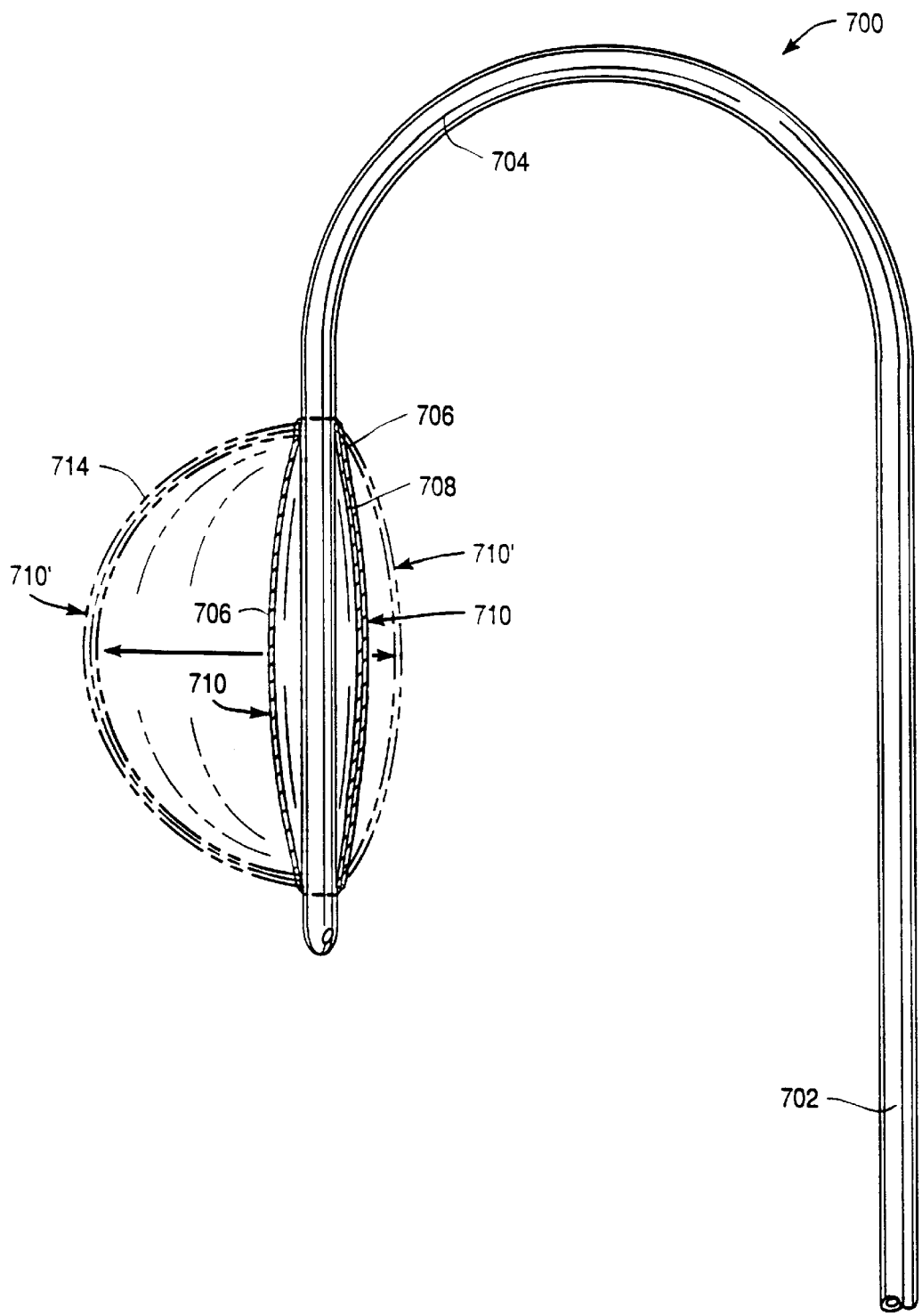
FIG. 14 is a front view of an eighth embodiment of the endoaortic partitioning catheter having an asymmetric aortic occlusion balloon.

FIG. 14 is a front view of an embodiment of the endoaortic partitioning catheter 700 having an eccentric aortic occlusion balloon 710. The occlusion balloon has a symmetrical deflated profile, shown by solid lines 710. The asymmetrical inflated profile, shown by phantom lines 710', is achieved by molding the occlusion balloon with a thicker wall 712 on one side of the balloon 710. The thicker wall 712 of the balloon is oriented toward the inside of the distal curve 704 when mounted on the catheter shaft 702. When the occlusion balloon 710' is inflated, the thicker wall 712 resists expansion while the thinner wall 714 of the balloon more easily expands to its full potential, resulting in the intended eccentric inflated balloon profile 710'. One preferred method for manufacturing the occlusion balloon 710 of FIG. 14 is by a two-stage dip molding process. In the first stage of the process, a balloon mold, in the form of a dipping mandrel having the desired interior shape of the balloon, is oriented vertically and dipped into a solution or a suspension containing an elastomeric balloon material, such as polyurethane, silicone or latex. This creates a relatively even coating of the balloon material over the surface of the mandrel. This first coating 706 is then allowed to dry on the mandrel. Once the first coating 706 is dry, the orientation of the dipping mandrel is rotated to a horizontal position and one side of the balloon mandrel is dipped into the elastomer solution to create a second coating 708 of balloon material on one side of the balloon 710. The balloon mandrel is held in the horizontal orientation until the solvent evaporates from the elastomer solution. If the elastomer used to mold the balloon 710 is a thermoplastic elastomer, such as a thermoplastic polyurethane, the balloon can be removed from the dipping mandrel once it has dried. If the elastomer is a thermoset material, such as latex, silicone, or a thermoset polyurethane, further curing of the material may be required before the balloon 710 can be removed from the dipping mandrel. It should be noted that the second coating 708 on the balloon 710 may be made of a different material from the first coating 706. For instance, a stronger or less distensible material may be used for the second coating 708 to increase the resistance of the thicker wall 712 of the balloon 710 to inflation. It should also be noted that molding each coating of the balloon may require multiple iterations of the dipping and drying steps, depending on the composition and concentration of the polymer solution. For example, the currently preferred process for manufacturing polyurethane balloons typically requires about 6–8 iterations of the dipping and drying steps to make a finished balloon with a wall thickness of approximately 0.005–0.020 inches.

Figure 16:
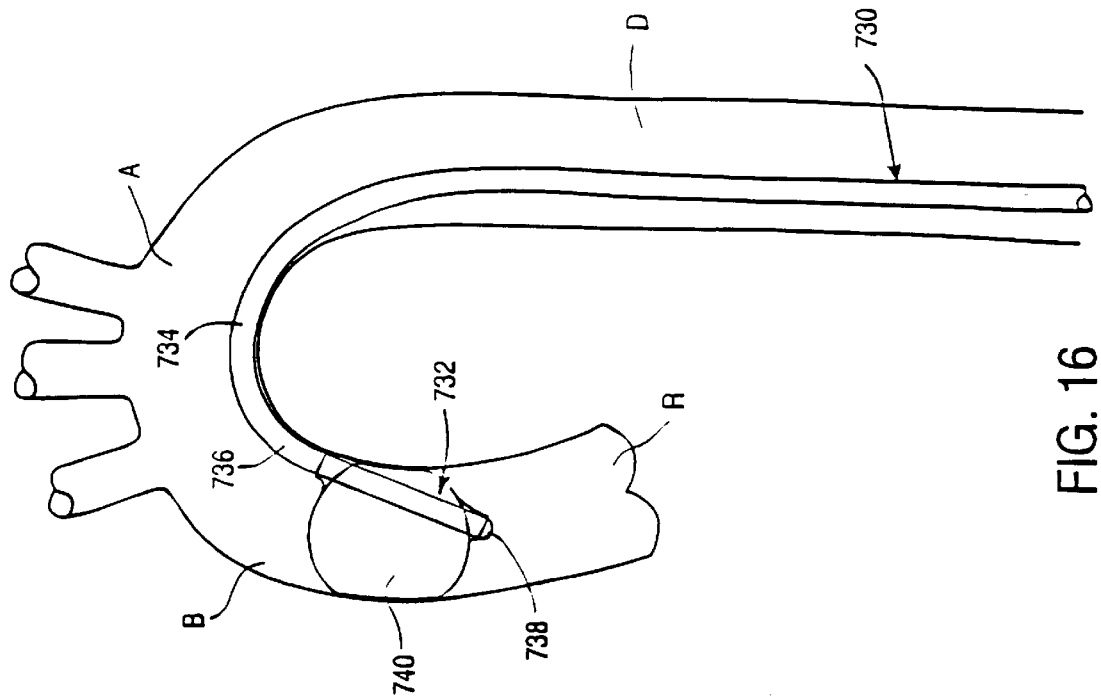
FIG. 16 is a schematic partly cut-away representation of a patient's aortic arch with an endoaortic partitioning catheter having an eccentric occlusion balloon positioned in the ascending aorta.
Figure 15:
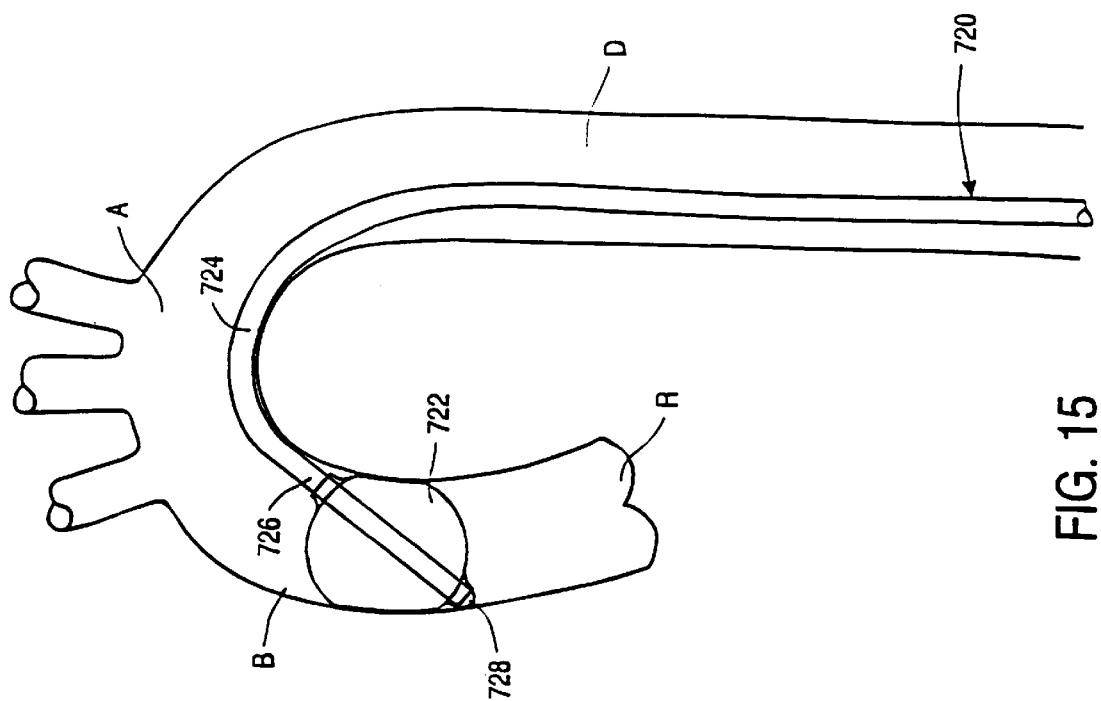
FIG. 15 is a schematic partly cut-away representation of a patient's aortic arch with an endoaortic partitioning catheter having a concentric occlusion balloon positioned in the ascending aorta.

FIGS. 15 and 16 illustrate how an eccentric balloon, like the eccentric occlusion balloon 710 of the catheter embodiment of FIG. 14, operates to center the tip of the aortic partitioning catheter within the ascending aorta of a patient. FIG. 15 is a schematic partly cut-away representation of a patient's aortic arch A with an endoaortic partitioning catheter 720 having a concentric occlusion balloon 722 positioned in the ascending aorta B. The endoaortic partitioning catheter 720 has a 180° U-shaped catheter curve 724 with a concentric occlusion balloon 722 mounted on a straight distal portion 726 of the catheter 720. FIG. 15 shows the effect of placing the U-shaped catheter curve into a patient having a curved ascending aorta B. Note how, when the catheter 720 is pulled proximally to stabilize the catheter within the aortic arch A, the distal end 728 of the catheter is not centered in the aortic lumen despite the concentricity of the balloon 722 because of the mismatch between the catheter curve and the curve of the ascending aorta B.

FIG. 16 is a schematic partly cut-away representation of a patient's aortic arch A with an endoaortic partitioning catheter 730 having an eccentric occlusion balloon 732 positioned in the ascending aorta B. The aortic partitioning catheter 730 has a U-shaped distal curve 734 which subtends an arc of approximately 180°+/−45°. Mounted on a straight distal portion 736 of the catheter shaft is an occlusion balloon 732 which, when inflated, has an eccentric balloon profile with the larger portion 740 of the balloon facing the outside of the catheter curve 734 so that it will be oriented toward the right side of the patient. The eccentric inflated profile of the balloon 732 assists in centering the distal tip 738 of the catheter 730 within the aortic lumen when the ascending aorta B is curved. Note how the eccentric balloon 732 compensates for the mismatch between the catheter curve and the curve of the ascending aorta B to result in the distal tip 738 of the catheter 730 being well centered in the aortic lumen just above the aortic root R.

Figure 17:
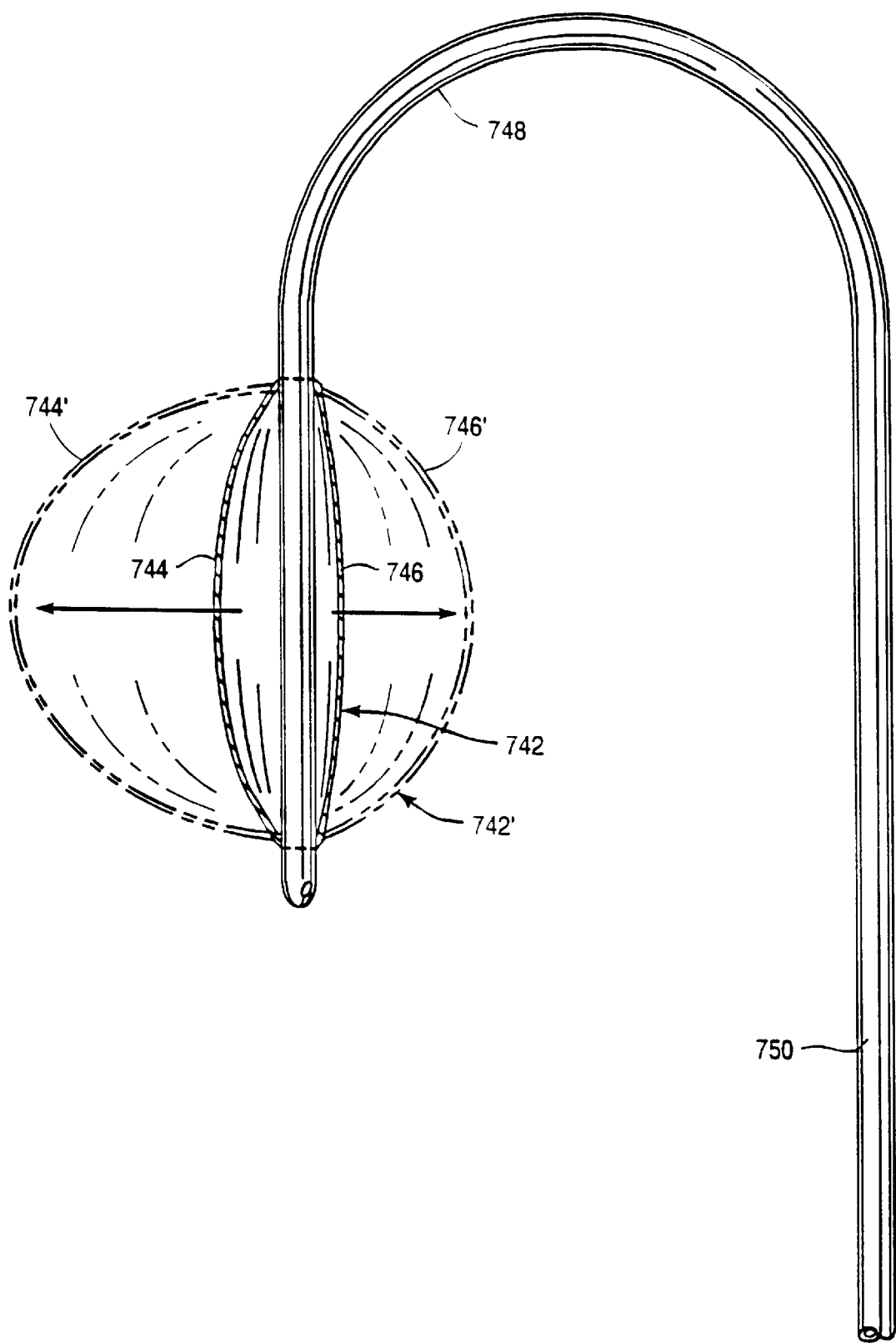
FIG. 17 is a front view of an ninth embodiment of the endoaortic partitioning catheter having an eccentric aortic occlusion balloon.

FIG. 17 shows an alternative construction for an occlusion balloon 742 with an eccentric inflated profile 742'. In this embodiment, the elastomeric balloon 742 is molded on a dipping mandrel which is machined with an asymmetrical profile. In contrast to the previous example, the molded balloon 742 has a uniform wall thickness, but it has an asymmetrical deflated profile with a larger side 744 and a smaller side 746. The balloon 742 is mounted on the catheter with the larger side 744 oriented toward the outside of the distal curve 748 of the catheter 750. When inflated, the larger side 744 of the balloon expands to a greater radius 744' than the smaller side 746', giving the intended eccentric inflated profile, as shown by phantom lines 742'.

Figures 18A, 18B:
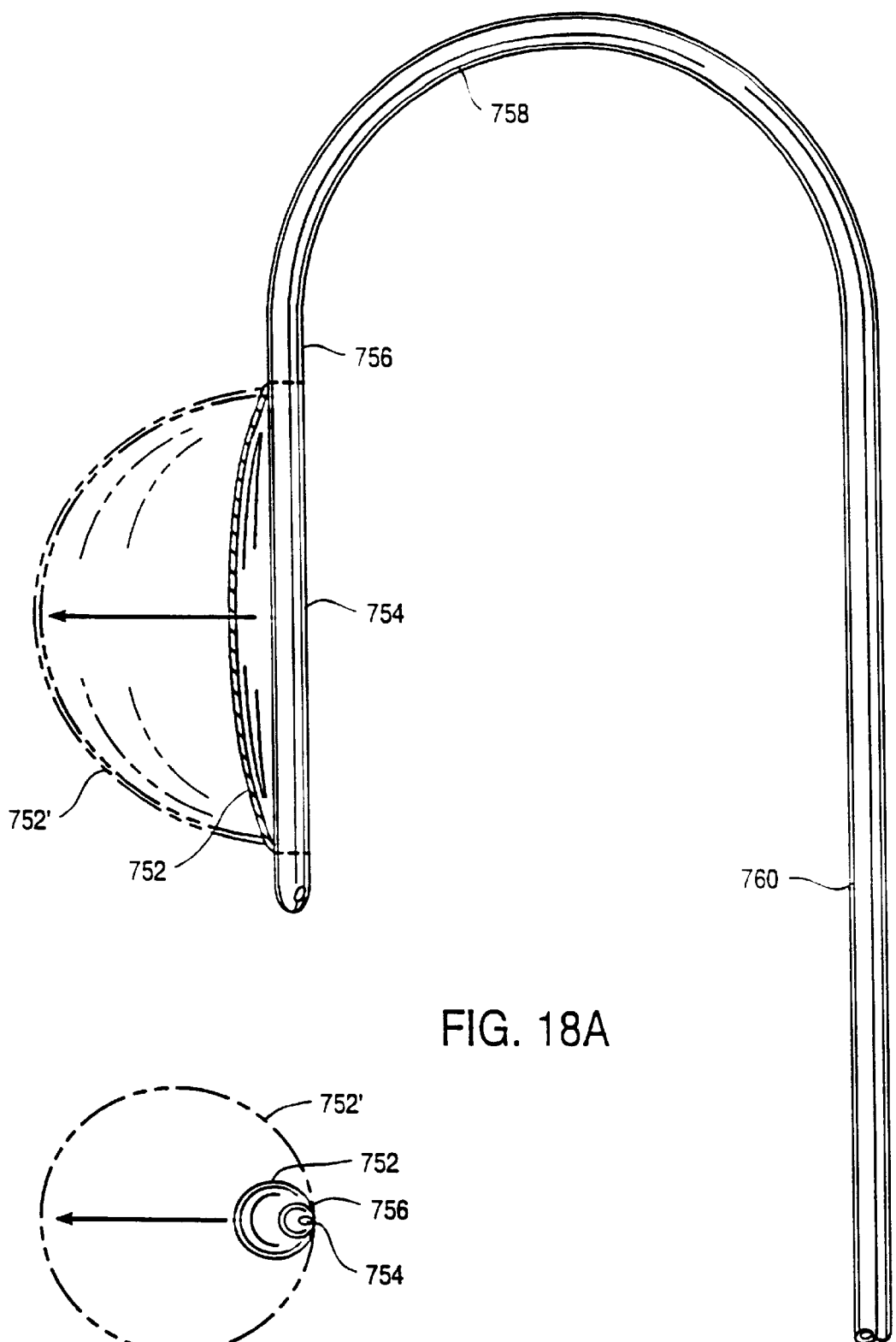
FIG. 18A is a front view of a tenth embodiment of the endoaortic partitioning catheter having an eccentric aortic occlusion balloon.
FIG. 18B is an end view of the catheter of FIG. 18A.

FIGS. 18A and 18B show another alternative construction for an occlusion balloon 752 with an eccentric inflated profile 752'. In this embodiment, the elastomeric occlusion balloon 752 is mounted on the catheter 760 in such a way that the side 754 of the balloon oriented toward the inside of the distal curve 758 of the catheter is bonded directly to the catheter shaft 756 along the length of the balloon 752 using a suitable adhesive. When the occlusion balloon 752 is inflated, only the side of the balloon oriented toward the outside of the distal curve 758 of the catheter shaft is allowed to expand, creating an eccentric inflated balloon profile, as shown by phantom lines 752'.

FIGS. 19A–19D and 20A–20D show alternative constructions of an eccentric occlusion balloon made of a nondistensible balloon material, such as polyethylene, polyethylene terephthalate polyester, polyester copolymers, polyamide or polyamide copolymers. Using a nondistensible balloon material such as these allows more precise control over the final shape and dimensions of the inflated occlusion balloon, as compared to the elastomeric balloons previously described. The nondistensible balloons can be thermoformed from tubing extruded from a nonelastomeric polymer, using known methods. Alternatively, the balloons can be dipped or rotomolded of a nonelastomeric polymer in solution. It is presently preferred to mold the inelastic balloon material using a hollow or negative mold of the exterior inflated balloon shape rather than a positive mold of the interior shape as used for the elastomeric balloons, because the molded inelastic balloons may be difficult to remove from a positive mold.

FIGS. 19A–19D show a first example of a nondistensible eccentric occlusion balloon 762. FIG. 19A shows a side view of the occlusion balloon in the deflated state 762 and inflated state 762'. FIG. 19B shows an end view of the same occlusion balloon in the deflated 762 and inflated states 762'. The occlusion balloon 762 is molded in an asymmetrical shape with a large side 764 and a smaller side 766. The occlusion balloon 762 is mounted on the catheter shaft 768 with the larger side 764 oriented toward the outside of the distal curve of the catheter. The occlusion balloon tends to flatten out, as shown by solid lines 762, when it is deflated. In order to reduce the deflated profile of the balloon for introduction into a peripheral artery, the flattened balloon 762" is wrapped around the catheter shaft 768 as shown in a side view in FIG. 19C and an end view in FIG. 19D.

Figures 20A, 20C:
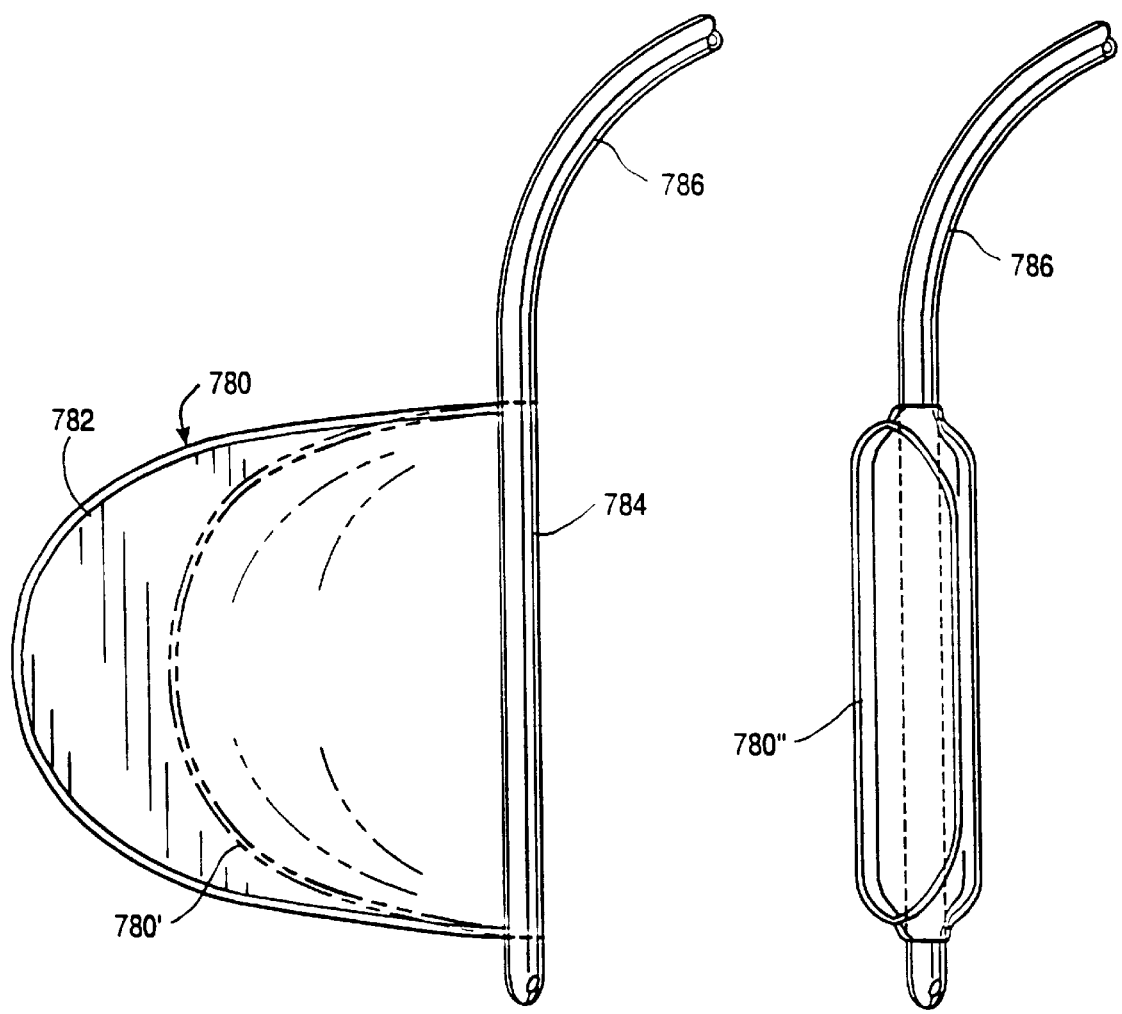
FIG. 20A is a front view of a twelfth embodiment of the endoaortic partitioning catheter having a nondistensible aortic occlusion balloon.
FIG. 20C is a side view of the catheter of FIG. 20A with the occlusion balloon wrapped around the catheter shaft.
Figures 20B, 20D:
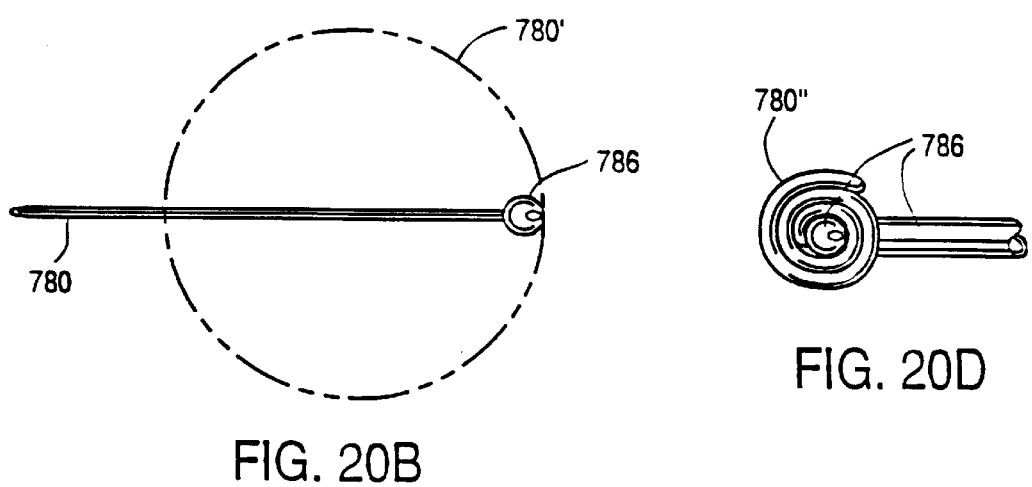
FIG. 20B is an end view of the catheter of FIG. 20A.
FIG. 20D is an end view of the catheter of FIG. 20C.

FIGS. 20A–20D show a second example of a nondistensible eccentric occlusion balloon 780. FIG. 20A shows a side view of the occlusion balloon in the deflated state 780 and inflated state 780'. FIG. 20B shows an end view of the same occlusion balloon in the deflated state 780 and inflated state 780'. The occlusion balloon 780 is molded in an asymmetrical shape with a large side 782 and a smaller side 784. The occlusion balloon 780 is mounted on the catheter shaft 786 with the larger side 782 oriented toward the outside of the distal curve of the catheter. In this embodiment, the smaller side 784 of the occlusion balloon is adhesively bonded to the catheter shaft 786 along the length of the balloon 780 so that the inflated balloon 780' expands only toward the outside of the distal curve of the catheter. The occlusion balloon flattens out, as shown by solid lines 780, when it is deflated. In order to reduce the deflated profile of the balloon for introduction into an artery, the flattened balloon 780" is wrapped around the catheter shaft as shown in a side view in FIG. 20C and an end view in FIG. 20D.

The eccentrically shaped occlusion balloons of FIGS. 14 and 16–20 serve to help center the distal tip of the aortic partitioning catheter within the ascending aorta for uniform distribution of cardioplegic fluid injected through the infusion lumen and for aligning the tip of the catheter with the center of the aortic valve when other instruments are introduced through the infusion lumen. The degree of concentricity of the occlusion balloon can be varied from perfectly concentric to completely eccentric, or one-sided, using the embodiments and methods described in connection with FIGS. 14 and 16–20. Specially shaped occlusion balloons can also be used with the aortic partitioning catheter of the present invention for maximizing the working space within the ascending aorta between the aortic valve and the occlusion balloon. This aspect of the invention will be of particular significance when the catheter system is used for arresting the heart so that surgery or other interventional procedures can be performed on the patient's aortic valve. Whether the aortic valve surgery is performed by thoracoscopic methods, endovascular methods or open chest surgical methods, it will be beneficial to be able to occlude the ascending aorta as required for establishing cardiopulmonary bypass without obstructing surgical access to the aortic valve. This aspect of the invention will also find particular utility when performing port-access coronary artery bypass grafting (CABG) surgery with a saphenous vein bypass graft or other free graft which must be anastomosed to the ascending aorta because the occlusion balloon will not interfere with the anastomosis procedure. FIGS. 21–24 show four variations of specially shaped balloons developed for this purpose. These balloons can be manufactured from elastomeric materials or from nondistensible, inelastic materials as previously described.

Figure 21:
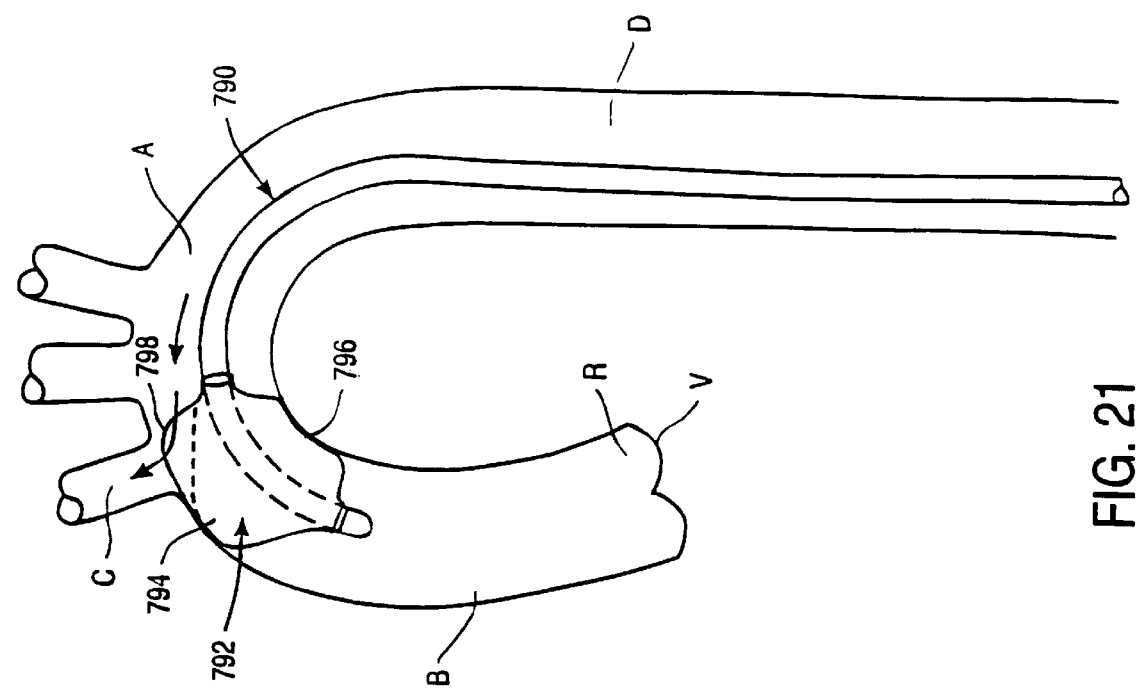
FIG. 21 is a schematic partly cut-away representation of a patient's aortic arch with an endoaortic partitioning catheter having a shaped occlusion balloon positioned in the ascending aorta.

FIG. 21 is a schematic partly cut-away representation of a patient's aortic arch A with a first variation of an endoaortic partitioning catheter 790 having a shaped occlusion balloon 792 positioned in the ascending aorta B. The occlusion balloon 792 has a generally cylindrical outer geometry that has been modified by curving it to match the curvature of the aortic arch A. Thus, the surface of the occlusion balloon facing the outside curve of the aortic arch A has a convex curvature 794 to match the concave curvature of the aortic wall at that point and the surface of the occlusion balloon facing the inside curve of the aortic arch A has a concave curvature 796 to match the convex curvature of the opposite aortic wall. The geometry of the occlusion balloon 792 is further modified by molding a groove or indentation 798 into the proximal edge of the convexly curved outer surface 794 of the balloon 792. The indentation 798 is positioned to allow blood flow past the occlusion balloon 792 into the brachiocephalic artery C. This allows the occlusion balloon 792 of the aortic partitioning catheter 790 to be placed as far downstream in the ascending aorta as possible without occluding flow to the brachiocephalic artery C from the cardiopulmonary bypass system. The working space between the aortic valve V and the occlusion balloon 792 is maximized to allow maneuvering of surgical instruments, interventional catheters or a valve prosthesis within the ascending aorta B. Although it does not serve to occlude the aortic lumen, the proximal portion of the occlusion balloon 792 contacts the aortic wall and helps to stabilize the inflated balloon within the aorta to keep the distal end of the catheter centered and to help prevent unintended displacement of the inflated balloon.

Figure 22:
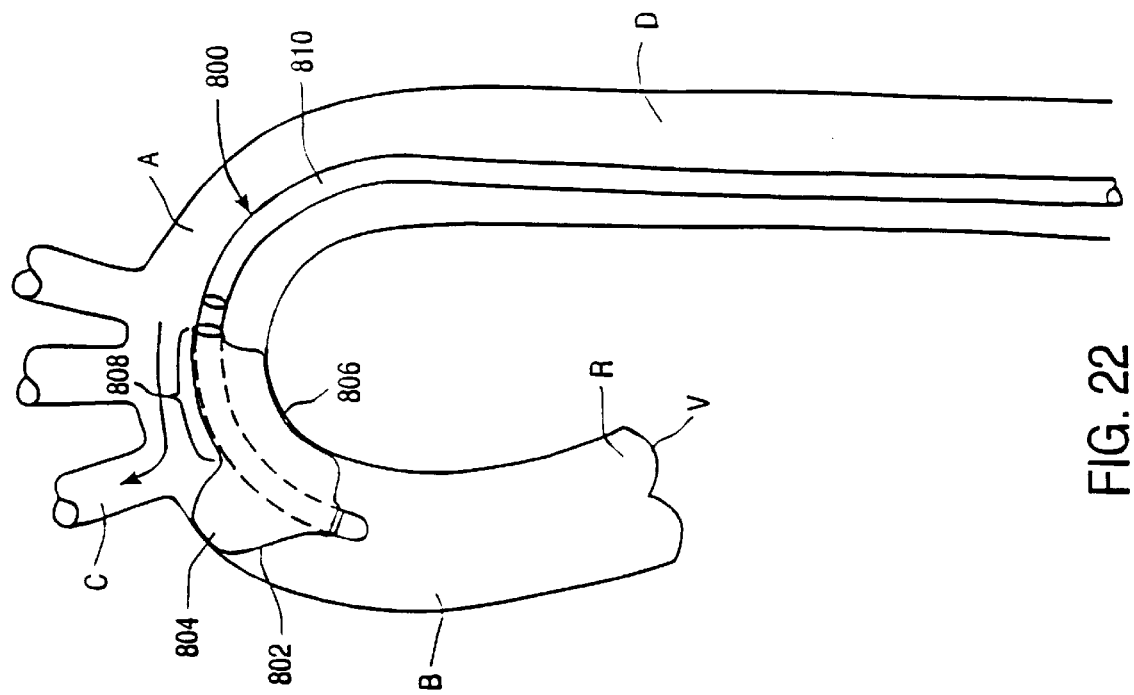
FIG. 22 is a schematic partly cut-away representation of a patient's aortic arch with an endoaortic partitioning catheter having a shaped occlusion balloon positioned in the ascending aorta.

FIG. 22 is a schematic partly cut-away representation of a patient's aortic arch A with a second variation of an endoaortic partitioning catheter 800 having a shaped occlusion balloon 802 positioned in the ascending aorta B. As in the previous example, the occlusion balloon 802 has a generally cylindrical outer geometry that has been modified by curving it to match the curvature of the aortic arch A. The surface of the occlusion balloon facing the outside curve of the aortic arch A has a convex curvature 804 to match the concave outer curvature of the aortic wall and the surface of the occlusion balloon facing the inside curve of the aortic arch A has a concave curvature 806 to match the convex inner curvature of the opposite aortic wall. The geometry of the occlusion balloon 802 is further modified by molding a large ramp-shaped indentation 808 into the proximal side of the convexly curved outer surface 804 of the balloon 802. The wall of the occlusion balloon 802 can be adhesively attached to the catheter shaft 810 along the length of the ramp-shaped indentation 808 to help maintain the geometry of the balloon when subjected to inflation pressure. The ramp-shaped indentation 808 is positioned to allow blood flow past the occlusion balloon 802 into the brachiocephalic artery C. This allows the occlusion balloon 802 of the aortic partitioning catheter 800 to be placed as far downstream in the ascending aorta as possible without occluding flow to the brachiocephalic artery C in order to maximize the working space between the aortic valve V and the occlusion balloon 802. The broad ramp-shaped indentation 808 in the occlusion balloon 802 lessens the need for careful placement of the occlusion balloon 802 with respect to the brachiocephalic artery C without danger of occluding it. The concavely curved inner surface 806 of the occlusion balloon 802 provides an extended contact surface with the wall of the aortic arch A to stabilize the inflated occlusion balloon 802 and to discourage unintended movement or dislodgement of the occlusion balloon 802. As in the previous embodiment, the proximal portion of the occlusion balloon 802 contacts the aortic wall and helps to stabilize the inflated balloon within the aorta to keep the distal end of the catheter centered and to help prevent unintended displacement of the inflated balloon.

Figure 23A:
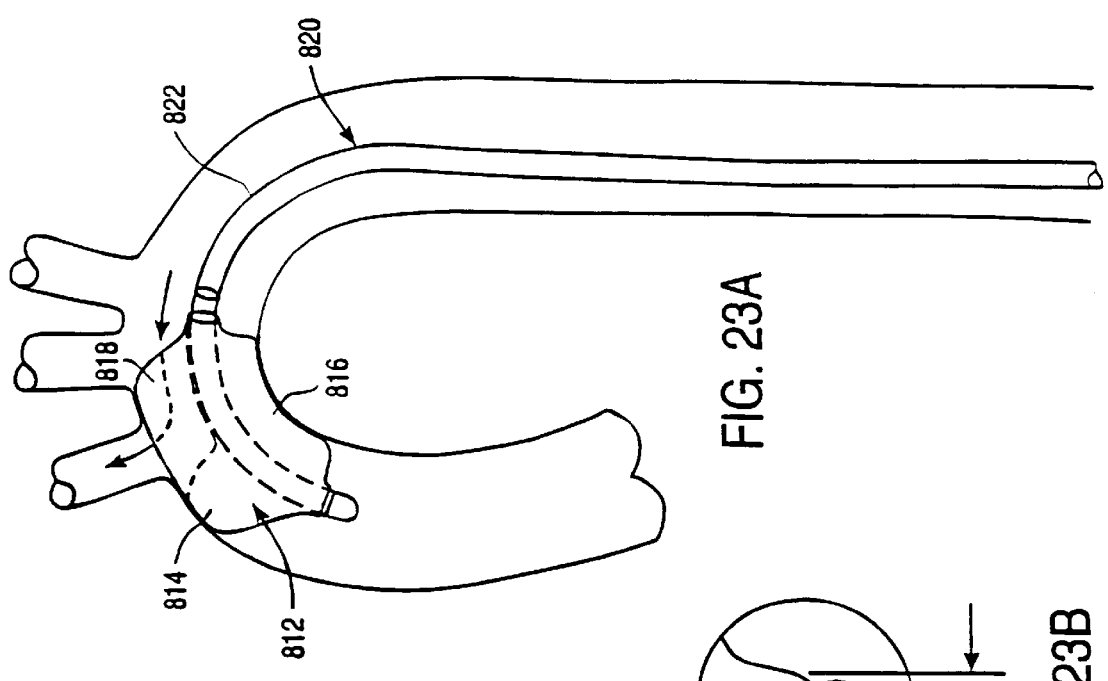
FIG. 23A is a schematic partly cut-away representation of a patient's aortic arch with an endoaortic partitioning catheter having a shaped occlusion balloon positioned in the ascending aorta.
Figure 23B:
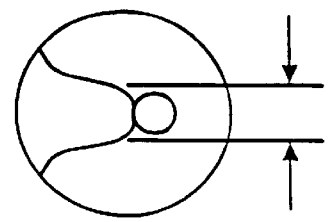
FIG. 23B is a transverse cross section of the shaped occlusion balloon of FIG. 23A.

FIG. 23A is a schematic partly cut-away representation of a patient's aortic arch A with a third variation of an endoaortic partitioning catheter 820 having a shaped occlusion balloon 812 positioned in the ascending aorta B. FIG. 23B is a transverse cross section of the shaped occlusion balloon of FIG. 23A. This occlusion balloon 812 also has a generally cylindrical outer geometry that has been modified by curving it to match the curvature of the aortic arch A. The surface of the occlusion balloon facing the outside curve of the aortic arch A has a convex curvature 814 to match the concave outer curvature of the aortic wall and the surface of the occlusion balloon facing the inside curve of the aortic arch A has a concave curvature 816 to match the convex inner curvature of the opposite aortic wall. The geometry of the occlusion balloon 812 is further modified by molding an extended groove or invagination 818 into the proximal side of the convexly curved outer surface 814 of the balloon 812. The extended groove 818 should have a width at least as wide as the ostium of the brachiocephalic artery C. The wall of the occlusion balloon 812 can be adhesively attached to the catheter shaft 822 along the length of the extended groove 818 to help maintain the geometry of the balloon when subjected to inflation pressure. The extended groove 818 is positioned to allow blood flow past the occlusion balloon 812 into the brachiocephalic artery C. This allows the occlusion balloon 812 of the aortic partitioning catheter 800 to be placed even farther downstream in the ascending aorta without occluding flow to the brachiocephalic artery C in order to maximize the working space between the aortic valve V and the occlusion balloon 812. Again, the concavely curved inner surface 816 of the occlusion balloon 812 provides an extended contact surface with the wall of the aortic arch A to stabilize the inflated occlusion balloon 812 and to discourage unintended movement or dislodgement of the occlusion balloon 812.

Figure 24:
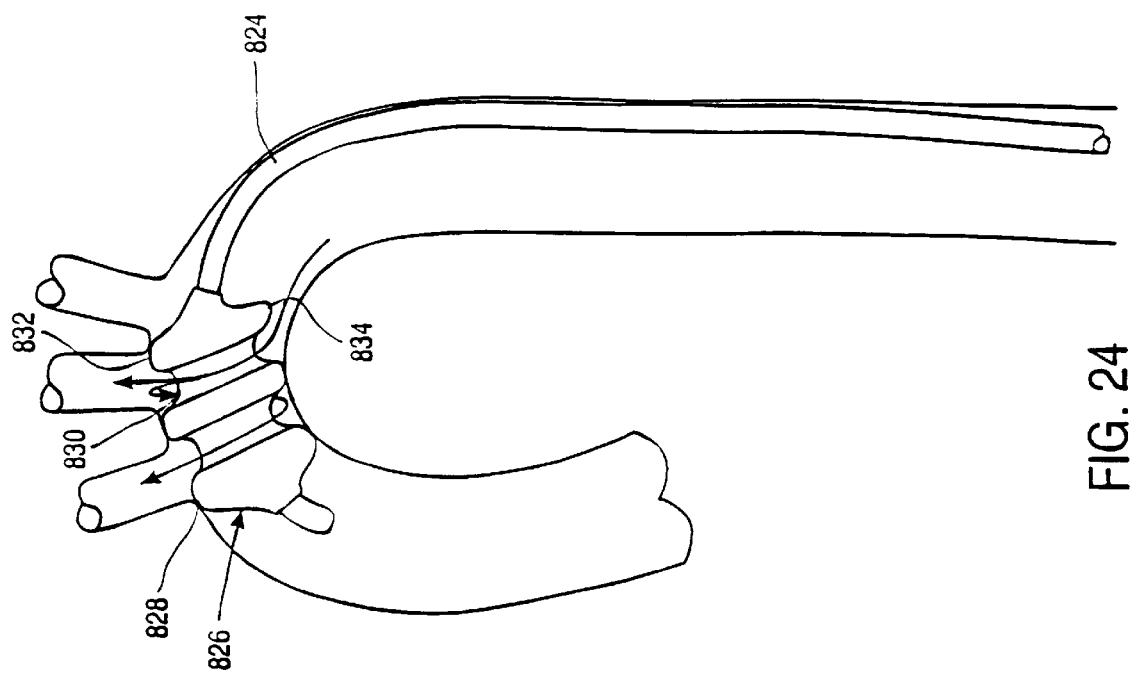
FIG. 24 is a schematic partly cut-away representation of a patient's aortic arch with an endoaortic partitioning catheter having a shaped occlusion balloon positioned at the apex of the aortic arch.

FIG. 24 is a schematic partly cut-away representation of a patient's aortic arch A with a fourth variation of an endoaortic partitioning catheter 824 having a shaped occlusion balloon 826 positioned at the apex of the aortic arch A. In an effort to further maximize the working space between the aortic valve V and the occlusion balloon 826 the geometry of the occlusion balloon 826 has been modified so that it can be placed at the very apex of the aortic arch A without compromising blood flow to the brachiocephalic, common carotid or subclavian arteries. The occlusion balloon 826 has a generally cylindrical outer geometry modified with a helical groove 830 that starts at the proximal end 834 of the balloon and spirals around the balloon 826 in the distal direction. In this illustrative embodiment, the spiral groove 830 forms approximately two complete turns encircling the occlusion balloon 826 and is delimited by an annular ring 828 that forms a seal with the aortic wall at the distal end of the balloon 826 to isolate the heart and the coronary arteries the systemic blood flow which is supported by the cardiopulmonary bypass system. The spiral groove 830 forms a flow path for oxygenated blood from the descending aorta to the brachiocephalic, common carotid or subclavian arteries C. A spiral ridge 832 that runs along the spiral groove 830 contacts the aortic wall and stabilizes the inflated occlusion balloon 826 to prevent unintended movement of the occlusion balloon 812 without occluding blood flow to the head and neck arteries. This same effect can be accomplished using functionally equivalent balloon geometries. For instance, this effect could be achieved with a shaped balloon having an annular ring at the distal end of the balloon to seal against the aortic wall, isolating the heart and the coronary arteries from systemic blood flow, and a multiplicity of bumps or ridges at the proximal end to contact the aortic wall and stabilize the balloon, with the space between the bumps providing a blood flow path to the head and neck arteries branching from the aortic arch.

Figure 25A:
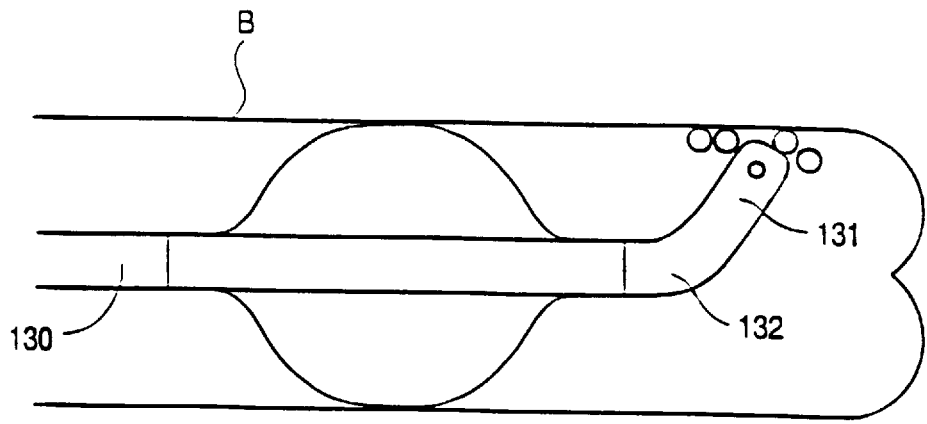
FIG. 25A illustrates an endoaortic partitioning catheter with a curved tip for de-airing the heart and ascending aorta.
Figure 25B:
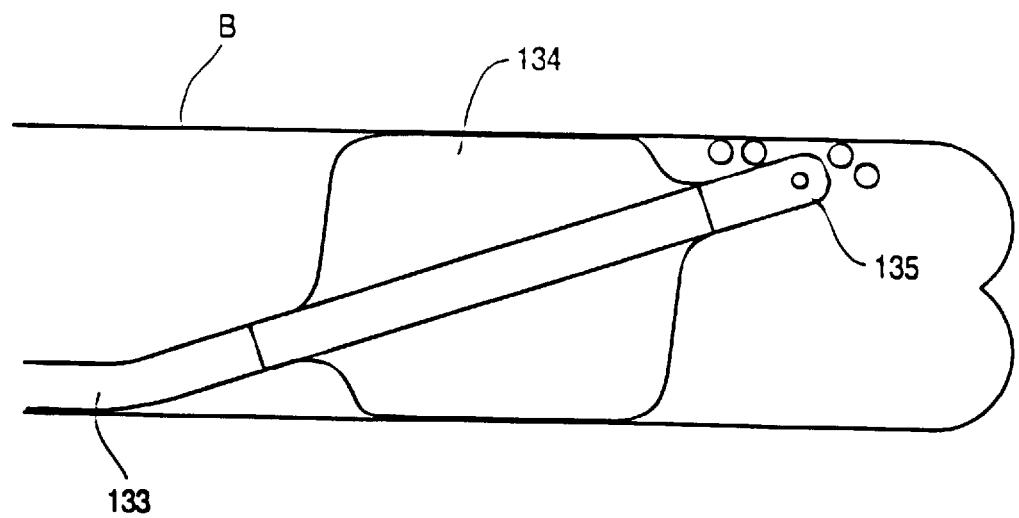
FIG. 25B illustrates an alternate embodiment of an endoaortic partitioning catheter for de-airing the heart and ascending aorta.

Another aspect of the present invention is illustrated in FIGS. 25A and 25B. In this embodiment, the function of de-airing the heart and the ascending aorta at the completion of the interventional procedure has been combined with the endoaortic partitioning catheter 130. The catheter 130 is configured so that the distal tip 131 of the catheter is positioned near the anterior wall of the ascending aorta B. This can be accomplished by making a curve 132 in the distal portion of the catheter shaft that brings the tip 131 of the catheter near the anterior wall of the ascending aorta B, as shown in FIG. 25A. Alternatively, the occlusion balloon 134 can be shaped so that when the balloon 134 is inflated, the distal tip 135 of the catheter 133 is directed toward the anterior wall of the ascending aorta B, as shown in FIG. 25B. The advantage of this modification of the endoaortic partitioning catheter is that, when the patient is placed in a supine position, the distal tip of the catheter is at the highest point in the ascending aorta so that any air bubbles that enter the heart, the coronary arteries or the aortic root during the course of surgery can be vented out through a lumen in the catheter prior to deflating the occlusion balloon to reverse the cardioplegic arrest.

Figure 26:
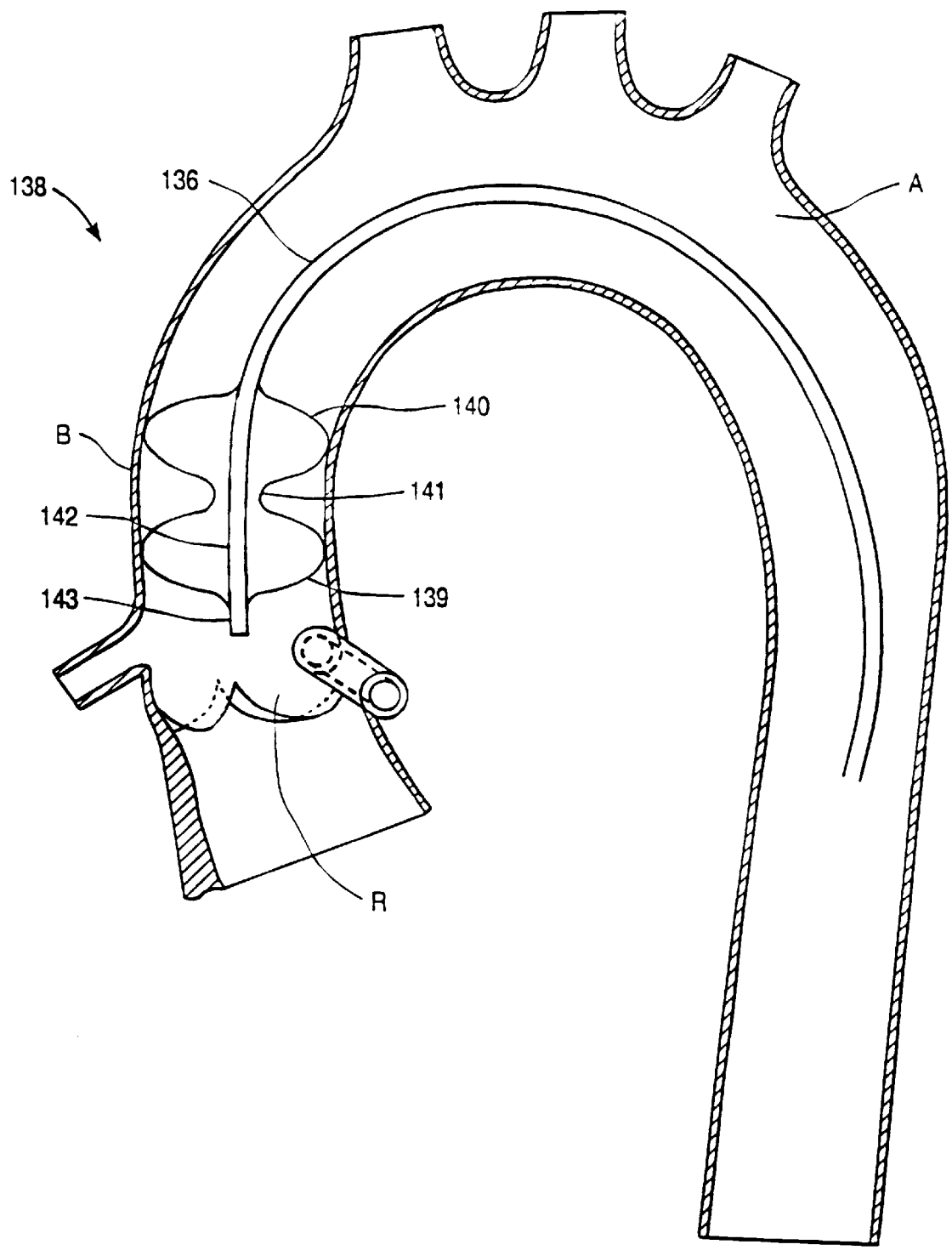
FIG. 26 illustrates an endoaortic partitioning catheter having a dumbbell-shaped occlusion balloon for centering the catheter tip within the ascending aorta.

FIG. 26 shows another application of shaped balloons for the purpose of centering the tip 137 of the endoaortic partitioning catheter 136 within the ascending aorta B. The expandable occlusion balloon 138 has a distal occlusion means 139 with an expanded diameter sufficient to occlude the ascending aorta B and a proximal stabilizing means 140 with an expanded diameter sufficient to contact the inner surface of the ascending aorta B. Between the occlusion means 139 and the stabilizing means 140 is an area of reduced diameter 141. When expanded, the occlusion means 139 blocks substantially all systolic and diastolic blood flow through the ascending aorta B. The stabilizing means 140 contacts the inner surface of the ascending aorta B and orients the distal segment 142 of the catheter shaft so that it is parallel with the axis of the ascending aorta B, reliably centering the catheter tip 143 within the aortic lumen just superior to the aortic root R.

One particular embodiment for achieving this geometry is shown in FIG. 26. In this embodiment, the occlusion balloon 138 has a dumbbell shape when expanded. The occlusion means is provided by a distal lobe 139 of the dumbbell shaped balloon 138, and the stabilizing means is provided by a proximal lobe 140 of the balloon, with a waist 141 of reduced diameter between the proximal 140 and distal 139 lobes. The dumbbell shaped occlusion balloon 138 thus has two rings of contact with the inner surface of the ascending aorta B for better stabilization and orientation of the balloon in the proper position. Additional advantages of this configuration are that by providing two rings of contact with the inner surface of the ascending aorta B, the dumbbell shaped balloon 138 can achieve a better and more reliable seal and greater resistance to displacement of the inflated balloon.

Another particular embodiment for achieving a similar geometry would have two separate, but closely spaced, expandable balloons mounted on the distal segment of the catheter shaft. When expanded, the more distal balloon serves as an occlusion means, and the more proximal balloon serves as a stabilizing means for orienting the distal segment of the catheter parallel to the axis of the aortic lumen. It should be noted that the stabilizing means need not occlude the ascending aorta. However, for proper effect, it should contact the inner surface of the ascending aorta at least three points around the inner circumference of the ascending aorta. Thus, the stabilizing means may have other non-spherical geometries that do not fully occlude the ascending aorta. For instance, multiple smaller balloons could be mounted circumferentially around the catheter shaft so that, when the balloons are inflated, they contact the inner surface of the ascending aorta at least three points. Likewise, an expandable, non-balloon stabilizing means can also be used for contacting the inner surface of the ascending aorta for stabilizing and orienting the distal tip of the catheter.

Figure 27:
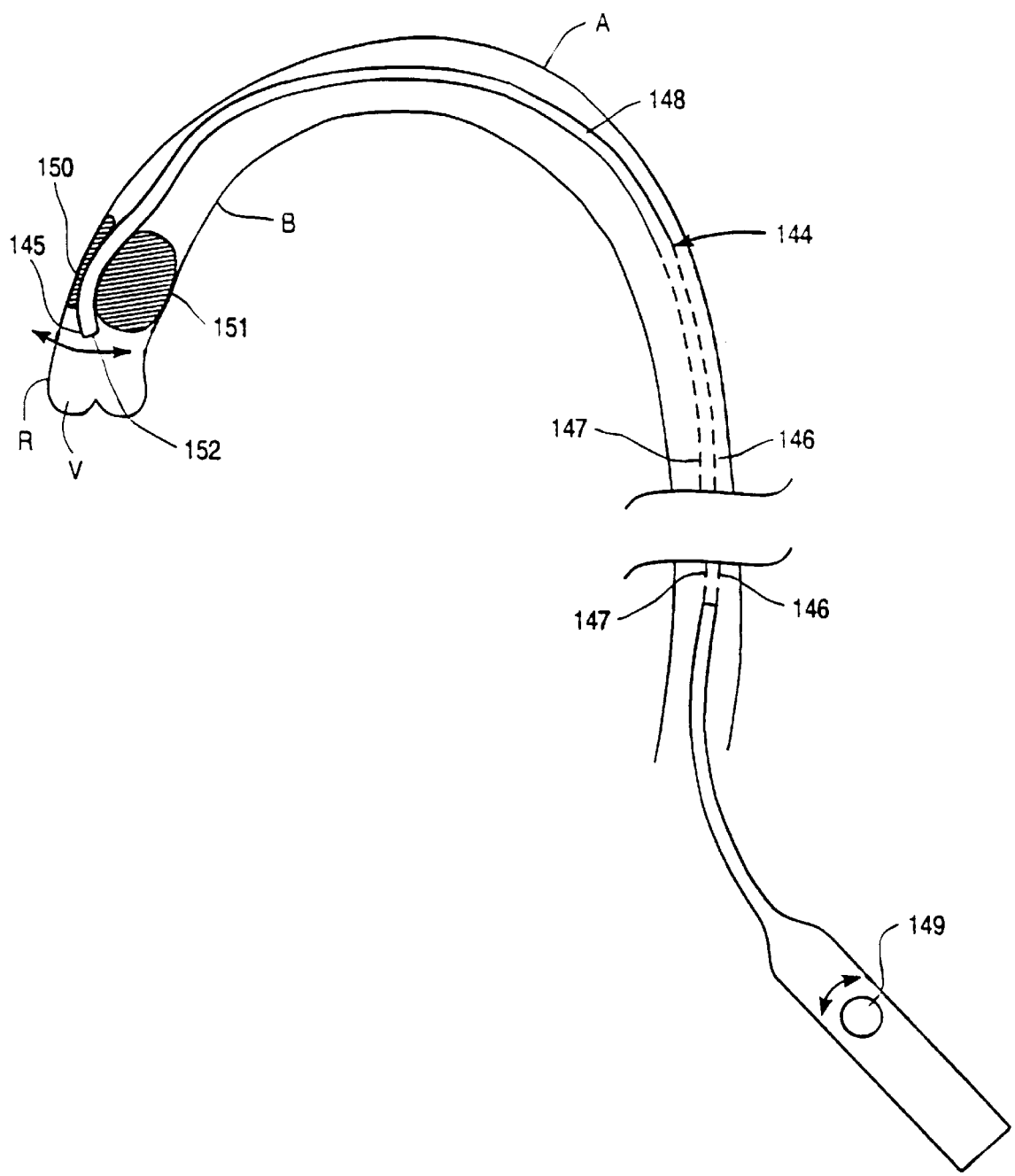
FIG. 27 illustrates an endoaortic partitioning catheter having a steerable distal tip for centering the catheter tip within the ascending aorta.

Another approach to centering the distal tip of the endoaortic partitioning catheter within the ascending aorta, shown in FIG. 27, works independently of balloon geometry. In this embodiment, the distal tip 145 of the endoaortic partitioning catheter 144 is made steerable by one or more control wires 146, 147 extending from the proximal end of the catheter 144 to the distal end through one or more lumens in the side wall of the catheter shaft 148. The distal end of the control wires 146, 147 connect to a rigid ring or other anchoring device embedded in the wall of the catheter shaft 148 near the distal tip 145 of the catheter 144. The proximal end of the control wires 146, 147 connect to a control means 149 at the proximal end of the catheter. For catheters 144 having one degree of freedom (i.e. 1–2 control wires) in the steerability of the distal tip 145, the control means 149 can be a control knob or lever or similar control device. For catheters 144 having two degrees of freedom (i.e. 4 or more control wires) in the steerability of the distal tip 145, the control means 149 can be a joy stick or similar control device. The shaft 148 of the catheter should be made with a flexible distal segment 150 which is relatively more flexible than the proximal portion of the catheter shaft 148. This concentrates the deflection of the catheter shaft in the distal section 150 when one or more of the control wires 146, 147 are tensioned by the control means 149 to steer the distal tip 145 of the catheter 144.

The steering mechanism can be used to deflect the distal tip 145 of the catheter shaft away from the aortic wall as the catheter is advanced through the aortic arch A and into the ascending aorta B. This reduces the likelihood of any trauma caused to the aortic wall by the catheterization and reduces the chances of dislodging any calcifications or other emboli from the aortic wall as the catheter 144 passes. Once the catheter 144 is in place in the ascending aorta B and the occlusion balloon 151 is inflated, the position of the catheter tip 145 can be verified fluoroscopically and the steering mechanism used to direct the tip 145 of the catheter toward the center of the aortic lumen in spite of any curvature in the ascending aorta B or eccentricities in the occlusion balloon 151. If any diagnostic or therapeutic instruments are to be delivered through the inner lumen 152 of the endoaortic partitioning catheter 144 the steering mechanism can be used for centering the distal tip 145 of the catheter 144 with respect to the aortic valve V or for directing the instruments to other anatomical features within the heart or the aortic root R. The steering mechanism can also be used for directing the catheter tip 145 toward the anterior wall or the highest point in the ascending aorta for de-airing the heart and the ascending aorta at the completion of the interventional procedure before deflating the occlusion balloon to reverse the cardioplegic arrest, as described above in relation to FIG. 25.

Figure 28:
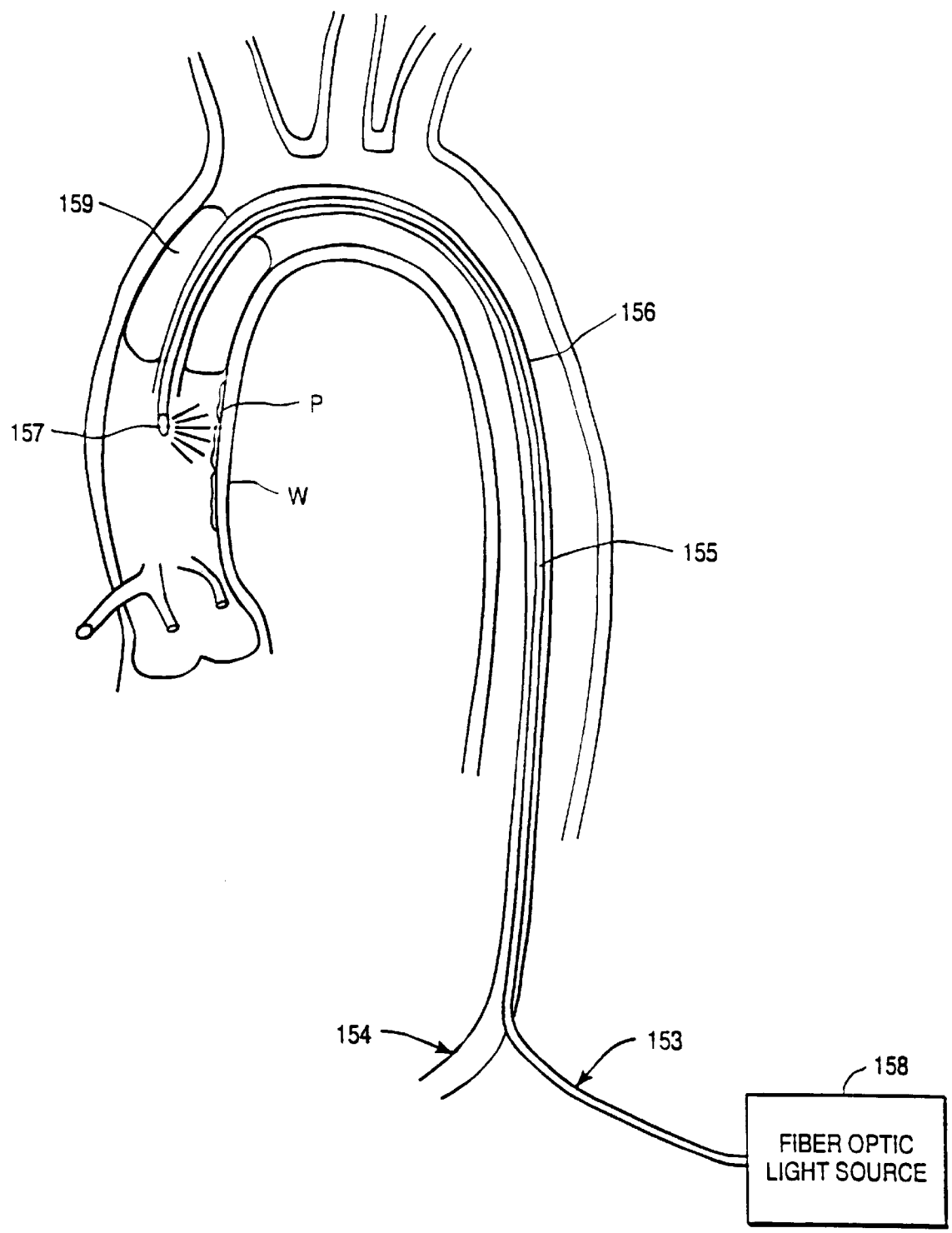
FIG. 28 illustrates an endoaortic partitioning catheter including a fiberoptic bundle for transillumination of the aortic wall and/or for facilitating non-fluoroscopic placement of the catheter.

Another aspect of the present invention is illustrated in FIG. 28. In this embodiment, a fiberoptic illumination device 153 has been combined with the endoaortic partitioning catheter 154. The fiberoptic illumination device 153 can serve two distinct purposes. The first function of the fiberoptic illumination device 153 can be for transillumination of the aortic wall W for detecting plaque and calcifications P in the aortic wall and for identifying the optimal point for creating a proximal anastomosis of a coronary bypass vein graft. In this embodiment, a fiberoptic bundle 155 is extended through the shaft 156 of the endoaortic partitioning catheter 154 to the distal end. The fiberoptic bundle 155 may be built into the wall of the catheter shaft 156 or a separate fiberoptic bundle 155 can be removably inserted through the infusion lumen of the catheter 154. At the distal end of the fiberoptic bundle 155 is a light diffuser 157 or a means for directing a broad lateral beam of light. The proximal end of the fiberoptic bundle is connected to a high intensity source of visible light 158. When the light beam or diffuse illumination passes through the wall W of the aorta, calcifications and heavy atherosclerotic plaque P can be detected as shadows in the aortic wall W. The exterior of the aorta can be observed with a thoracoscope inserted through an intercostal access port into the patient's chest.

The light source for the thoracoscope should be turned off while performing the transillumination so that the light coming through the aortic wall can be clearly seen. When this technique is used in open-chest bypass surgery, the lights in the operating room should be dimmed so that the light coming through the aortic wall can be seen. A clear, brightly lit section of the aortic wall W without shadows will indicate a relatively plaque free area of the aorta suitable for making the distal anastomosis. If a separate fiberoptic bundle 155 is inserted through the infusion lumen of the catheter 154, it can be manipulated from outside of the patient's body to scan the entire ascending aorta B to find the optimum anastomosis site or to find multiple anastomosis sites for multi-vessel bypass operations.

The second function of the fiberoptic illumination device 153 can be for facilitating placement of the endoaortic partitioning catheter 154 without the need for fluoroscopic guidance. In this embodiment, a fiberoptic bundle 155 is extended through the shaft 156 of the endoaortic partitioning catheter 154 to the distal end. Again, the fiberoptic bundle 155 may be built into the wall of the catheter shaft 156 or a separate fiberoptic bundle 155 can be removably inserted through the infusion lumen of the catheter 154. Located at the distal end of the fiberoptic bundle 155 is a means 157 for directing a narrow lateral beam of light to create a spot or a 360° ring of light around the tip of the catheter. The proximal end of the fiberoptic bundle 155 is connected to a high intensity source of visible light 158. When the endoaortic partitioning catheter 154 is inserted into the ascending aorta B, the position of the catheter tip can be determined by the position of the spot or ring of light where it shines through the aortic wall W. When the endoaortic partitioning catheter 154 is in the correct position, the occlusion balloon 159 can be inflated and a cardioplegic agent infused to arrest the heart.

These two functions of the fiberoptic illumination device 153 can be combined into one device if the optical elements are chosen to deliver a beam which is a compromise between the broad beam needed for aortic wall transillumination and the narrow beam preferred for the catheter location function. Alternatively, an optical system could be chosen which is selectively capable of delivering a broad or narrow lateral beam of light.

In other alternatively embodiments, the occlusion balloon 158 can be illuminated from the interior with the fiberoptic illumination device 153 to monitor balloon placement, inflation and migration. The effectiveness of the illumination can be enhanced by incorporating reflective or fluorescent material in the balloon or the inflation fluid.

Being able to detect the precise position of the endoaortic partitioning catheter 154 without the need for fluoroscopic imaging has the potential of simplifying the catheter placement procedure and the equipment needed in the operating room. Other non-fluoroscopic means for detecting the position of the catheter tip include placing a metallic or magnetic marker at the tip of the catheter and using a thoracoscopically placed Hall effect proximity detector or magnetometer in the chest cavity to detect the position of the catheter tip through the aortic wall. Another means of detecting the position of the catheter tip within the ascending aorta is by ultrasonic imaging. An endoscopic ultrasonic imaging probe can be introduced through an access port in the chest or a transoesophageal ultrasound probe can be used. The imaging of the catheter can be enhanced by placing an echogenic marker near the tip of the catheter. A material with significantly higher or lower acoustic impedance than the catheter and the surrounding tissue and blood can serve as an echogenic marker. For example, a metal ring with a roughened exterior surface or an air-filled pocket or ring of closed cell foam mounted on or embedded in the tip of the catheter will serve as an echogenic marker. The catheter tip can be observed with ultrasonic imaging as the catheter is advanced into the ascending aorta to assure proper placement of the occlusion balloon.

Figure 29:
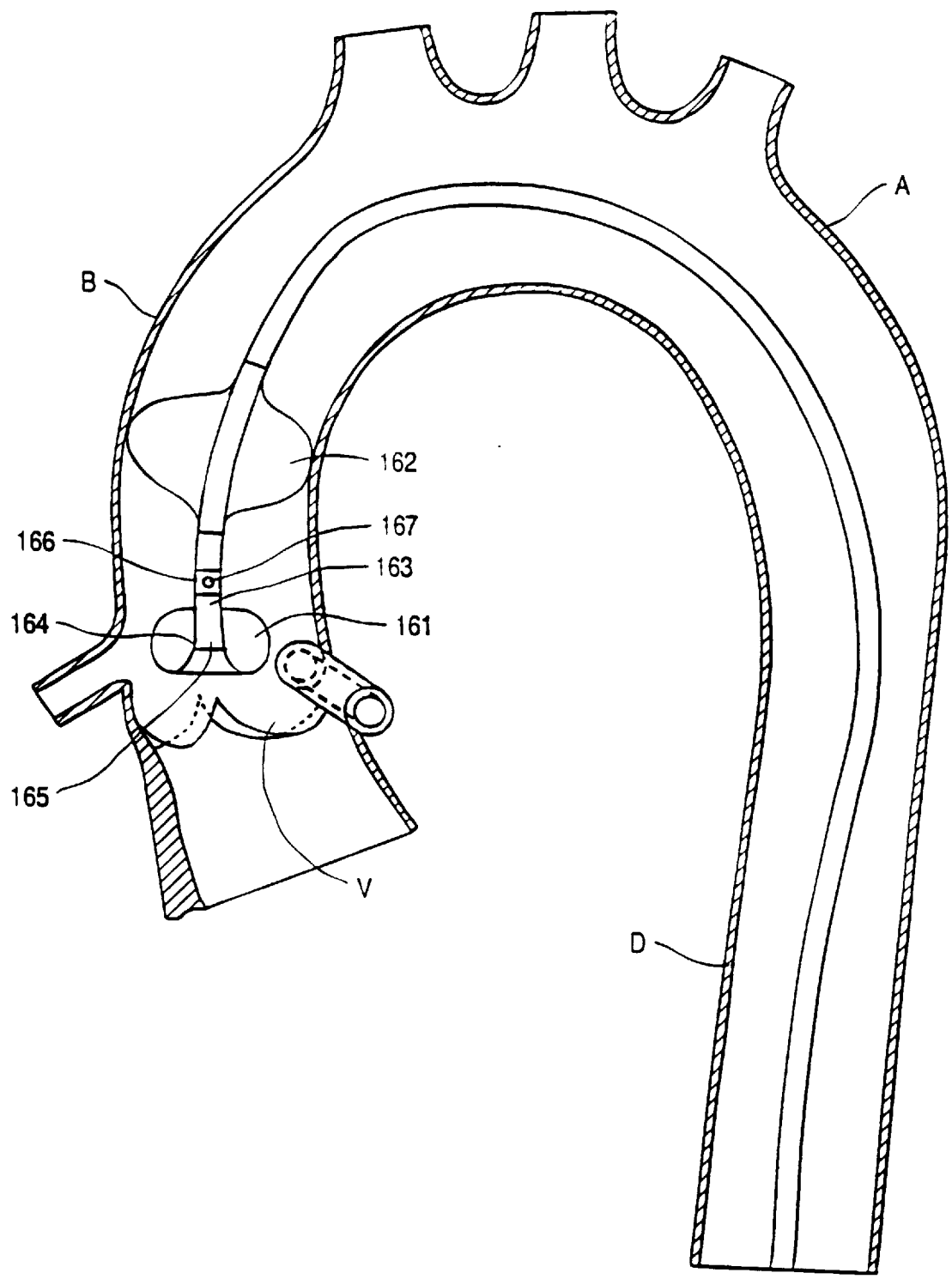
FIG. 29 illustrates an endoaortic partitioning catheter having an inflatable bumper balloon for protecting the aortic wall from the catheter tip and for facilitating non-fluoroscopic placement of the catheter.

Another approach for facilitating placement of the endoaortic partitioning catheter without the need for fluoroscopic guidance is illustrated in FIG. 29. This embodiment of the endoaortic partitioning catheter 160 has a second expandable member 161 mounted on the distal end of the catheter distal to the first expandable occlusion member 162. In a particular embodiment, the distal expandable member 161 is an inflatable balloon having a proximal balloon neck 163 which is attached to the catheter shaft 166 and a distal balloon neck 164 which is inverted and attached to the distal tip 165 of the catheter shaft. When the distal expandable member 161 is inflated, it expands to surround and protect the distal tip 165 of the catheter. If an expandable balloon is used for the first expandable occlusion member 162 the first 162 and second 161 expandable members can be inflated through a single inflation lumen within the catheter shaft 166. Preferably, however a separate second inflation lumen is provided for individually inflating the distal expandable member 162. The distal expandable member 162 preferably has a smaller expanded diameter than the first expandable occlusion member 161 so that it does not occlude the lumen of the ascending aorta B.

In operation, the endoaortic partitioning catheter 160 is inserted and advanced into the descending aorta D. Then, the distal expandable member 161 is inflated to act as a soft protective bumper for the distal end 165 of the catheter 160. The catheter 160 can be advanced over the aortic arch A and into the ascending aorta B with very little concern about causing trauma to the aortic wall or dislodging any calcifications or other emboli from the aortic wall as the catheter passes. When the catheter 160 is in the ascending aorta B, it is advanced slowly until the distal expandable member 161 comes into contact with the aortic valve V. The soft cushion provided by the inflated distal expandable member 161 prevents any damage to the aortic valve V. The operator will be able to feel that the catheter 160 has stopped advancing from the proximal end of the catheter which is outside of the patient's body and will know that the first expandable occlusion member 162 is in proper position in the ascending aorta B between the coronary ostia and the brachiocephalic artery without the need for fluoroscopic verification. The first expandable occlusion member 162 can be inflated to occlude the ascending aorta B and a cardioplegic agent infused through the perfusion lumen that exits the catheter through a port 167 distal to the first expandable occlusion member 162.

Figure 30A:
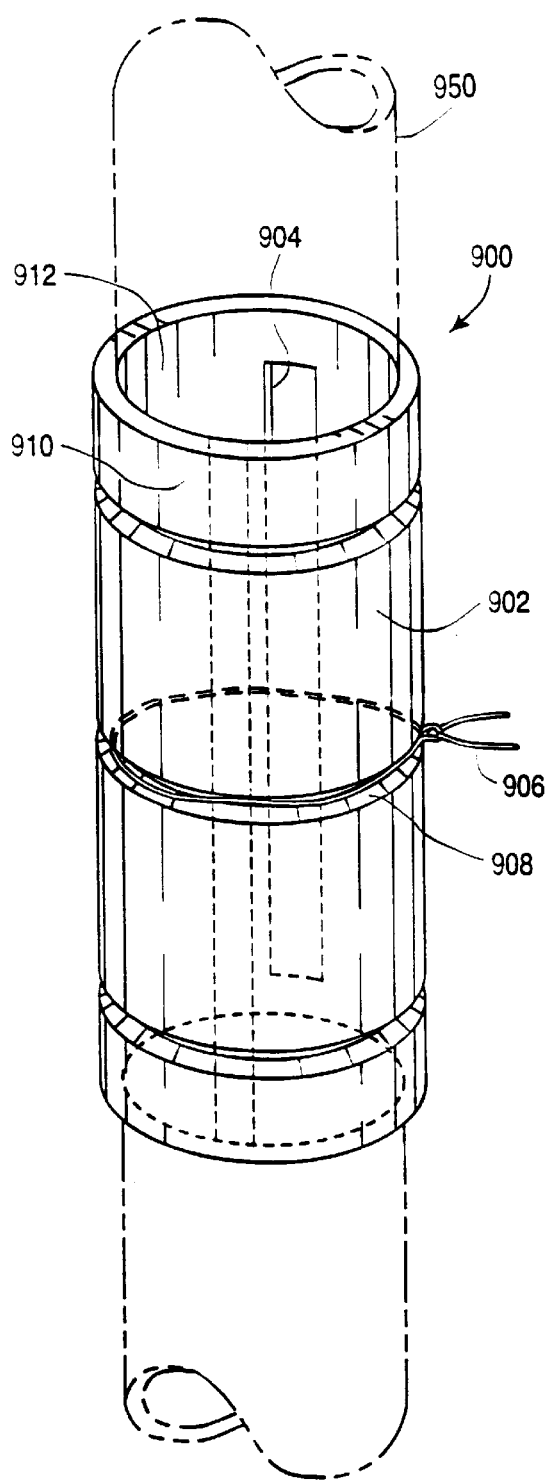
FIG. 30A is a rear three-quarter view of a frictional locking suture ring for use with the endoaortic partitioning catheter.
Figure 30B:
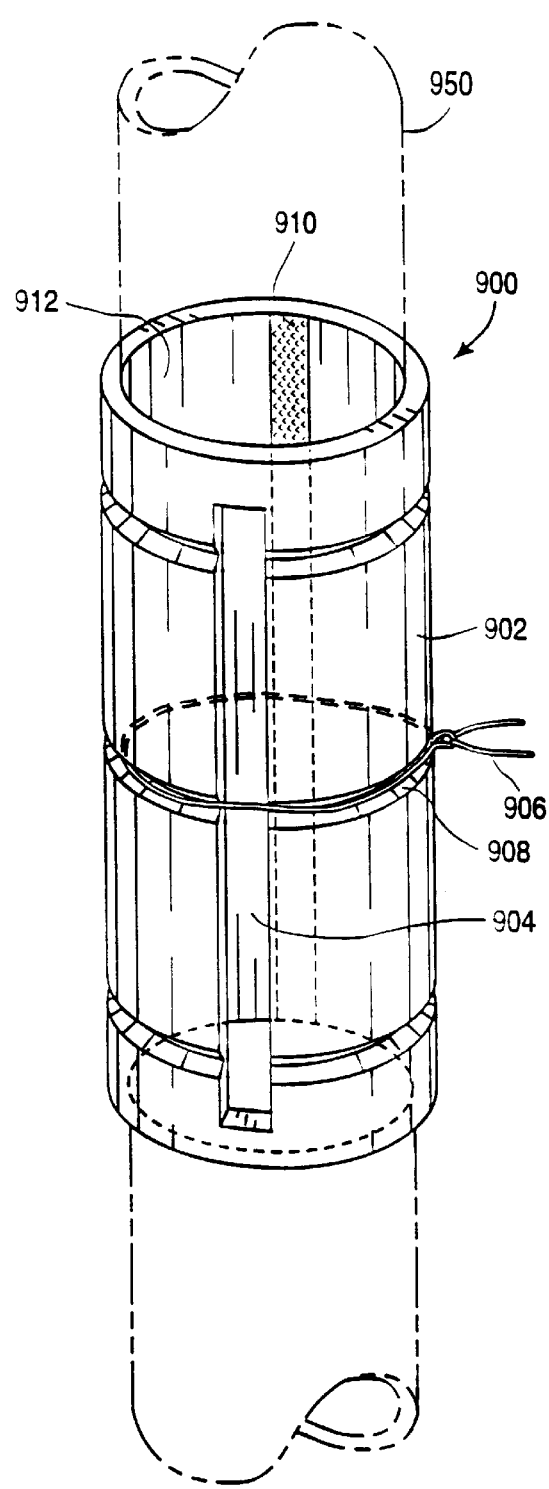
FIG. 30B is a front three-quarter view of the frictional locking suture ring of FIG. 30A.

FIGS. 30A and 30B are detail drawings of an additional feature of the invention which is a frictional locking suture ring 900 for use with the endoaortic partitioning catheter. For indwelling catheters, such as the endoaortic partitioning catheter, it is often desirable to fasten the catheter to the patient or to the surgical drapes to prevent undesired migration or dislodgement of the catheter from its correct position. The frictional locking suture ring 900 of FIGS. 30A and 30B is provided as part of the invention to facilitate anchoring the catheter in place to avoid unintentional movement of the catheter after it has been positioned in the ascending aorta. Typical suture rings on introducer sheaths, central venous catheters and other indwelling catheters are located at a fixed position near the proximal hub of the catheter. This is generally adequate for catheters where the precise placement of the distal tip of the catheter is not critical. With the endoaortic partitioning catheter, however, the precise placement of the distal tip of the catheter within the ascending aorta is highly critical and the distance from the point of insertion of the catheter into the peripheral arterial access site to the ascending aorta is highly variable from patient to patient. Therefore, a standard, fixed-position suture ring would be wholly inadequate in the present application. The frictional locking suture ring of FIGS. 30A and 30B allows the endoaortic partitioning catheter to be precisely positioned and reliably anchored in place with any desired length of the catheter shaft inserted at the access site.

The frictional locking suture ring 900 is preferably made from a tube 902 of a resilient, high-tack polymer, preferably an extrudable or injection moldable thermoplastic elastomer, such as a thermoplastic polyurethane with a hardness in the range of 70–90 Shore A durometer or Kraton™ (Shell Chemical Co.) thermoplastic elastomer with a hardness of about 40 Shore A durometer. The length of the tube 902 is typically from 2–3 cm. The internal diameter of the tube 902 is slightly larger than the external diameter of the shaft of the endoaortic partitioning catheter 920. In an exemplary embodiment for use with a 4 mm diameter or 12 French catheter, the internal diameter of the tube 902 is preferably about 4.5–4.8 mm, providing a diametrical clearance of approximately 0.5–0.8 mm. The external diameter of the tube 902 is typically about 6.5–7.0 mm. There is a longitudinal slot 904 about 1.2–2.0 mm wide through the side of the tube 902.

The frictional locking suture ring 900 is placed over the exterior of the endoaortic partitioning catheter 920 with the shaft of the catheter running through the lumen of the tube. Because of the diametrical clearance between the exterior of the catheter 920 and the interior of the tube 902, the suture ring 900 is free to move along the length of the catheter 920. However, when a suture 906 or other ligature is tied around the suture ring 900, the tube 902 compresses around the exterior of the catheter 920 and the high friction due to the tackiness of the suture ring material creates a firm, nonslip grip on the catheter shaft 920. To facilitate securing the suture 906 to the suture ring 900, a circumferential groove 908 is provided on the exterior of the tube 902. In the illustrative embodiment shown in FIGS. 30A and 30B, there are three circumferential grooves 908 around the tube at positions near the proximal end, the center and the distal end of the longitudinal slot 904 to provide places for tying a suture 906 around the suture ring 900. In an injection molded embodiment of the suture ring 900, other suture attachment means, such as one or more eyelets, can easily be provided on the exterior of the tube 902.

In order to increase the frictional grip between the frictional locking suture ring 900 and the shaft of the endoaortic partitioning catheter 920, a strip of high friction material 910 may be provided on the interior of the tube 902. In the illustrative embodiment of FIGS. 30A and 30B a 1.0 mm wide strip of high friction tape 910 has been adhesively bonded to the interior of the tube 902. A suitable material for use in this application is a self-adhesive high friction tape available from 3M Manufacturing Co., Inc. which is made of a polyurethane film with mineral particles embedded in the exterior surface to enhance the frictional properties. The high friction tape 910 is mounted in the tube 902 with the high friction gripping surface oriented toward the lumen 912 of the tube 902. When a suture 906 is tied around the exterior of the frictional locking suture ring 900, the high friction surface of the tape 910 is pressed against the exterior of the catheter shaft 920 to increase the grip on the catheter.

Preferably, the frictional locking suture ring 900 is placed over the catheter shaft from the distal end during manufacturing. In use, the suture ring 900 initially resides in an out of the way position at the proximal end of the catheter near the proximal hub while the catheter 920 is being introduced and maneuvered into position within the patient's aorta. Once the distal end of the catheter has been maneuvered to the proper position, the catheter 920 can be secured in position by sliding the suture ring 900 along the catheter shaft 920 until it is close to the introduction site. A suture 906 is tied around exterior of the suture ring 900 to create a frictional grip between the suture ring 900 and the catheter shaft 920. The suture 906 is then stitched through the patient's skin close to the insertion site and tied. This securely fastens the catheter 920 in the desired position relative to the patient's body with the correct length of catheter inserted into the patient's vasculature. If preferred, separate sutures can be used for tying the suture ring 900 and stitching it to the patient. Alternatively, the suture ring 900 can be secured to the surgical drapes covering the patient, though this is less preferred because there can be relative movement between the drapes and the catheter introduction site that could result in movement of the catheter from its desired position.

If it becomes necessary to reposition the catheter 920 at any time during the procedure, the frictional grip can be released by untying or cutting the suture 906 around the suture ring 900. The catheter 920 can be repositioned by sliding it through the lumen 912 of the suture ring and then it can be secured in the new position by retying the suture 906 around the suture ring 900. When it is time to remove the catheter 920, the suture 906 fastening the suture ring 900 to the patient can be cut and the suture ring 900 withdrawn with the catheter 920.

In a further aspect of the invention, illustrated in FIGS. 30–34, the endoaortic partitioning catheter 895 is coupled to an arterial bypass cannula 850 that is specially adapted to serve as a dual purpose arterial bypass cannula and introducer sheath so as to allow the catheter 895 and the cannula 850 to be introduced through the same arterial puncture. The smaller diameter endoaortic partitioning catheters made possible by the embodiments described in relation to FIGS. 5–9, are particularly suitable for use in combination with the special arterial bypass cannula 850. The arterial bypass cannula 850 is configured for connection to a cardiopulmonary bypass system for delivering oxygenated blood to the patient's arterial system. The arterial bypass cannula 850, shown in FIG. 31, has a cannula body 851 which is preferably made of a transparent, flexible, biocompatible polyurethane elastomer or similar material. In one preferred embodiment, the cannula body 851 has a 45° beveled distal end 853, a proximal end 852, a blood flow lumen 857 extending between the proximal end 852 and the distal end 853, and an outflow port 891 at the distal end 853. Alternatively, the cannula body 851 can have a straight cut distal end with chamfered or rounded edge. Optionally, a plurality of additional outflow ports may be provided along the length of cannula body 851, particularly near distal end 853. The cannula body 851 is tapered from the proximal end 852 to the distal end 853 and, in one preferred embodiment, the tapered cannula body 851 is reinforced with a coil of flat stainless steel wire 854 embedded in the wall of the cannula body 851. Adjacent to the proximal end 852 of the cannula body 851, proximal to the reinforcing coil 851, is a clamp site 851 which is a flexible section of the tubular cannula body 851 that can be clamped with an external clamp, such as a Vorse type tube occluding clamp, forming a hemostatic seal to temporarily stop blood flow through the lumen 857 of the cannula 850. In a preferred embodiment, the cannula body 851 has a length between about 10 cm and 60 cm, and preferably between about 12 cm and 30 cm. In one particular embodiment, the cannula body 851 has a distal external diameter of approximately 7 mm or 21 French (Charrière scale) and a distal internal diameter of approximately 6.0 mm or 18 French. In a second particular embodiment, the cannula body 851 has a distal external diameter of approximately 7.7 mm or 23 French (Charrière scale) and a distal internal diameter of approximately 6.7 mm or 20 French. Preferably, the proximal end 852 of the cannula body 851 of either embodiment has an internal diameter of approximately ⅜ inch or 9.5 mm. The choice of which embodiment of the arterial bypass cannula 850 to use for a given patient will depend on the size of the patient and the diameter of the artery chosen for the arterial cannulation site. Generally, patients with a larger body mass will require a higher infusion rate of oxygenated blood while on cardiopulmonary bypass, therefore the larger arterial bypass cannula 850 should be chosen if the size of the artery allows.

Figure 34:
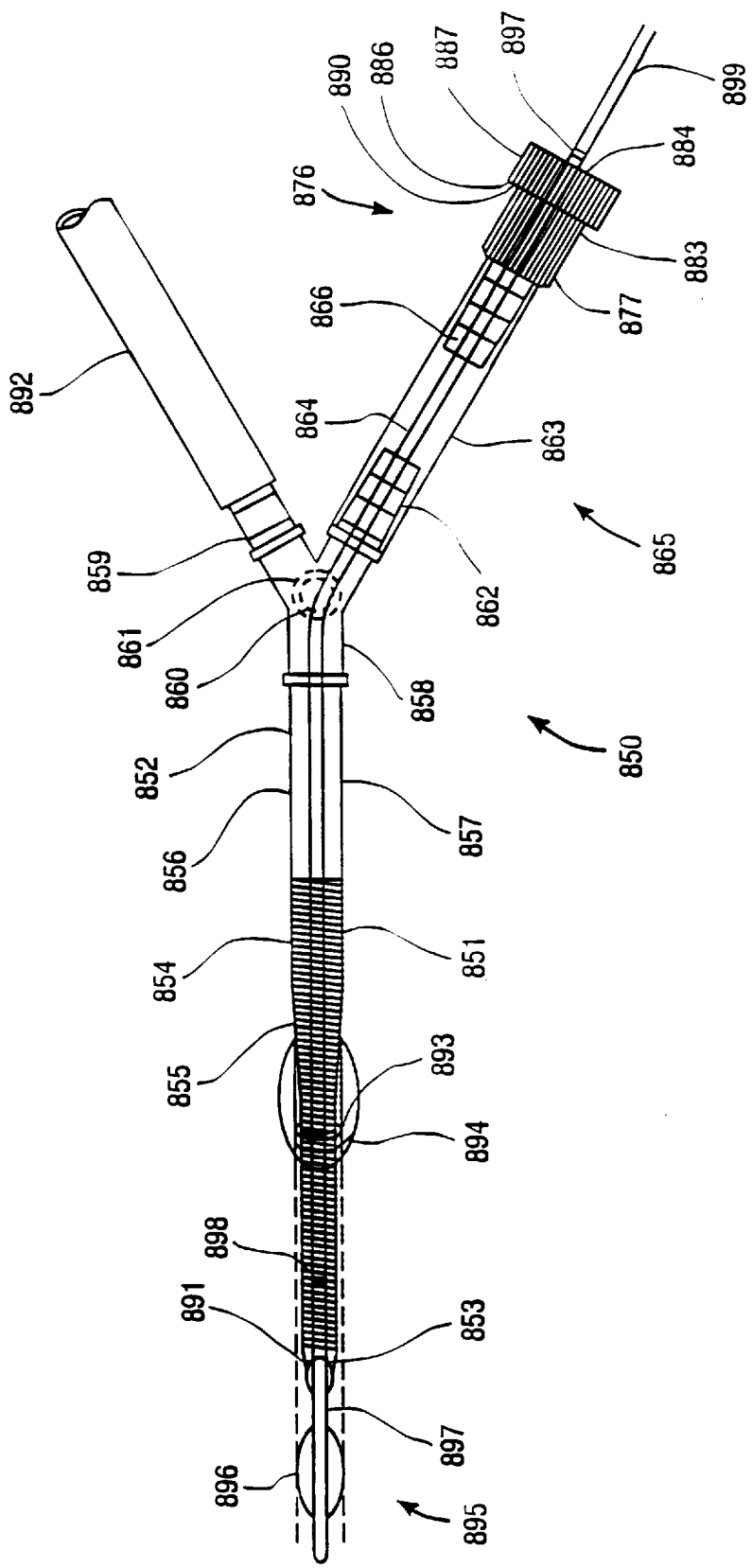
FIG. 34 illustrates the cannula of FIGS. 31 and 32 with the endoaortic partitioning catheter introduced into the patient's femoral artery.

An adapter assembly 865 is connected to the proximal end 852 of the cannula body 851. In one preferred embodiment, the adapter assembly 865 and the cannula body 851 are supplied preassembled as a single, sterile, ready-to-use unit. Alternatively, the adapter assembly 865 can be packaged and sold as a separate unit to be connected to the cannula body 851 at the point of use. The adapter assembly 865 has a Y-fitting 858 which is connected to the proximal end 852 of the cannula body 851. The Y-fitting 858 has a first branch ending in a barbed connector 859 which is configured for fluid connection to tubing 892 from a cardiopulmonary bypass system, as shown in FIG. 34. To prepare the arterial bypass cannula 850 for insertion into a peripheral artery, such as a patient's femoral artery or brachial artery, by an arterial cutdown or by a percutaneous Seldinger technique, a connector plug 871, which is molded of a soft, elastomeric material, is placed over the barbed connector 859. A tapered dilator 867 is passed through a wiper-type hemostasis seal 872 in the connector plug 871. The wiper-type hemostasis seal 872 is a hole through the elastomeric connector plug 871 that has a slight interference fit with the external diameter of the dilator 867. A series of ridges can be molded within the hemostasis seal 872 to reduce the sliding friction on the dilator 867 while maintaining a hemostatic seal. The dilator 867 has a tapered distal tip 869, a proximal hub 870 with a luer lock connector, and a guidewire lumen 879, sized for an 0.038 inch diameter guidewire, that runs from the distal tip 869 to the proximal hub 870. The diameter of the dilator 867 is such that the dilator 867 substantially fills the cannula lumen 857 at the distal end 853 of the cannula body 851. The length of the dilator 867 is such that the distal tip 869 of the dilator 867 extends approximately 2 to 5 cm, and more preferably 4 to 5 cm, beyond the beveled end 853 of the cannula body 851 when the dilator hub 870 is against the connector plug 870. The dilator 867 may assume a bend 873 in it at the point where the dilator 867 passes through the Y-fitting 858 when the dilator 867 is fully inserted. One or more depth markers 874, 875 can be printed on the dilator 867 with a nontoxic, biocompatible ink. One depth marker 874 may be placed so that, when the marker 874 is just proximal to the hemostasis seal 872 on the elastomeric connector plug 871, the tapered distal tip 869 of the dilator 867 is just emerging from the beveled end 853 of the cannula body 851. In one particular embodiment, the tapered dilator 867 is made of extruded polyurethane with a radiopaque filler so that the position of the dilator can be verified fluoroscopically.

A second branch of the Y-fitting 858 is connected to an extension tube 862 which terminates in a hemostasis valve 876 configured to receive the endoaortic partitioning catheter 895 therethrough. The extension tube 862 has a flexible middle section which serves as a proximal clamp site 864 that can be clamped with an external clamp, such as a Vorse type tube occluding clamp, forming a hemostatic seal to temporarily stop blood flow through the lumen 863 of the extension tube 862. The lumen 863 of the extension tube 862 between the proximal clamp site 864 and the hemostasis valve 876 serves as a catheter insertion chamber 866, the function of which will be more fully explained in connection with FIG. 33.

In a preferred embodiment of the arterial bypass cannula 850, the hemostasis valve 876 is a type of compression fitting known in the industry as a Tuohy-Borst adapter. The Tuohy-Borst adapter 876 is shown in greater detail in FIG. 32. The Tuohy-Borst adapter 876 has a compressible tubular or ring-shaped elastomeric seal 883 that fits within a counterbore 879 in the fitting body 877. The elastomeric seal 883 is preferably made from a soft, resilient, self-lubricating elastomeric material, such as silicone rubber having a hardness of approximately 20–50 and preferably 40–50 Shore A durometer. The elastomeric seal 883 has a central passage 884 with a beveled entry 885 on the proximal end of the passage 884. The elastomeric seal 883 has a beveled distal surface 886 angled at about 45° which fits against a tapered seat 880 in the bottom of the counterbore 879 that is angled at about 60°. A threaded compression cap 887 screws onto the fitting body 877. The threaded cap 887 has a tubular extension 887 which fits within the counterbore 879 in the fitting body 877. An externally threaded section 888 on the proximal end of the tubular extension 887 engages an internally threaded section 881 within the proximal end of the counterbore 879. When the threaded cap 887 is screwed down onto the fitting body 877, the tubular extension 889 bears on the elastomeric seal 883 forcing it against the tapered seat 880 of the counterbore 879. The resultant force on the elastomeric seal 883 squeezes the elastomeric seal 883 inward to close off the passage central 884 to make a hemostatic seal. When the threaded cap 887 is unscrewed again from the fitting body 877, the central passage 884 of the elastomeric seal 883 opens up again. The deliberate 15° mismatch between the angle of the beveled distal surface 886 of the elastomeric seal 883 and the tapered seat 880 of the counterbore 879 prevents the elastomeric seal 883 from binding and causes the central passage 884 to open up reliably when the threaded cap 887 is unscrewed from the fitting body 887. An internal ridge 890 within the threaded cap 887 engages in a snap fit with an external ridge 882 on the proximal end of the fitting body 877 to keep the threaded cap 887 from being inadvertently separated from the fitting body 877 if the threaded cap 887 is unscrewed to the point where the threads 888, 881 are no longer engaged.

In one particular embodiment, the central passage 884 of the elastomeric seal 883 has an internal diameter of about 5 mm to allow clearance for inserting a catheter 895 with a shaft diameter of 3–4 mm through the Tuohy-Borst adapter 876 without damaging the occlusion balloon 896 mounted on it. The Tuohy-Borst adapter 876 is adjustable through a range of positions, including a fully open position for inserting the balloon catheter 896, a partially closed position for creating a sliding hemostatic seal against the shaft 897 of the catheter 895, and a completely closed position for creating a hemostatic seal with no catheter in the central passage 884. In an alternative embodiment, the central passage 884 of the elastomeric seal 883 can be sized to have a slight interference fit with the shaft 897 of the catheter 895 when uncompressed. In this embodiment, the Tuohy-Borst adapter 876 has positions which include a fully open position for creating a sliding hemostatic seal against the shaft 897 of the catheter 895, and a completely closed position for creating a hemostatic seal with no catheter in the central passage 884. In a second alternative embodiment, a separate ring-like wiper seal (not shown) is added in series with the Tuohy-Borst adapter 876 to create a passive sliding hemostatic seal against the shaft 897 of the catheter 895 without the necessity of tightening the threaded cap 887. Additionally, the Tuohy-Borst adapter 876, in either embodiment, may have a tightly closed position for securing the catheter shaft 897 with respect to the patient. In other alternative embodiments, other known hemostasis valves may be substituted for the Tuohy-Borst adapter 876 as just described.

In a particularly preferred embodiment, the internal surface of the lumen 863 of the extension tube 862 and/or the internal surface of the lumen 857 of the cannula body 851 are coated with a highly lubricious biocompatible coating, such as polyvinyl pyrrolidone, to ease the passage of the endoaortic partitioning catheter 895, and especially the occlusion balloon 896, through these lumens. Other commercially available lubricious biocompatible coatings can also be used, such as Photo-Link™ coating available from BSI Surface Modification Services of Eden Prairie, Minn.; sodium hyaluronate coating available from Biocoat of Fort Washington, Pa.; proprietary silicone coatings available from TUA of Sarasota, Fla.; and fluid silicone or silicon dispersions. Similarly, a distal portion of the exterior of the cannula body 851 can be coated with one of these lubricious biocompatible coatings to facilitate insertion of the arterial bypass cannula 850 into the artery at the cannulation site. Furthermore, the endoaortic partitioning catheter 895 itself, in any of the embodiments described herein, can be coated with one of these lubricious biocompatible coatings to facilitate its insertion and passage through the arterial bypass cannula 850 and the patient's vasculature. Preferably, the occlusion balloon 896 of the endoaortic partitioning catheter 895 should be free of any lubricious coating so that there is sufficient friction between the expanded occlusion balloon and the interior aortic wall to prevent accidental dislodgement or migration of the occlusion balloon 896.

Figure 31:
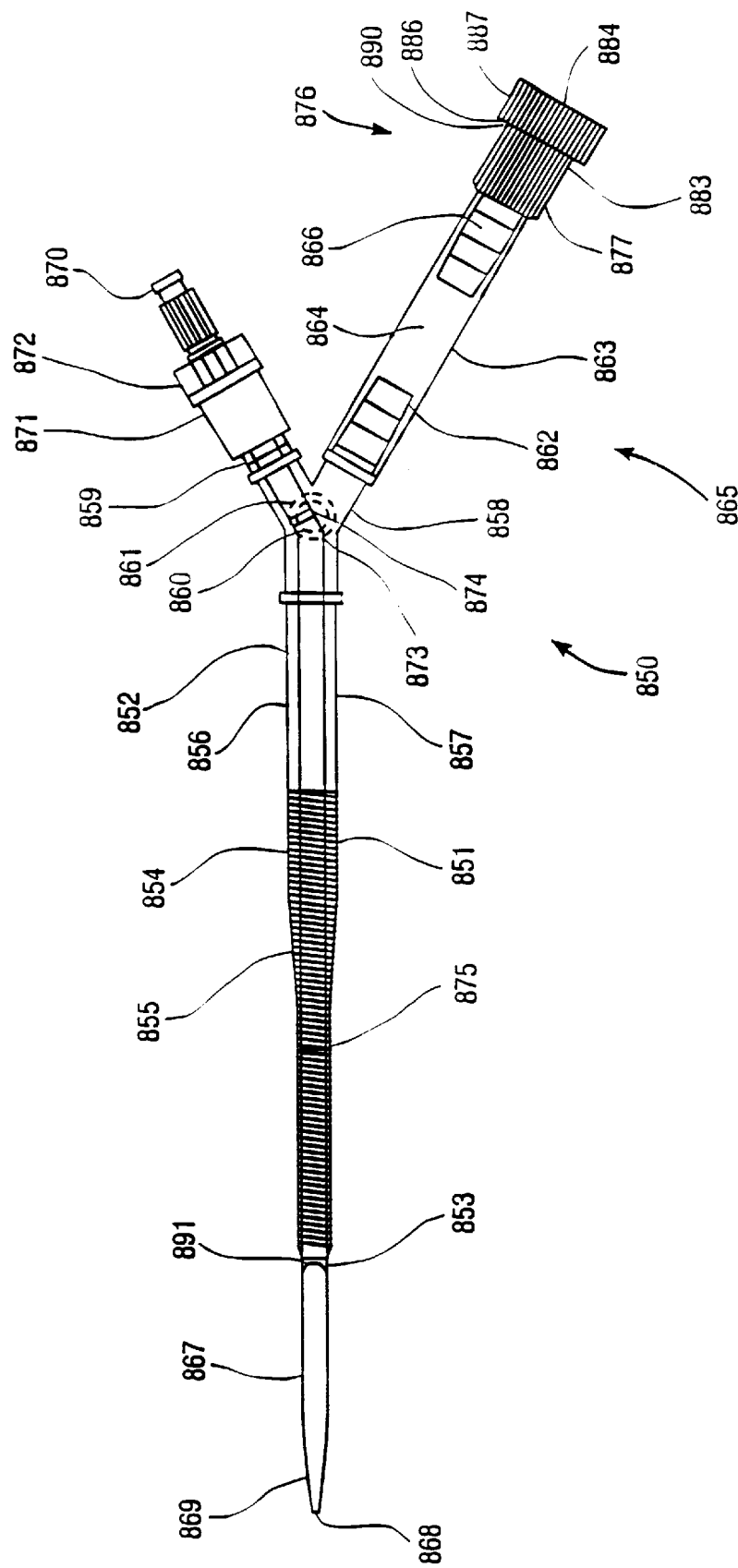
FIG. 31 is a front view of a dual function arterial cannula and introducer sheath for use with the endoaortic partitioning catheter.
Figure 32:
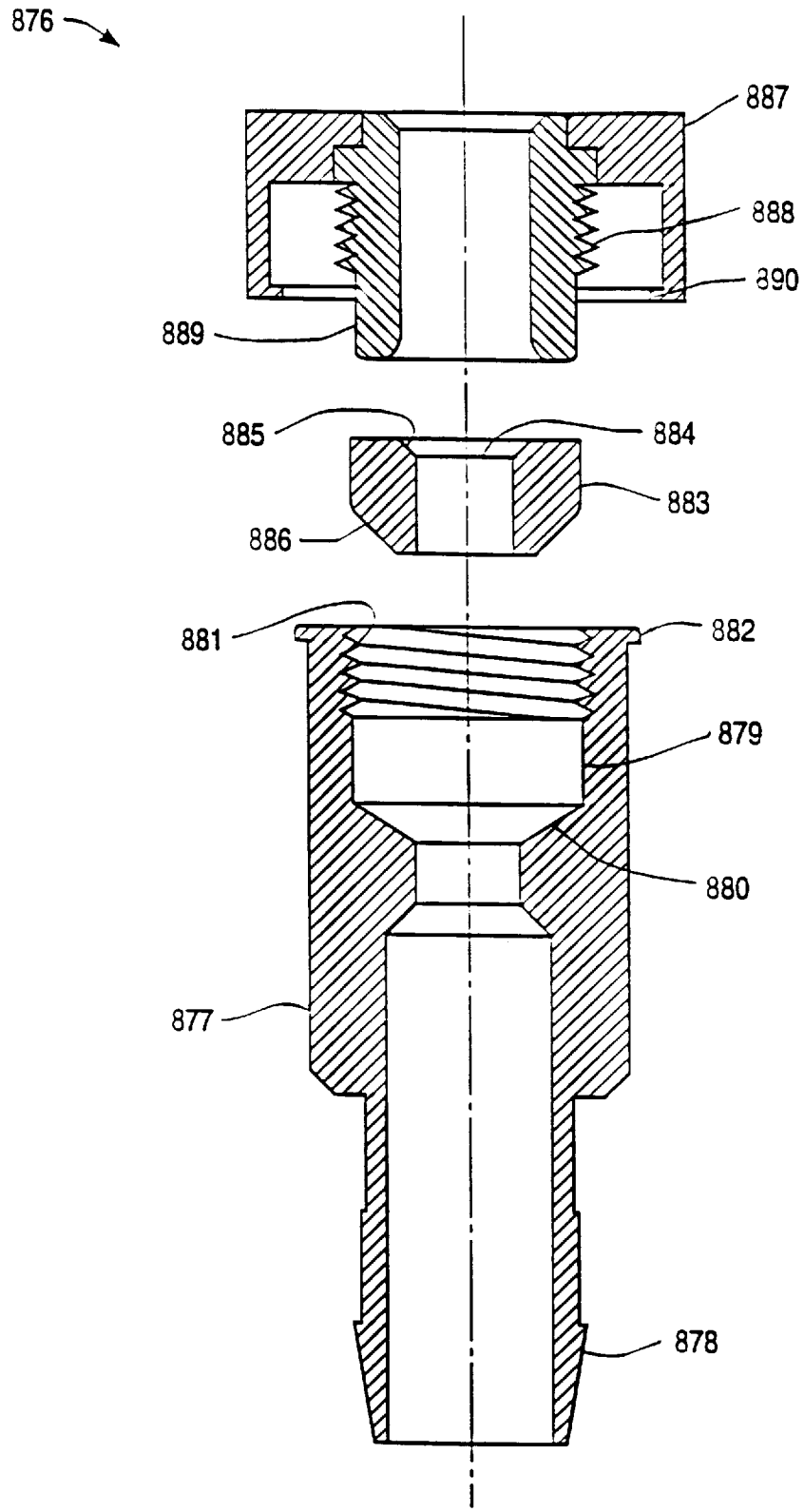
FIG. 32 is a cross sectional view of the hemostasis fitting of the dual function arterial cannula and introducer sheath of FIG. 31.
Figure 33:
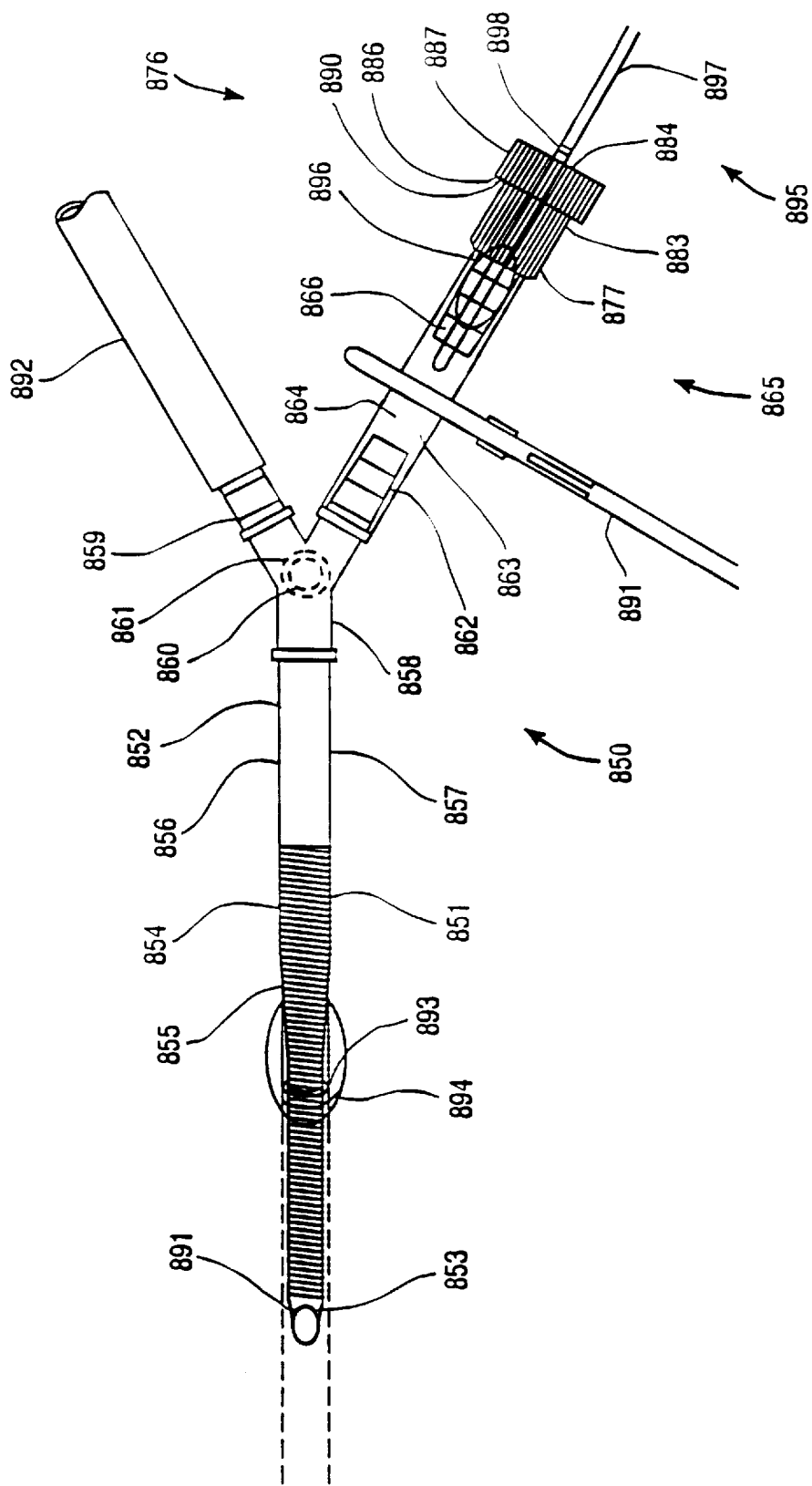
FIG. 33 illustrates the cannula of FIG. 31 with an endoaortic partitioning catheter introduced into the catheter insertion chamber.

In operation, the arterial bypass cannula 850 is prepared for insertion as shown in FIG. 31, with the tapered dilator 867 in place in the blood flow lumen 857 of the cannula body 851 and with the Tuohy-Borst fitting 876 completely closed. An arterial cutdown is made into an artery, preferably the patient's femoral artery, at the cannulation site or a guidewire is placed percutaneously using the Seldinger technique and the dilator 867 and the distal end 853 of the cannula body 851 are inserted into the lumen of the artery with the bevel up. A suture 894 can be tied around the artery 893 where the cannula body 851, as shown in FIG. 33, inserts to avoid bleeding from the artery 893 at the cannulation site. The dilator 867 is then withdrawn from the cannula body 851, allowing blood to flash back and fill the lumen 857 of the cannula body 851. When the tip 868 of the dilator 867 is proximal to the distal clamp site 856 an external clamp is applied to the distal clamp site 856 to stop further blood flow. The dilator 867 is completely withdrawn and the connector plug 871 is removed so that a tube 892 from the cardiopulmonary bypass system can be attached to the barbed connector 859 of the Y-fitting 858, as shown in FIG. 33. Air is bled from the arterial bypass cannula 850 by elevating the extension tube 862 and opening the Tuohy-Borst fitting 876 slightly and releasing the external on the distal clamp site 856 to allow the blood to flow out through the Tuohy-Borst fitting 876. Alternatively, air can be bled out of the arterial bypass cannula 850, through an optional vent fitting with a luer cap (not shown) that can be provided on the Y-fitting 858 or an infusion line and a three-way stopcock. The optional vent fitting can be also used as a port for monitoring perfusion pressure within the arterial bypass cannula 850. Once the air is bled out of the system, the external clamp can be removed from the distal clamp site 856 the cardiopulmonary bypass system pump can be turned on to perfuse the patient's arterial system with oxygenated blood at a rate of about 3 to 6 liters/minute, preferably at a pump pressure of less than about 500 mm Hg.

To introduce the endoaortic partitioning catheter 895 into the arterial bypass cannula 850, an external clamp 891 is placed on the proximal clamp site 864, as shown in FIG. 33, to stop blood from flowing out through the extension tube 862 and the Tuohy-Borst adapter 876 is opened all the way by unscrewing the threaded cap 887 to open up the passage 884 through the elastomeric seal 883. The distal end of the endoaortic partitioning catheter 895 with the occlusion balloon 896 mounted thereon is inserted through the passage 884 of the Tuohy-Borst adapter 876 into the insertion chamber 866 of the arterial bypass cannula 850. Optionally, first and second depth markers 898, 899 may be printed on the shaft 897 of the endoaortic partitioning catheter 895 with a nontoxic, biocompatible ink. The first depth marker 898 on the catheter 895 indicates when the occlusion balloon 896 is entirely distal to the elastomeric seal 883. When the first depth marker 898 is positioned just proximal to the threaded cap 887, the Tuohy-Borst adapter 876 should be tightened to create a sliding, hemostatic seal around the catheter shaft 897. Now, the clamp 891 can be removed to allow the catheter 895 to be advanced distally through the arterial bypass cannula 850.

Before the endoaortic partitioning catheter 895 enters the blood flow lumen 857 within the Y-fitting 858, the perfusion rate from the cardiopulmonary bypass system pump should be temporarily turned down to a rate of about 1 to 2 liters/minute to avoid hemolysis, tubing disruptions or other complications due to the additional flow resistance caused by the occlusion balloon 896 as it passes through the blood flow lumen 857. The catheter 895 can now be advanced distally until the occlusion balloon 986 is distal to the distal end 853 of the cannula body 851. A second depth marker 899 on the catheter 895 indicates when the occlusion balloon 896 is entirely distal to the distal end 853 of the cannula body 851. When the second depth marker 898 reaches the proximal end of the threaded cap 887, as shown in FIG. 33, the perfusion rate from the cardiopulmonary bypass system pump should be returned to a rate of about 3 to 6 liters/minute. The endoaortic partitioning catheter 895 can now be advanced into the ascending aorta for partitioning the heart and inducing cardioplegic arrest according to the methods described above. When the endoaortic partitioning catheter 895 is in position within the ascending aorta the Tuohy-Borst adapter 876 can be tightened around the catheter 895 to act as a friction lock to hold the catheter in place.

After completion of the surgical procedure on the heart, the endoaortic partitioning catheter 895 can be removed from the arterial bypass cannula 850 by reversing the sequence of operations described above. The arterial bypass cannula 850 can remain in place until the patient has been weaned from cardiopulmonary bypass, then the arterial bypass cannula 850 can be removed and the arterial puncture site repaired.

It should be noted that for the venous side of the cardiopulmonary bypass system, a similar dual purpose venous bypass cannula and introducer sheath with the above-described features can be used for accessing the femoral vein and for introducing a venting catheter or other devices into the venous side of the circulatory system. In a venous configuration the dual purpose venous bypass cannula and introducer sheath preferably has an external diameter of about 21 to 32 French units, an internal diameter of about 18 to 30 French units, and a length of about 50 to 75 cm.

FIGS. 35A–35C illustrate another means of steering the distal tip 171 of the endoaortic partitioning catheter 170 for centering the catheter tip within the ascending aorta B. The endoaortic partitioning catheter 170 is shown positioned within the patient's aortic arch A in FIG. 35A. The distal tip 171 of the catheter 170 is made steerable by a multichamber occlusion balloon 172 mounted on the distal portion 173 of the catheter which is shown partially cut away in FIG. 35A. The distal portion 173 of the catheter 170 has a distal curve which may be a 180°±45° arc or a 270°±45° arc, as described in previous embodiments. The multichamber occlusion balloon 172 has a first chamber 174 and a second chamber 175. The balloon 172 is mounted so that the first chamber 174 is oriented toward the outside of the distal curve and the second chamber 175 is oriented toward the inside of the distal curve. A first inflation lumen 176 in the catheter 170 connects to the first chamber 174 through a first inflation port 178. A second inflation lumen 177 in the catheter 170 connects to the second chamber 175 through a second inflation port 179. An infusion lumen 181 connects with one or more infusion ports 182 at the distal tip 171 of the catheter 170.

As shown in the cross section of the deflated occlusion balloon 172 in FIG. 35B, a partition wall 180 separates the first 174 and second 175 chambers of the balloon 172. The first 174 and second 175 chambers of the balloon 172 may be differentially inflated through the inflation lumens 176, 177. For example, the cross section of FIG. 35C shows the first chamber 174 of the multichamber occlusion lumen 172 inflated to a greater degree than the second chamber 175. Because the first chamber 174 is oriented toward the outside of the distal curve of the catheter 170, the distal tip 171 of the catheter 170 is forced toward the inside of the aortic arch A, that is, toward the left side of the patient, as in FIG. 35A. Alternatively, the second chamber 175 can be inflated to a greater degree than the first chamber 174 to force the distal tip 171 of the catheter 170 toward the outside of the aortic arch A, that is, toward the right side of the patient. Thus, the distal tip 171 of the catheter 170 can be steered to center the tip 171 within the lumen of the ascending aorta B under fluoroscopic observation by inflating and deflating the individual chambers of the multichamber occlusion balloon 172. It should be noted that the multichamber occlusion balloon 172 is not limited to only two chambers. The multichamber occlusion balloon 172 can be made with three, four or more chambers to give the distal tip 171 greater degrees of steerability.

Figure 36:
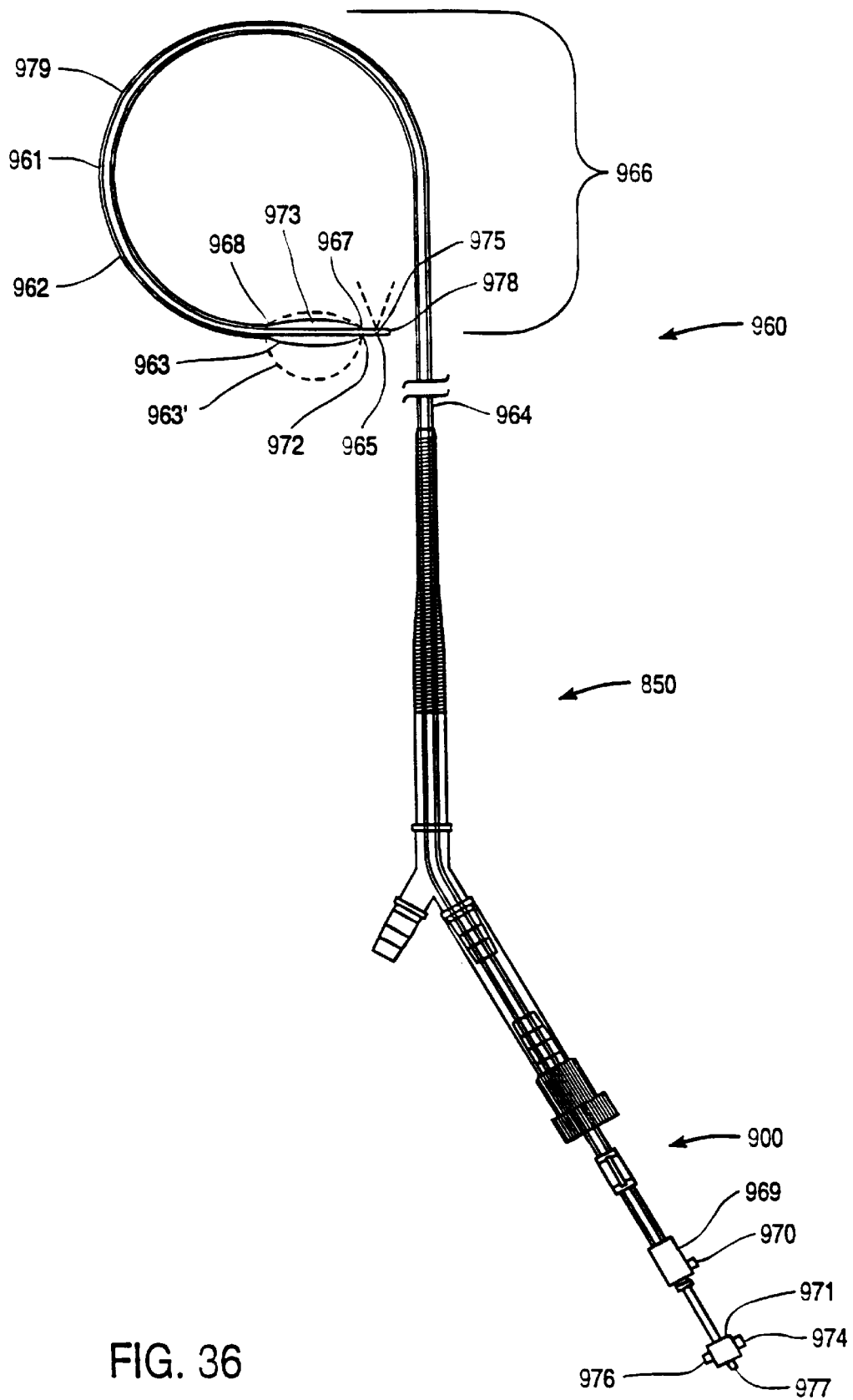
FIG. 36 illustrates a multifunction embodiment of the endoaortic partitioning catheter combined with a dual function arterial cannula and introducer sheath and a frictional locking suture ring.

It should be noted that while several aspects of the present invention have been illustrated and discussed separately in the foregoing description, many of these aspects can be advantageously combined into a single, multifunction embodiment. As an illustrative example, FIG. 36 shows a multifunction embodiment of the endoaortic partitioning catheter 960 combining several of the inventive aspects previously discussed. The shaft 964 of the catheter 960 has a coaxial construction with an inner 961 and outer 962 tubular member, similar to the embodiments described in connection with FIGS. 5A–5D and 6A–6D. The catheter shaft 964 may be made with varying degrees of stiffness along the length of the shaft 964, culminating in a soft atraumatic tip 965 which may be highly loaded with a radiopaque filler. The catheter shaft 964 may be made with a precurved distal portion 966 similar to FIGS. 10A–10B, or with a precurved distal portion 966 which is out of plane with the proximal portion of the catheter shaft 964, as in FIGS. 11A–11B. An expandable occlusion balloon 963 is mounted on the distal portion 966 of the catheter shaft 964. The occlusion balloon 963 preferably has a low profile deflated state with an ellipsoidal shape, similar to that shown in FIG. 6A. In addition, the occlusion balloon 963 may have an eccentric or asymmetrical inflated profile 963', similar to any of the embodiments discussed in relation to FIGS. 14–26, or FIG. 35 which would also provide a steering means for the distal tip of the catheter, as would the steering mechanism of FIG. 27.

The occlusion balloon 963 is mounted with its distal balloon neck 967 attached to the inner tubular member 961 and its proximal balloon neck attached to the outer tubular member 962. The inner tubular member 961 is attached at its proximal end to a first hub 971 and the outer tubular member 962 is attached at its proximal end to a second 969 hub 971 which are axially slidably and/or rotatable with respect to one another, similar to the embodiments described in relation to FIGS. 8A–8D and 9A–9B. An infusion fitting 977, such as a luer lock, on the first hub 971 is connected to an infusion lumen 978 which terminates at the distal end of the catheter 960. An inflation fitting 970, preferably a luer lock, on the second hub 971 is connected to an inflation lumen 979 defined by an annular space between the inner 961 and outer 962 tubular members which communicates with the interior of the occlusion balloon 963.

The second hub 969 may be moved proximal and/or rotated with respect to the first hub 971 to minimize the deflated profile of the occlusion balloon 963. The lower deflated profile of the occlusion balloon 963 facilitates easy insertion of the catheter 960 through a dual function arterial cannula and introducer sheath 850, similar to that described in relation to FIGS. 31–34. When the endoaortic partitioning catheter 960 is combined with the dual function arterial cannula and introducer sheath 850, the shaft 964 of the catheter 960 should be made with an additional 20–25 cm of length for a total shaft length of approximately 100–115 cm. The diameter of the catheter shaft 964 should also be minimized as much as possible to reduce the amount of cross sectional area the catheter shaft 964 takes up in the blood flow lumen of the arterial cannula 850. To this end, this combined embodiment is made with a distal pressure transducer 972 and a balloon pressure monitoring transducer 973 mounted on the inner tubular member 961, as described in relation to FIGS. 7A–7C. The distal pressure transducer 972 and the balloon pressure monitoring transducer 973 are electrically connected to an electrical connector 974 on the first hub 971. Also on the first hub 971 is a fiberoptic connector 976 which connects to a fiberoptic bundle 975 which terminates with a means for directing a lateral beam of light at the distal end of the catheter 960 for aortic transillumination and/or for facilitating nonfluoroscopic placement of the catheter 960. The fiberoptic bundle 975 may also be made as a separate unit for insertion through the infusion lumen 978 of the catheter 960 to further reduce the catheter shaft diameter while maintaining maximum functionality. The diameter of the catheter shaft 964 can thus be reduced to as small as 8 to 10.5 French (2.7–3.5 mm diameter).

Additionally the endoaortic partitioning catheter 960 may be combined with a frictional locking suture ring 900 for anchoring the catheter 960 in the proper position after placement, as described in relation to FIGS. 30A–30B.

Figure 37:
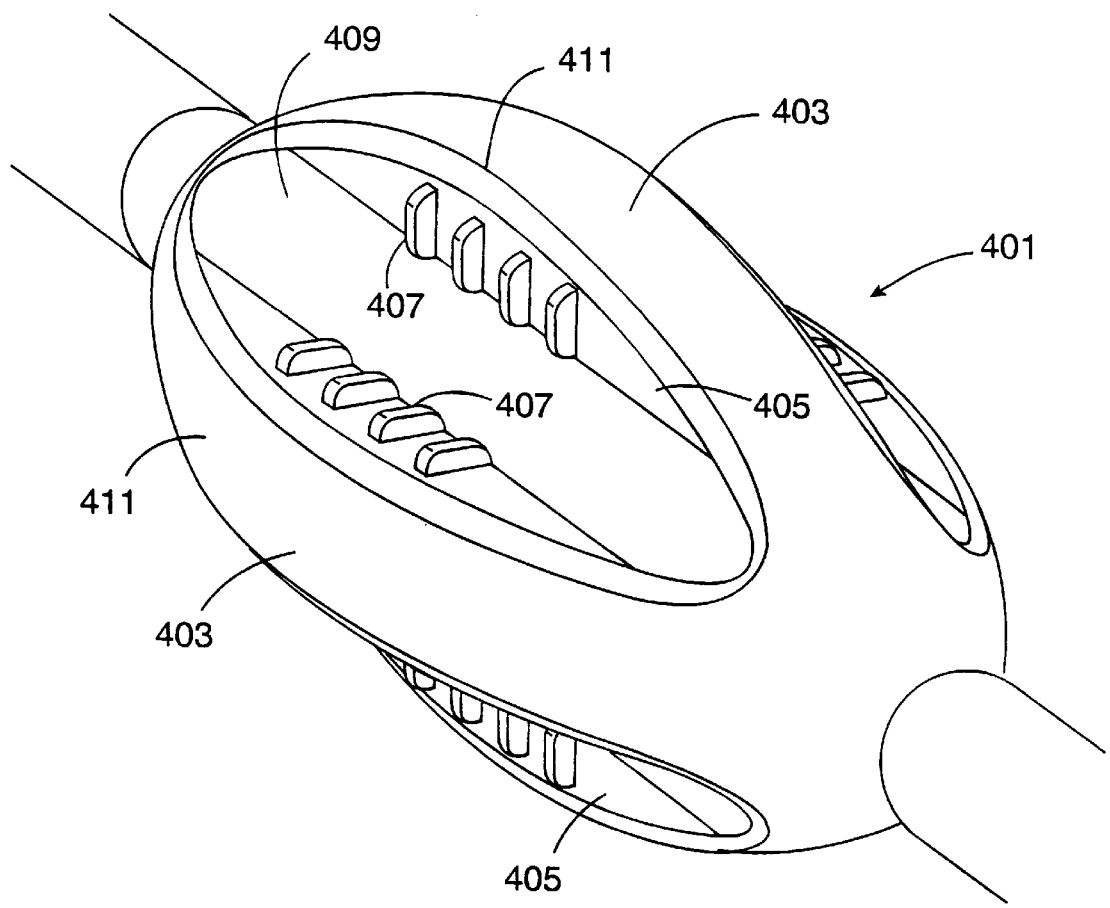
FIG. 37 shows a balloon having a first, high friction portion and a second, low friction portion.

Referring to FIG. 37, another preferred balloon 401 is shown which includes surface features for reducing migration of the balloon 401. The balloon 401 includes an outer surface having a first, low-friction portion 403 and a second, high-friction portion 405. The second, high-friction portion 405 includes a number of short ribs 407 and a selective coating 409 which enhance the frictional engagement between the balloon 401 and the aortic lumen relative to the frictional engagement between the first portion 403 and the aortic lumen. The selective coating 409 may be provided by masking the first portion 403 and sandblasting the second portion 405. Alternatively, the method described in PCT/US94/09489 may be used to provide the high friction portion 405. The balloon 401 preferably has a substantially oval cross-sectional shape tapered in the distal and proximal directions, however, any balloon shape may be used.

Figure 38:
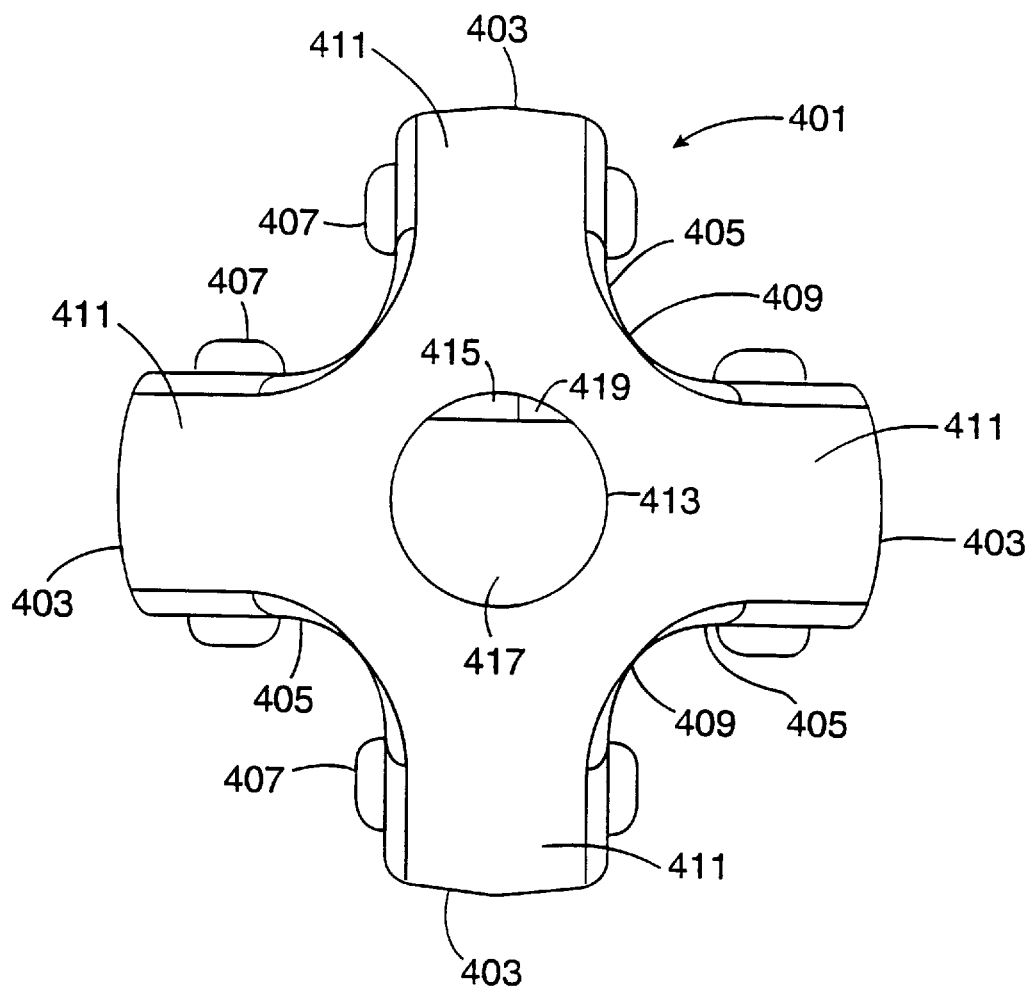
FIG. 38 is an end view of the balloon of FIG. 37.

Referring to the end view of FIG. 38, the balloon 401 preferably includes at least three, and more preferably at least four, arms 411 extending radially outward. A number of low-friction portions 403 are positioned at radially-outward portions of the arms 411. The high friction portions 405 are positioned between the low friction portions 403 so that when the balloon passes through a cylindrical body, such as a blood vessel, the low-friction portions 403 contact the vessel while the first, high-friction portions 405 do not. The balloon 401 is preferably evacuated prior to insertion into the patient at which time it can be verified that the radially extending arms 411 are present. Although it is preferred to provide the radially-extending arms 411, the balloon 401 may be configured in any other fashion so long as the low friction portions 403 are at radially-outward positions relative to the exposed, high friction portions 405.

Figure 39:
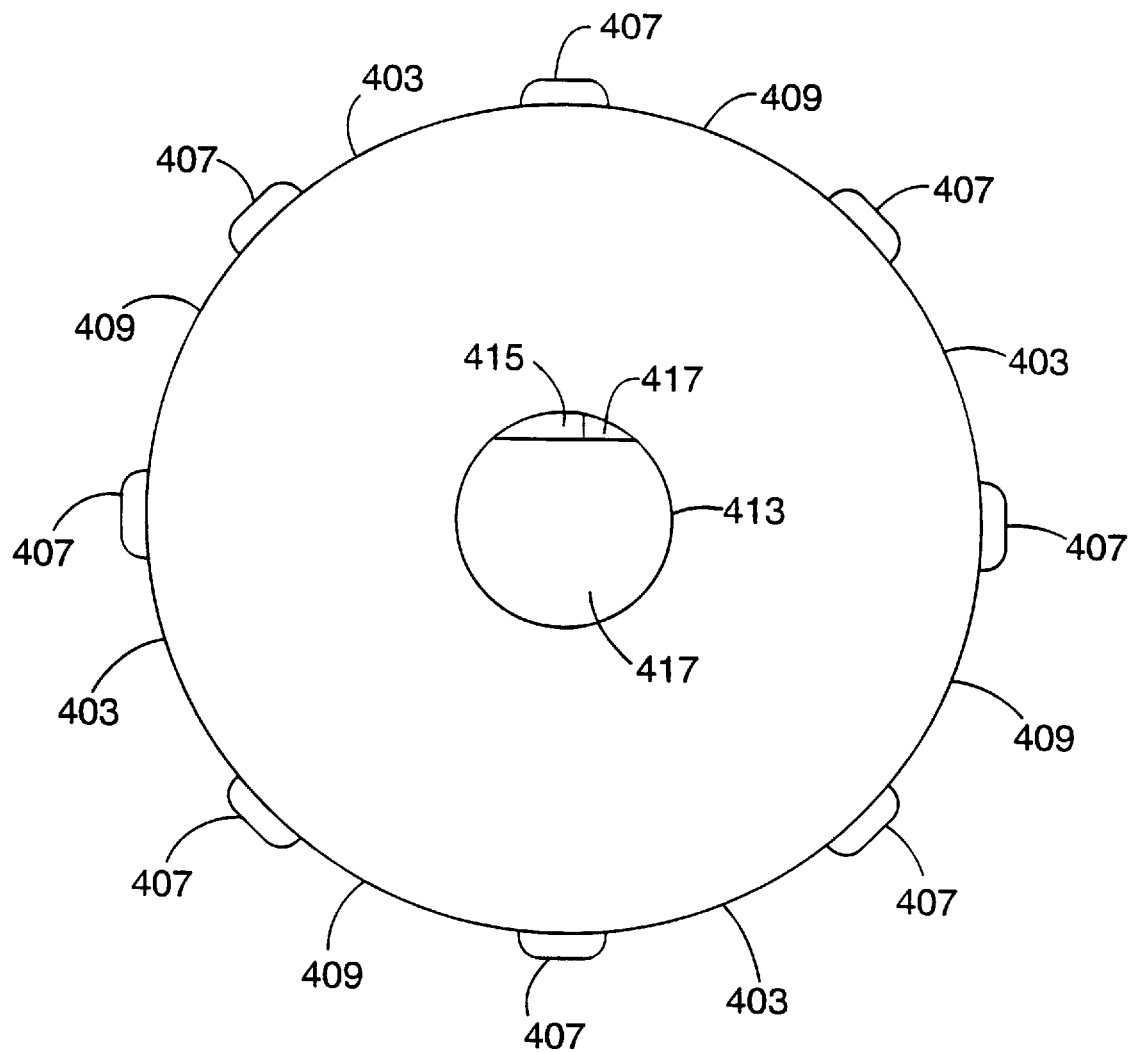
FIG. 39 is an end view of the balloon of FIG. 37 in an expanded state.

The balloon 401 is preferably introduced through the arterial bypass cannula 850 of FIGS. 31–36 although any other delivery system may be used. In order to pass the balloon 401 through the arterial bypass cannula 850, the balloon 401 may be temporarily folded or wrapped around the shaft so that the balloon 401 fits through the arterial bypass cannula 850. Once the balloon 401 passes through the arterial bypass cannula 850, the balloon 401 assumes the collapsed shape of FIG. 38 so that the low friction portions 403, which are at the radially outward positions, engage the body passageway. The balloon 401 is then advanced in the patient to the desired location, such as the ascending aorta, and the balloon 401 is inflated. Referring to FIG. 39, an end view of the balloon 401 is shown with the balloon 401 in an inflated condition. When the balloon 401 is expanded, the high friction portions 405 evert and are exposed for anchoring the balloon 401. Although it is preferred to provide the selective coating 409 and/or ribs 407, the first portion 403 may include any other friction enhancing feature such as spiral ribs, knobs, cross-hatching, or a fine mesh. Furthermore, the first and second portions 403, 405 are preferably integrally formed, however, the first and second portions 403, 405 may be fabricated separately and attached to one another. The balloon 401 is mounted to a shaft 413 having an inflation lumen 415, an infusion lumen 417 and a pressure lumen 419 which are used in the manner described above when occluding the ascending aorta. The balloon 401 may, of course, be used in conjunction with any other catheter design disclosed herein or otherwise known to one of ordinary skill in the art.

Referring to FIGS. 40 and 41, another preferred balloon 401A is shown wherein like reference numbers are used to represent similar features disclosed in the embodiment of FIGS. 37–39. The first portions 403A are also positioned at radially-outward positions of radially-extending arms 411A. The second portions 405A extend between the first portions 403A and include a plurality of ribs 407A and a high friction portion 409. When the balloon 401A expands, the second portions 405A evert so that the balloon 401A assumes a substantially cylindrical cross-section as shown in FIG. 39 with the both the low friction portions 403A and high friction portions 409 exposed.

Figure 42:
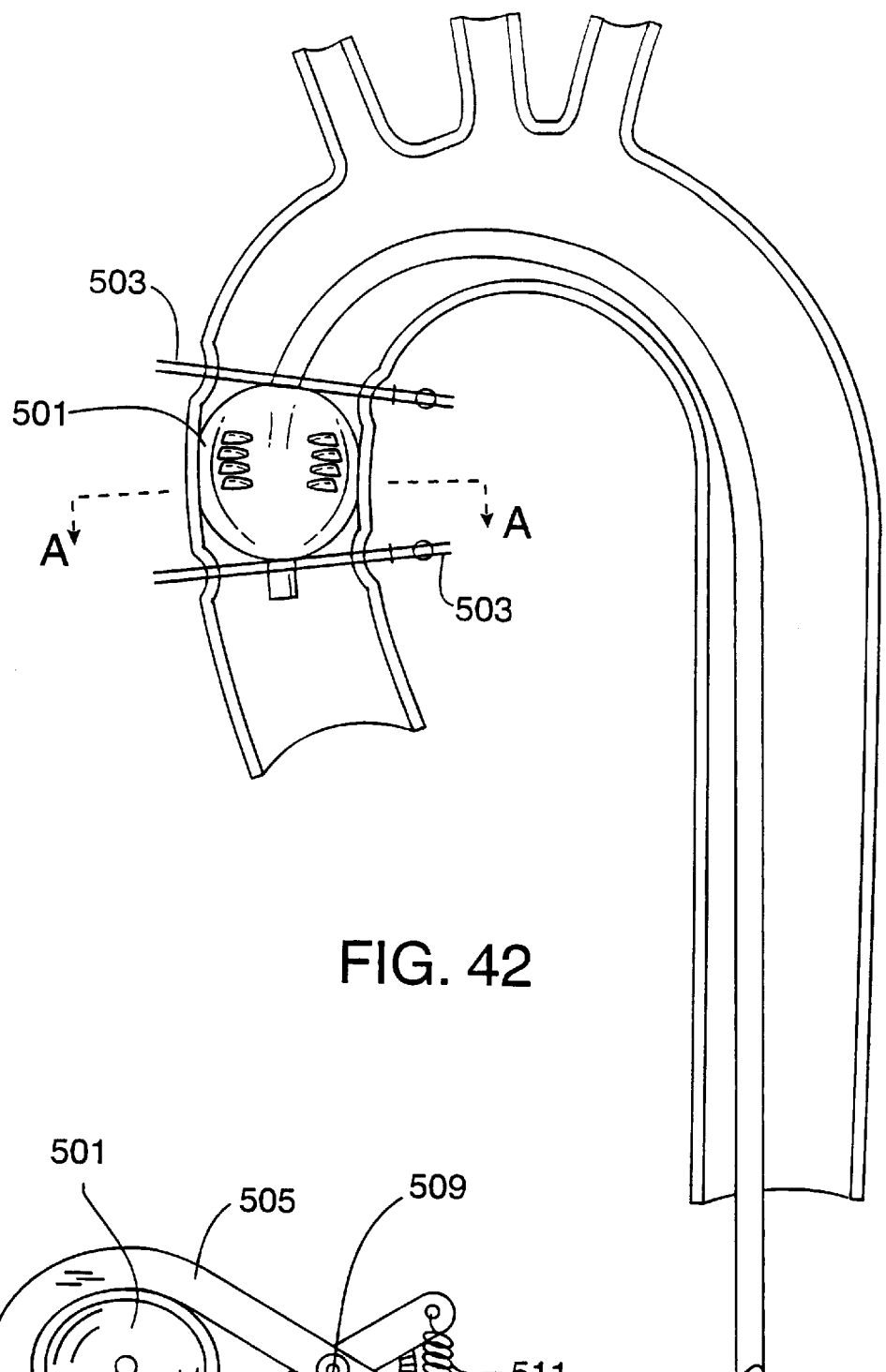
FIG. 42 is a side view of an aorta with clamps positioned on both sides of the occluding member to prevent migration of the occluding member.

Referring to FIG. 42, another preferred method of anchoring the balloon is shown. A balloon 501 is positioned in the ascending aorta with clamps 503 positioned on both sides of the balloon 501 for anchoring the balloon 501 in the aorta. Each clamp 503 is sized to slightly compress the aorta so that the balloon 501 cannot pass by the clamp 503 when the balloon 501 is inflated. Although it is preferred to provide two clamps 503, a clamp 503 having two pairs of jaws may also be used. Furthermore, although it is preferred to provide clamp 503 on both sides of the balloon 501, a single clamp 503 may be used if migration in only one direction is a problem. When using only one clamp 503 which prevents upstream migration of the balloon, the catheter shaft may be tensioned to prevent downstream migration. The clamps 503 may be used in conjunction any of the occluding members described herein or with any other conventional occluding member such as mechanically deployed occluding members.

Figure 43:
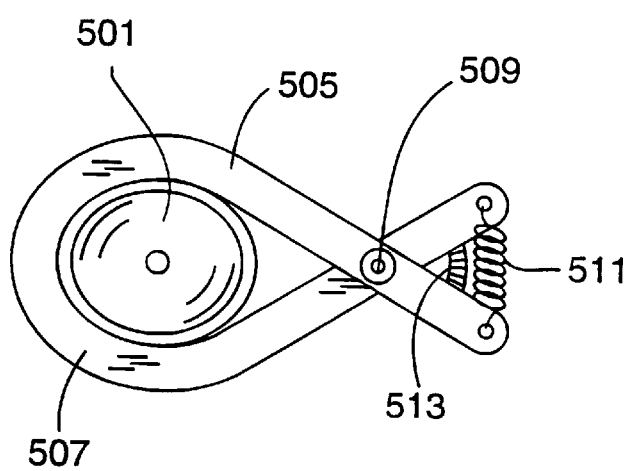
FIG. 43 is a plan view of the clamp of FIG. 42.

Referring to FIG. 43, a plan view of the clamp 503 is shown. The clamp 503 may also be any of the clamps disclosed in pending U.S. patent application Ser. No. 08/567,996 by inventors Donlon et al., filed Dec. 4, 1995, Attorney Docket No. TTC No. 14635-42/Heartport No. 039-CP, which is incorporated herein by reference. The clamp 503 includes jaws 505, 507 pivotally coupled together at a pivot 509. The jaws 505, 507 are biased open by a spring 511 and are locked using ratchet 513. As shown, the clamp 503 does not occlude the aorta but merely blocks migration of the balloon 501. A deploying mechanism (not shown) is used to deploy and retrieve the clamp 503.

Figure 44A:
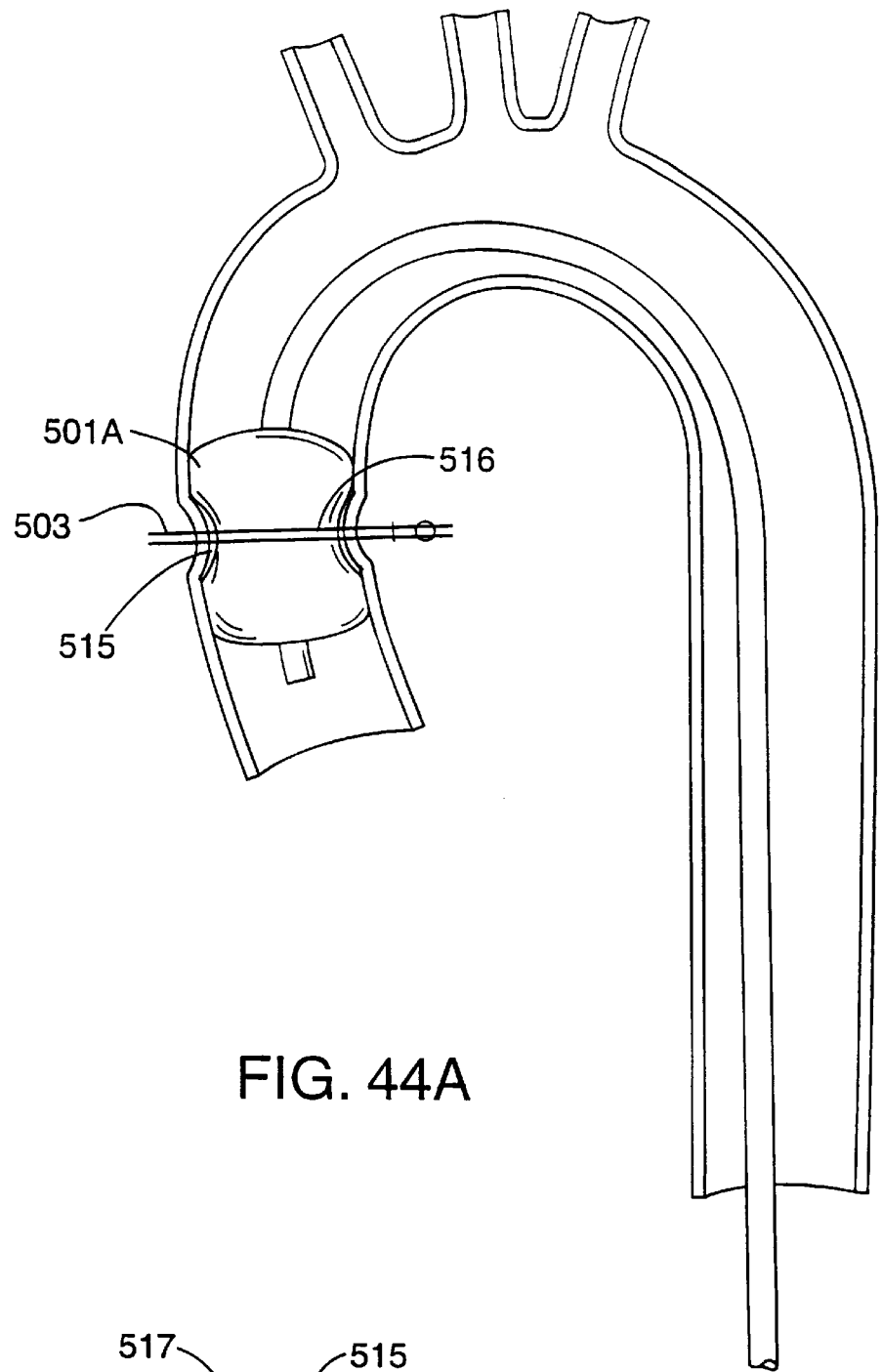
FIG. 44A is a side view of an aorta with the clamp of FIG. 42 positioned around the aorta and a balloon trapped by the clamp in the aorta.
Figure 44B:
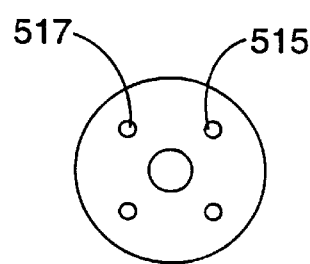
FIG. 44B is a plan view of an intermediate wall positioned in an indentation of the balloon of FIG. 44A.

Referring to FIG. 44A, another preferred method of anchoring an occluding member is shown. The occluding member is preferably a balloon 501A having an hour-glass shape with the clamp 503 positioned around an indentation 515 for anchoring the balloon 501A in both directions. The balloon 501A preferably includes an inner wall 516 at the indentation 515. Referring to FIG. 44B, the inner wall 516 has holes 517 therethrough for pressure communication between both sides of the inner wall 516. The inner wall 516 is preferably inelastic or at least less elastic than the balloon material so that the cross-sectional shape of the balloon 501A at the indentation remains substantially the same after the balloon 501A has been inflated. The clamp 501A is preferably sized to slightly compress the balloon 501A. An advantage of the embodiment of FIG. 44A is that the cooperation of the balloon 501A and clamp 503 requires less distention or compression of the aorta than would otherwise be necessary when using only a clamp or balloon. Minimizing the overall deflection of the aorta may advantageously minimize plaque release.

Figure 45:
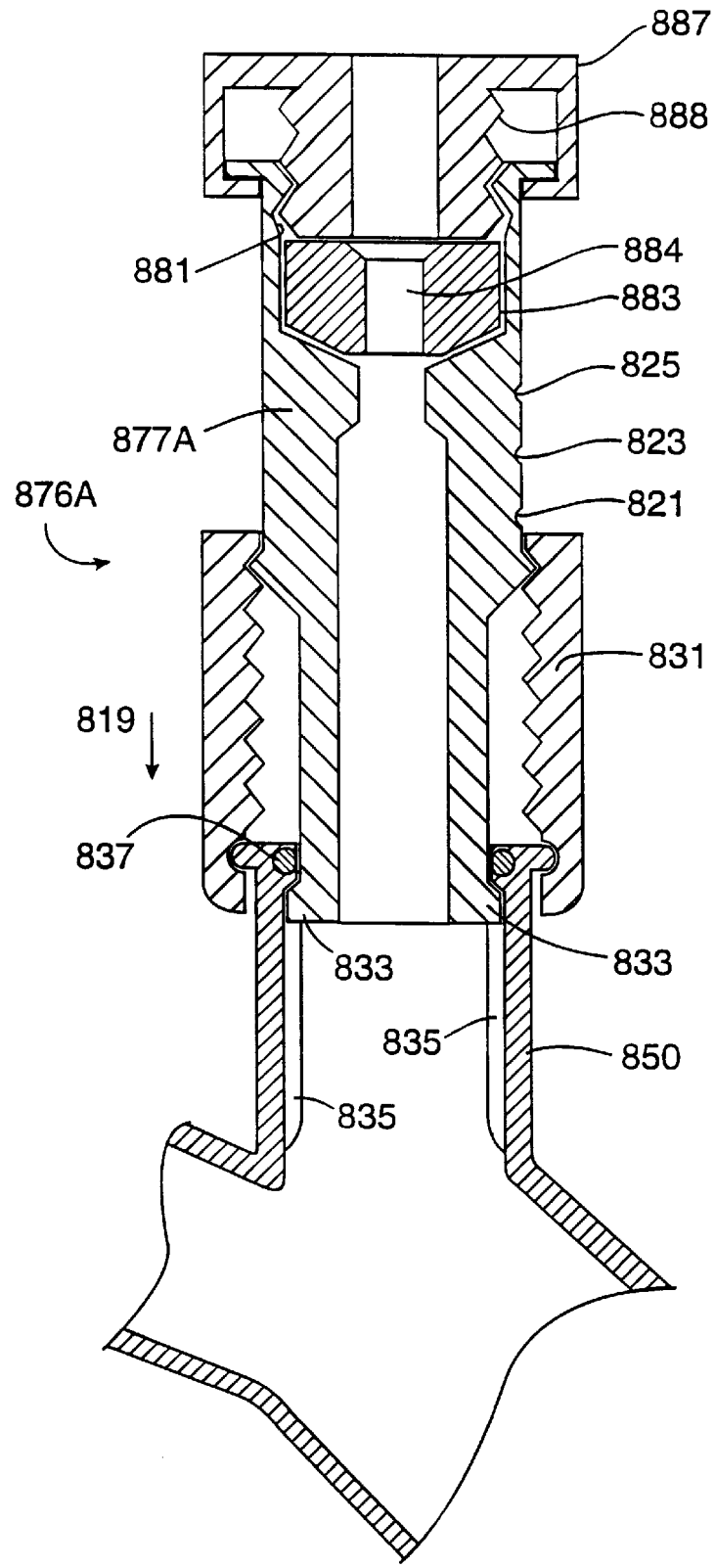
FIG. 45 is a partial cross-sectional view of the delivery cannula of FIGS. 33 and 34 with a shaft displacing mechanism.

Referring to FIG. 45, a partial cut-away of another valve 876A for use with the cannula 850 is shown. Similar reference numbers are used to represent similar items presented in previously described embodiments and discussion of the similar items is omitted here. A shaft displacing mechanism is coupled to the valve 876A for displacing a catheter shaft positioned therein. As will be discussed in further detail below, the shaft displacing mechanism facilitates displacing the shaft so that the shaft engages the body passageway for anchoring the shaft which, in turn, anchors the occluding member. The shaft displacing mechanism can move in an inward direction, defined by arrow 819, and an outward direction opposite to the inward direction. The shaft displacing mechanism may be used with any catheter and is particularly useful when used in conjunction with the shafts described below in connection with FIGS. 46–49.

Referring still to FIG. 45, a threaded coupling 831 couples body 877A to the remainder of the cannula 850 which is described in connection with FIGS. 31–36. The body 877A includes lips 833 which engage slots 835 in the cannula 850. The lips 833 and slots 835 permit axial displacement of the body 877A but prevent rotation of the body 877A when the threaded coupling 831 is rotated. An o-ring 837 seals a space between the body 877A and cannula 850 so that fluid does not pass therebetween. The threaded coupling 831 has threads which engage the body 877A so that rotation of the threaded coupling 831 displaces the body 877A axially. In this manner, a shaft (not shown) which is positioned within the delivery cannula is displaced upon rotation of the coupling 831. The body 877A also preferably includes first, second and third indicators 821, 823, 825 which are described in further detail below in connection with operation of the displacement mechanism. A spring (not shown) may also be provided to preload the shaft in the inward or outward directions. A spring-loaded mechanism would preferably include a displacement stop to limit displacement of the shaft if forces on the shaft exceed the spring preload.

Figure 46:
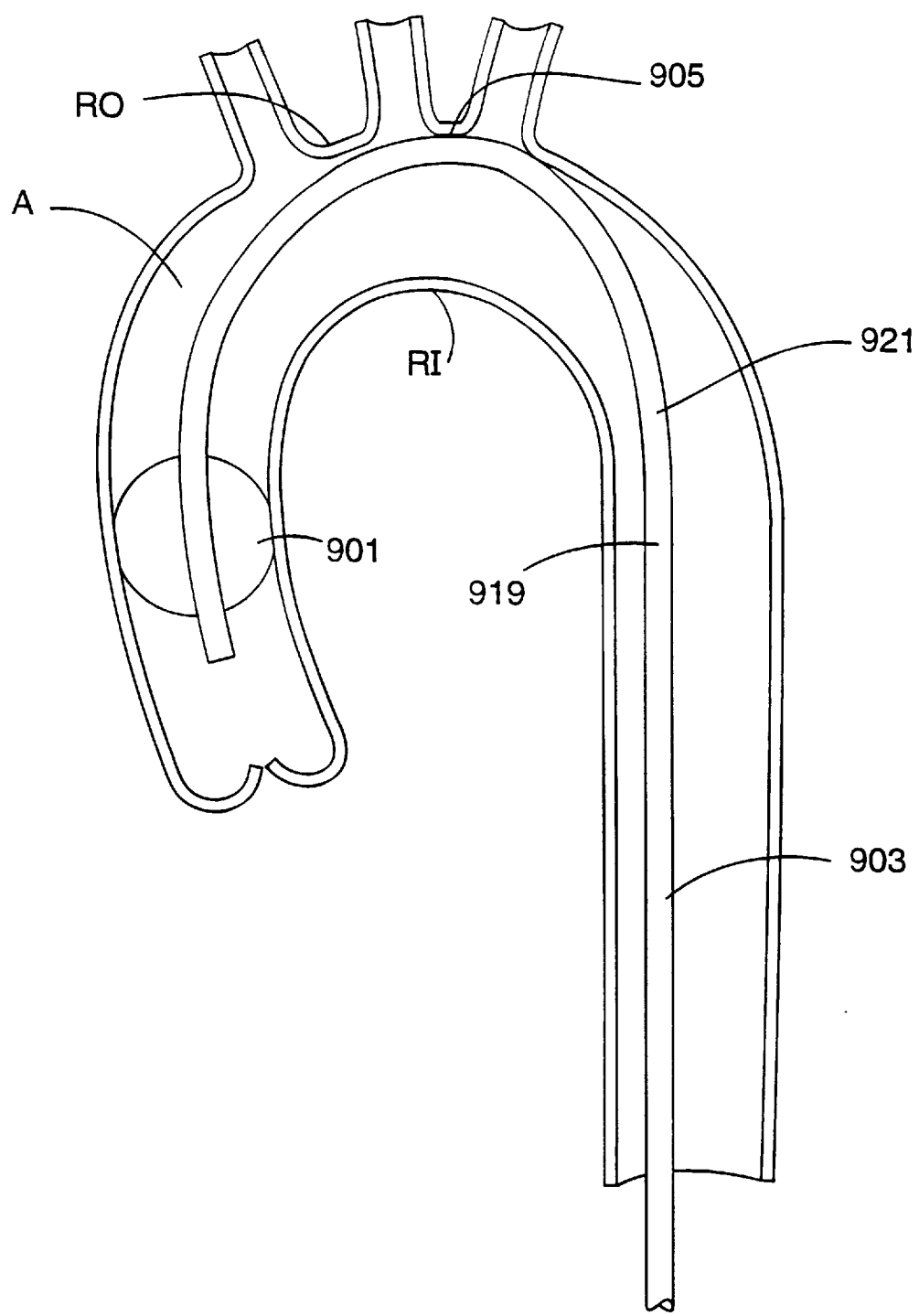
FIG. 46 is a side view of an aorta with the shaft displaced in an outward direction so that the shaft engages a radially inner wall of the aorta.

Referring now to FIGS. 45–49, operation of the delivery cannula 850 and valve 876A is now described. The threaded coupling 831 is initially registered with the second, intermediate indicator 823 so that the threaded coupling 831 can be moved either inward or outward. After the shaft 903 is inserted into the patient and the occluding member 901 is positioned at the desired location, such as the ascending aorta A, the occluding member 901 is expanded to occlude the aorta as shown in FIG. 46. At this time, the pressure forces in the aorta tend to force the occluding member 901 in the upstream direction. To resist the pressure forces on the occluding member 901, the threaded coupling 831 is rotated so that the shaft 903 is moved in the inward direction. The third indicator 825 helps the user determine the desired displacement of the shaft 903 in the inward direction. A preferred range for the predetermined displacement is between 1 and 5 cm, and more preferably between 2 and 4 cm, from the second indicator 823. When the shaft is displaced in the inward direction, a first portion 905 engages the radially outward wall RO. The shaft 903, which now engages the aortic lumen, anchors the occluding member 901 against upstream migration. The shaft 903 and occluding member 901 are preferably made of the same materials and have the same dimensions as the embodiments described above in connection with FIGS. 10–30.

Figure 47:
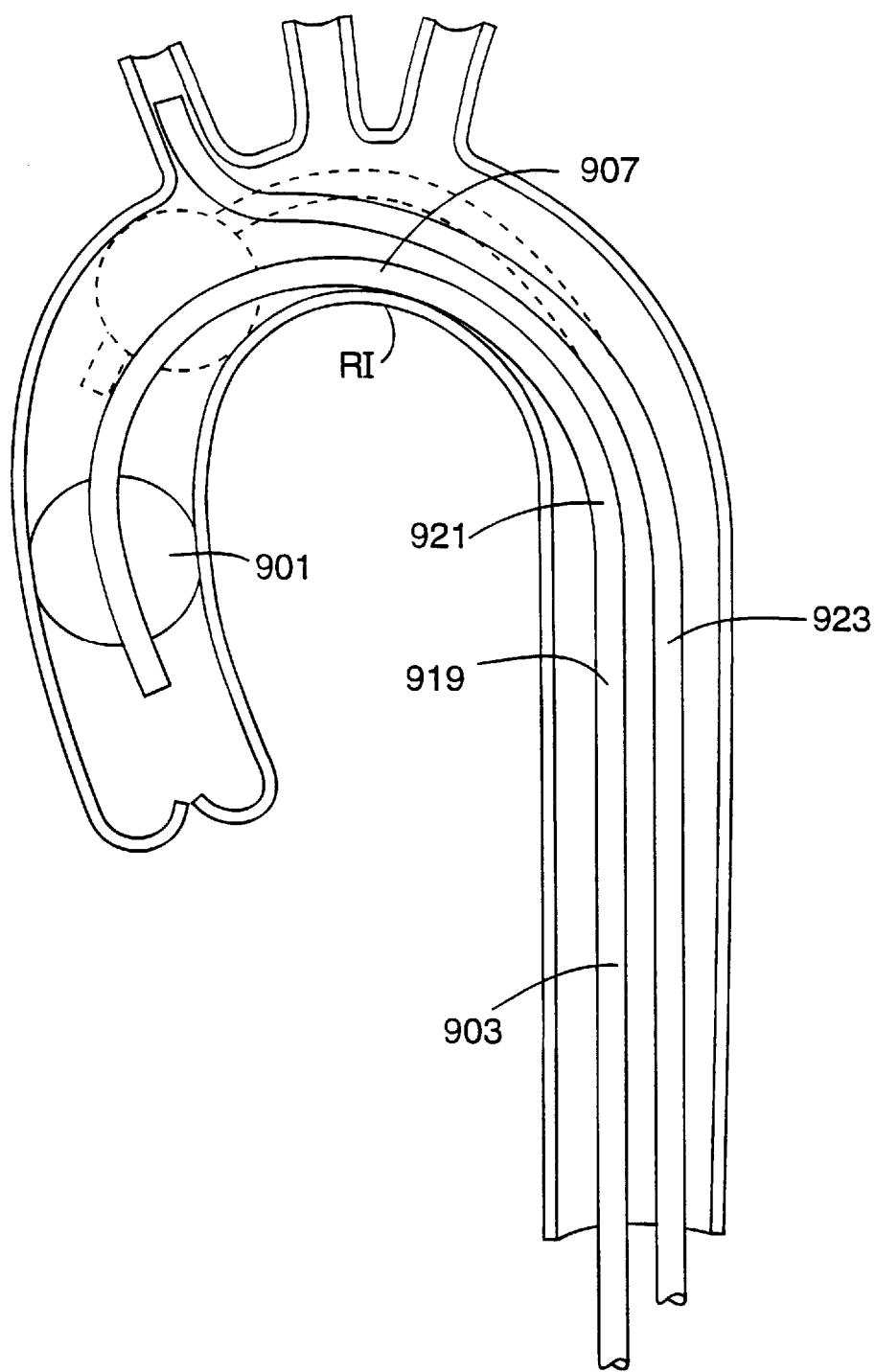
FIG. 47 is a side view of an aorta with a shaft having a two-bend configuration displaced in an inward direction so that the shaft of FIG. 46 engages a radially outer wall of the aorta.

After cardiopulmonary bypass is established, the pressure forces at this time tend to force the balloon in the downstream direction. To resist these forces, the threaded coupling 831 is rotated so that the shaft 903 moves in the outward direction. The first indicator 821 provides a predetermined displacement in the outward direction which is preferably between 1 and 6 cm, and more preferably between 2 and 4 cm, relative to the second indicator 823. Referring to FIG. 47, a second portion 907 of the shaft 903 engages the radially inner wall RI of the aortic lumen. The second portion 907 is preferably the radially inner wall of the hook-shaped portion. Although it is preferred to provide the indicators 821, 823, 825, the threaded coupling 831 and body 877A may be sized so that the maximum displacements match the desired displacements. Furthermore, although it is preferred to provide a threaded displacement mechanism, any other conventional connection may be used such as a bayonet connection, a ratchet and pawl, or a slidable connection with a frictional lock.

Figure 48:
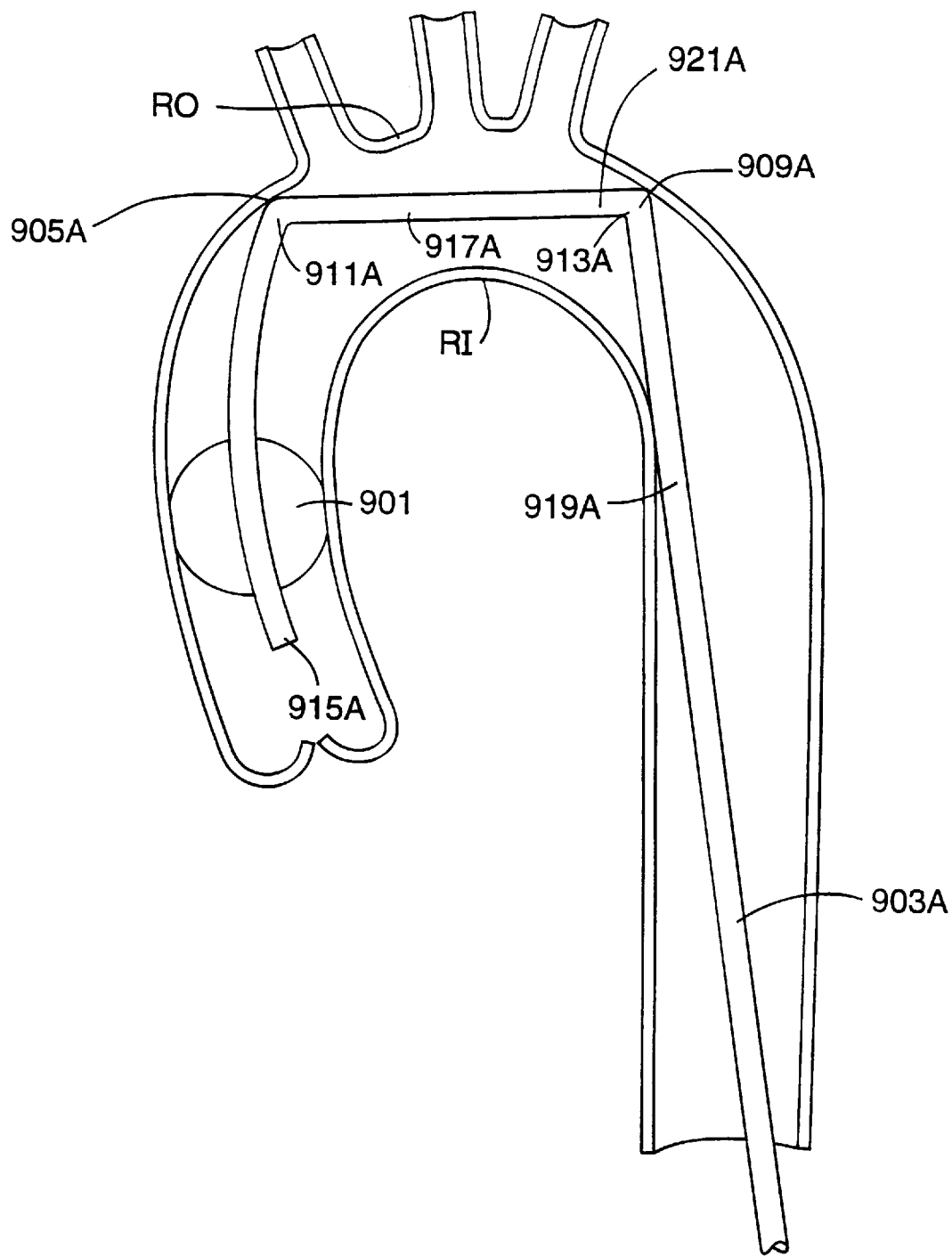
FIG. 48 is a side view of an aorta with a shaft having a hook-shaped portion displaced in an outward direction so that the shaft engages a radially inner wall of the aorta.
Figure 49:
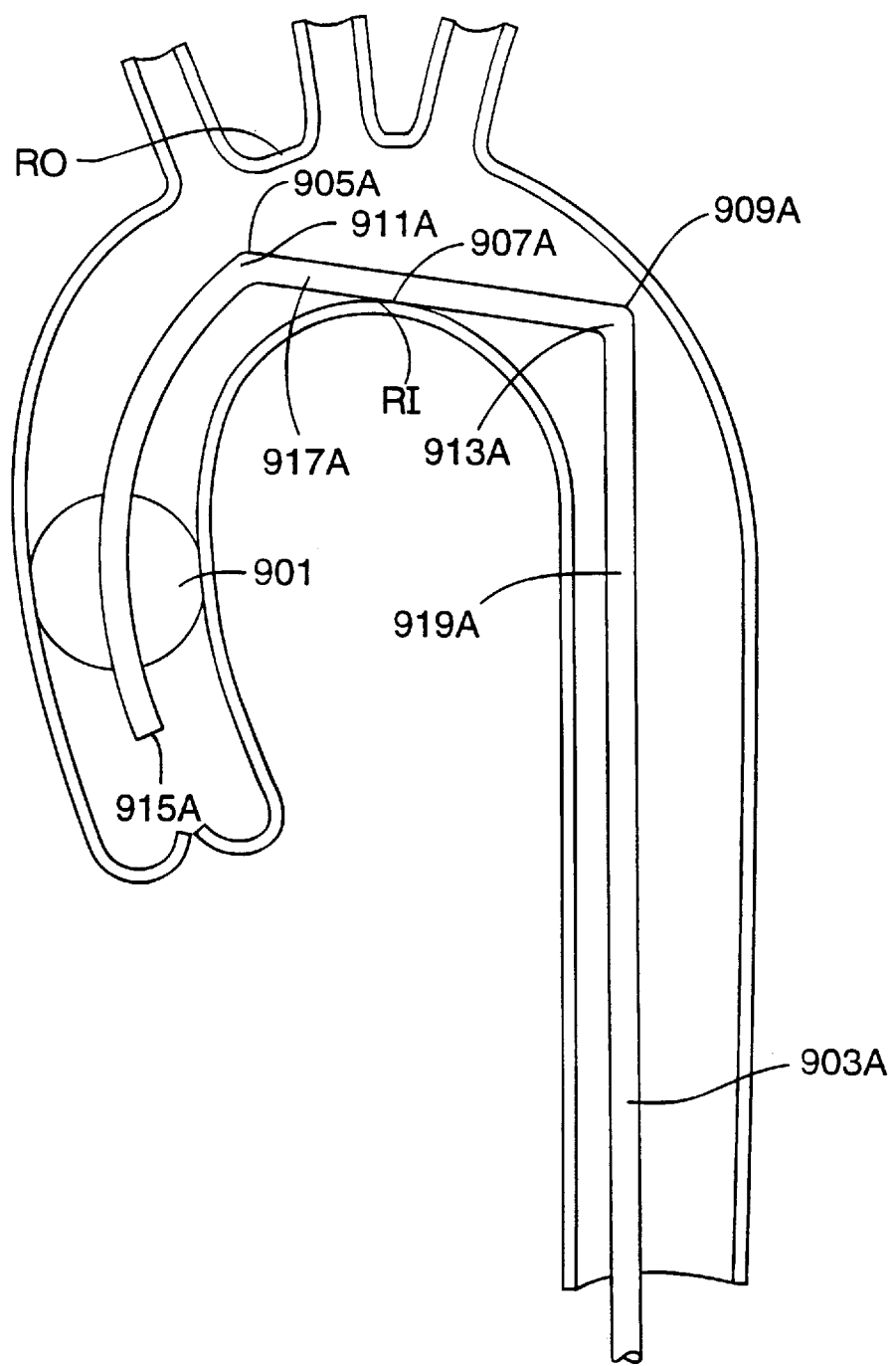
FIG. 49 is a side view of an aorta with the shaft of FIG. 48 displaced in an inward direction so that the shaft engages a radially outer wall of the aorta.

Referring to FIGS. 48 and 49, another preferred catheter is shown. The shaft 903A has a first portion 905A for engaging the radially outer wall RO of the aortic lumen (FIG. 48) and a second portion 907A for engaging the radially inner wall RI of the aortic lumen (FIG. 49). A third portion 909A also engages the radially outer wall RO to further resist balloon migration in the upstream direction. The second and third portions 907A, 909A are positioned at first and second bends 911A, 913A. The first bend 911A is preferably between 3 and 12 cm, and more preferably between 5 and 10 cm, from the distal end 915A. A first substantially-straight section 917A extends between the first and second bends and preferably has a length between 3 and 12 cm, and more preferably between 3 and 8 cm. A second, substantially-straight section 919A extends from the second bend 909A toward the proximal end. Although it is preferred to provide a straight section between the first and second bends 911A, 913A, a curved portion may also be provided.

The embodiments of FIGS. 46–49 preferably include a relatively stiff proximal section 919, 919A and a flexible distal section 921, 921A connected to the proximal section. Referring to FIGS. 46–47, the proximal section 919 is substantially straight and the distal section 921 includes the hook-shaped portion. Referring to FIGS. 48 and 49, the proximal section 919A preferably terminates just before the first bend 909A in FIG. 48 while the distal section 921A includes the first and second bends 911A, 913A. The proximal section 919, 919A limits migration of the balloon by limiting the overall deflection of the proximal end of the catheter. The distal section 921, 921A preferably has a lower stiffness than the proximal section 919, 919A so that the distal section 921, 921A may conform somewhat to the shape of the aortic arch. The distal section 921, 921A preferably extends between 10 and 20 cm and more preferably between 10 and 15 cm from the proximal portion to the distal end 915A. The proximal section 919, 919A preferably extends between 40 and 100 cm, and more preferably between 80–90 cm, from the distal section 921, 921A toward the proximal end. The flexible and distal sections 919, 919A, 921, 921A may be coupled together by any conventional method or may be integrally formed with the distal section 921, 921A being formed with a smaller, more flexible cross-sectional shape than the proximal portion 919, 919A or with the proximal section having reinforcing ribbon, wires and the like. The first and second portions 905, 907 also preferably include a frictional coating or surface to further enhance anchoring.

Referring again to FIG. 47, yet another method of anchoring an occluding member in the ascending aorta is shown. An anchor 923, which is preferably a perfusion catheter, is introduced into the patient and advanced into the brachiocephalic artery. The anchor 923 is coupled to the cardiopulmonary bypass system (see FIG. 1) for delivering oxygenated blood to the brachiocephalic artery during cardiopulmonary bypass. The anchor 923 advantageously limits migration of the occluding member 901 and ensures oxygenated blood reaches the brachiocephalic artery. Thus, the occluding member 901 of FIG. 47 is anchored against downstream migration by engagement between the second portion 907 and the radially inner portion RI of the aortic arch and the occluding member 901 is anchored against upstream migration by the anchor 923. The dotted line position of the occluding member 901 illustrates brachiocephalic anchor 923 blocking upstream migration of the occluding member 901. Although it is preferred to provide a separate anchor 923, the brachiocephalic anchor may be coupled to the balloon catheter and deployed therefrom. Furthermore, although it is preferred to use the anchor 923 to prevent migration of the occluding member 901, the brachiocephalic anchor may simply be a thin shaft which resists migration of the occluding member while permitting an adequate flow of oxygenated blood into the brachiocephalic artery.

Figure 50:
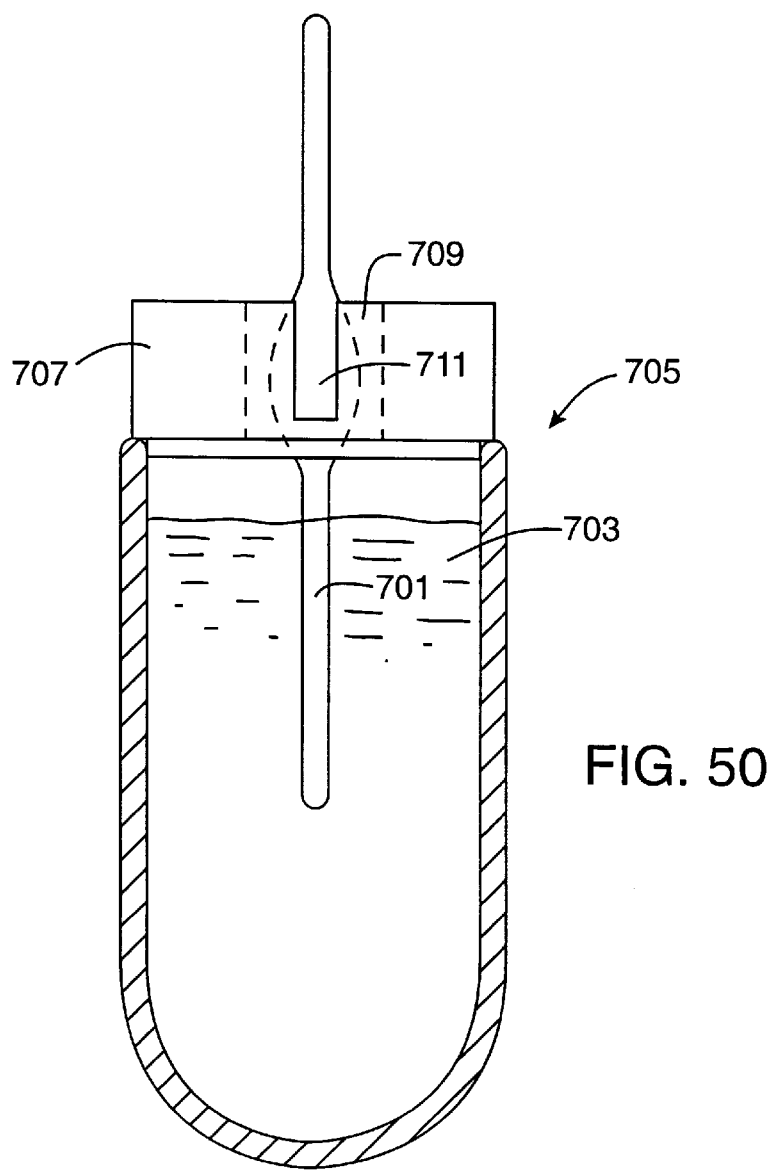
FIG. 50 is a partial cross-sectional side view of a container containing a solution and a mandrel partially submerged in the solution.

Referring to FIG. 50, a preferred apparatus for forming an asymmetric balloon is shown. A solution 703 is contained in a container 705 having a vapor trap 707. The container 705 is shown in cross-section for clarity. The vapor trap 707 has an open upper end 709 and a side slot 711. The balloon (not shown) is formed by dipping a mandrel 701 in the solution 703 which, when hardened, forms the balloon.

The solution 703 may be any solution mentioned above or any other suitable solution which forms an elastic or inelastic balloon. The solution preferably comprises a solute and a suitable solvent. The solvent is used to reduce the viscosity of the solute. When the mandrel 701 is withdrawn from the solution, the solvent vaporizes thereby leaving the solute on the mandrel. The solute may be a polyurethane, PVC or any suitable elastomer mentioned above and is preferably polytetramethylene glycol ether which can be purchased from Dow under the name Dow 2363 PELLETHANE 80AE. The solvent may be any solvent which reduces the viscosity of the solute and is preferably THF when the solute is Dow 2363 PELLETHANE 80AE.

Figure 51:
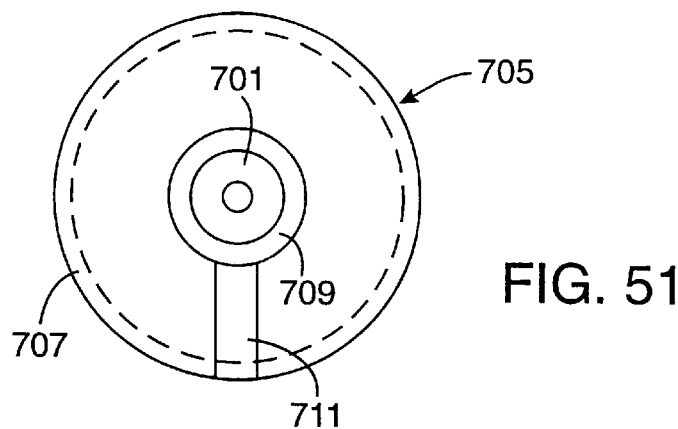
FIG. 51 is a plan view of the container and mandrel of FIG. 50.

The mandrel 701 is dipped into the solution 703 and withdrawn from the container 705 at a relatively slow rate, preferably about 4 in./min, through the open upper end 709. As the mandrel 701 is withdrawn, part of the solution 703 coating the mandrel 701 flows down the mandrel 701 and back into the container 705. The portion of the mandrel 701 exposed to the slot 711 cures faster than the other portions of the mandrel 701 due to exposure to the ambient atmosphere. Vaporization of the solution 703 on the portion of the mandrel 701 passing adjacent slot 711 increases the viscosity of the solution. The increased viscosity reduces the amount of solution 703 which flows down the mandrel and back into the container 705 thereby producing a thicker balloon wall along the portion of the mandrel 701 passing adjacent the slot 711. As will be discussed below in connection with FIGS. 52–55, the differing balloon wall thickness causes the balloon to expand asymmetrically. Although it is preferred to use the vapor trap 707 having the slot 711 to promote differential wall thickness, the differential wall thickness may be provided by tilting or spinning the mandrel 701, uneven spraying or dipping of the mandrel 701, and/or a dynamic, forced gas circulation rather than the passive evaporation of FIGS. 50 and 51. The mandrel 701 is preferably dipped and withdrawn from the solution 703 a number of times; preferably at least four and more preferably at least seven times. After each application, the thickness of the balloon increases with the thickest portion passing adjacent the slot 711. Although it is preferred to pass the same portion of the balloon adjacent the slot, the balloon may be rotated between successive dippings so that a larger portion of the balloon has a thicker wall portion.

Figure 52:
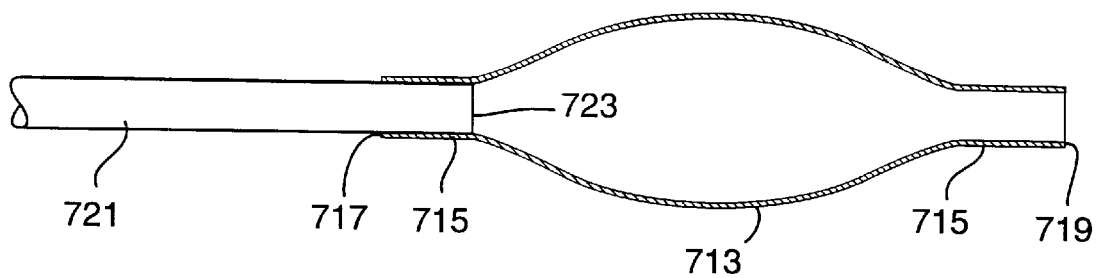
FIG. 52 is a cross-sectional view of a distal end of a balloon connected to a distal end of a shaft.
Figures 53, 54:
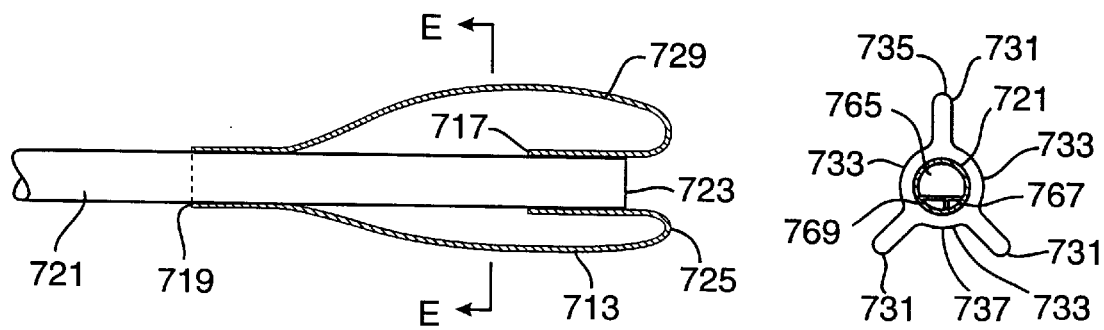
FIG. 53 is a cross-sectional view of the balloon of FIG. 52 with the proximal end of the balloon connected to the shaft and the balloon in a collapsed position.
FIG. 54 is a cross-sectional view of the balloon of FIG. 53 along line E—E.

After the mandrel 701 has been dipped the desired number of times and the balloon has cured on the mandrel 701, the balloon is removed from the mandrel 701. Referring to FIG. 52, the balloon 713 is cut so that the balloon 713 has two substantially cylindrical extensions 715 on distal and proximal ends 717, 719. The distal end 717 of the balloon 713 is preferably heat bonded to a shaft 721 but may be bonded to the shaft 721 in any other manner such as solvent or adhesive bonding. The shaft 721 is preferably the same as described above in connection with FIGS. 10C and preferably has first, second and third lumens 765, 767, 769 as shown in FIG. 54 with the first lumen being used for inflating the balloon 713, the second lumen 767 being configured to deliver a fluid distal to the balloon 713, and the third lumen 769 being used for sensing pressure distal to the balloon 713. Although it is preferred to provide the third lumen 769 for sensing pressure distal to the balloon 713, the shaft may include the pressure transducers described above in connection with balloon anti-migration features without departing from the scope of the invention.

Referring to FIG. 53, after the distal end 717 of the balloon 713 is attached to a distal end 723 of the shaft 721, the balloon 713 is inverted so that the proximal end 719 is positioned around the shaft 721. The proximal end 719 is then attached to the shaft 721, preferably by heat bonding. The balloon 713 is shown in the collapsed position in FIG. 53 with a distal tip 725 of the balloon 713 extending beyond a distal tip 727 of the shaft 721 so that a bumper 729 is formed. The bumper 729 advantageously minimizes damage to the body passage through which the catheter is fed by preventing contact between the distal tip 727 of the shaft 721 and the body passage. Although it is preferred to invert the distal end 717 of the balloon 713 to form the bumper 729, the bumper 729 may also be formed without inverting the distal end of the balloon 713 so long as a portion of the balloon 713 extends beyond the distal tip 727 of the shaft 721 when the balloon 713 is in the collapsed position.

Referring again to the cross-sectional view of FIG. 54, the balloon 713 preferably has three radially extending arms 731 when in the collapsed position. As discussed above in connection with the balloons of FIGS. 37–41, the balloon 713 preferably includes high friction portions 733 between the radially extending arms 731 so that when the balloon 713 is inflated the high friction portions 733 are exposed for anchoring the balloon 713 in a body structure. The high friction portion 733 may be any of the features discussed above in connection with FIGS. 37–41. An advantage of the balloon 713 is that the balloon 713 is inverted after formation so that the high friction portion 733 can be a coarse coating on the mandrel 701 which, when everted, provides the high friction portions 733. A thick wall portion 737 of the balloon 713 lies between two of the radially extending arms 731 and a thin wall portion 735 essentially forms one of the radially extending arms 731.

Figure 55:
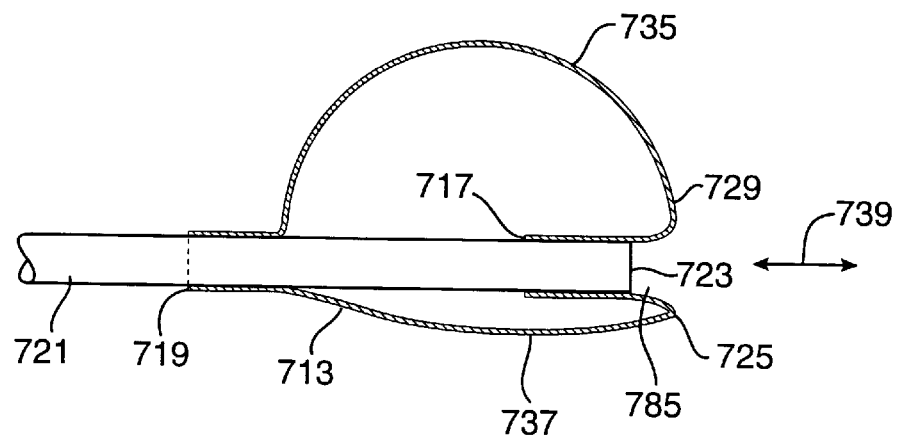
FIG. 55 is a cross-sectional view of the balloon of FIG. 53 in an expanded position.

Referring to FIG. 55, a cross-sectional view of the balloon 713 is shown with the balloon 713 in the expanded position. The thick wall portion 737 does not expand as much as the thin wall portion 735 thereby giving the balloon 713 an asymmetrical shape with respect to a longitudinal axis 739 of the shaft 721. The balloon is preferably substantially circular so that the balloon 713 is also positioned eccentrically on the shaft 721 as well as asymmetrically. The balloon 713 preferably extends beyond the distal tip 727 of the shaft 721 when the balloon 713 is in the expanded position so that the bumper 729 still prevents the shaft 721 from contacting the body structure through which the catheter is introduced. The bumper 729 also prevents damage to the aortic valve if the balloon 713 migrates toward the aortic valve.

The balloon 713 forms a recess 785 around the distal tip 723 of the shaft 721 for venting gasses from the ascending aorta. The patient is preferably tilted head up when venting gasses from the ascending aorta so that the gasses pool in the recess for venting through any of the lumens 765, 767, 769 in the shaft 721.

Figure 56:
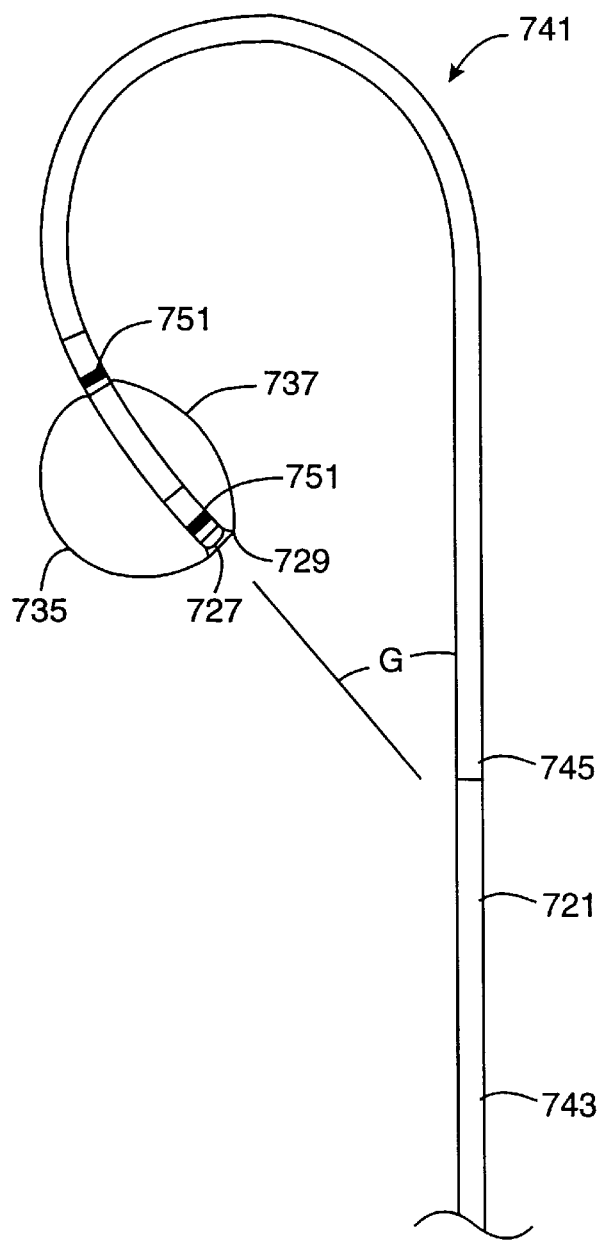
FIG. 56 is a side view of the distal end of the shaft with the balloon of FIGS. 53–55 in the expanded position.

Referring to FIG. 56, a distal end 741 of the shaft 721 is shown. The distal end 741 of the shaft 721 is generally configured like the catheter of FIGS. 12A–12C and has a hook shape. The distal end 741 generally conforms to the shape of the ascending aorta and preferably has a radius of curvature between 0.5 inch and 10 inches and more preferably between 0.5 and 5.0 inches. The thick wall portion 737 is preferably positioned at a radially inner position on the curved distal end 741 of the shaft 721 while the thin wall portion 735 is preferably positioned at a radially outer position on the curved distal end 741 of the shaft 721. By positioning the balloon 713 in this manner, the distal tip 727 is positioned away from the wall of the ascending aorta thereby minimizing the likelihood that the distal tip 727 contacts the wall of the ascending aorta. The distal tip is preferably oriented at an angle G of between 15° and 60° and most preferably 38° with respect to a substantially straight proximal portion 743.

The distal end 741 of the shaft 721 preferably has an increased stiffness to prevent kinking. The distal end 741 preferably extends at least 10 cm from the balloon 713, more preferably at least 15 cm, and most preferably at least 25 cm toward the proximal end 743 from the balloon 713. The stiff portion preferably extends throughout the curved distal end 741 of the shaft 721 so that the distal end 741 has a higher stiffness than the proximal portion 743. The increased stiffness is preferably provided with a surlyn shrink tube 745 or a polyolefin shrink tube which is heat shrunk over the shaft 721 at the distal end. The shrink tube 745 increases the stiffness of the distal end 741 relative to the proximal portion 743. The increased stiffness may be provided by any other method such as a pulse extrusion where the distal end 741 of the shaft 721 has a greater wall thickness than the proximal portion 743.

Figure 57:
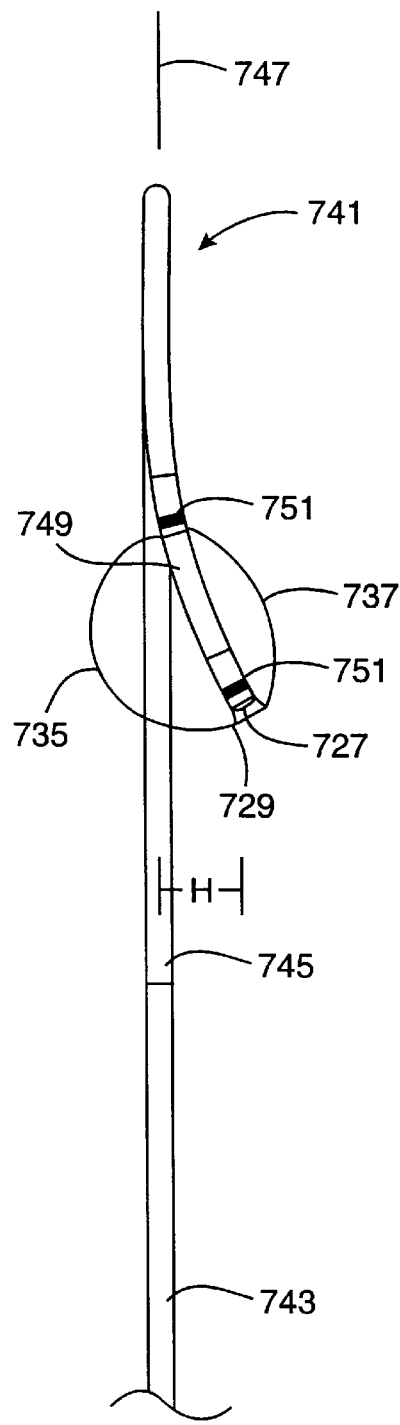
FIG. 57 is another side view of the distal end of the shaft and balloon of FIG. 56.

Referring to FIG. 57, the balloon 713 is also asymmetrically positioned with respect to the shaft 721 in a transverse plane 747. The proximal portion 743 and distal end 741 of the shaft 721 lie in substantially the transverse plane 747 with an offset portion 749 at the distal end 741. The shaft 721 has an offset H relative to the proximal portion 743. The thick wall portion 737 of the balloon 713 is positioned in the direction of the offset A thereby providing a smaller balloon thickness in the direction of the offset A when the balloon 713 is expanded. The catheter also includes balloon markers 751 which are visible during fluoroscopic imaging. The markers 751 are used to position the balloon 713 in the ascending aorta and also detect balloon 713 migration after inflation. Any other conventional imaging method may also be used.

Figure 58:
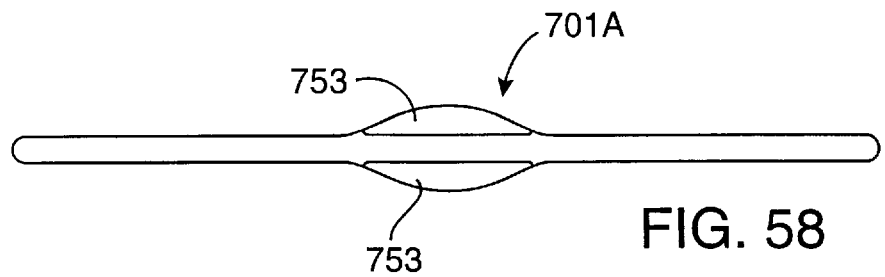
FIG. 58 is a side view of another mandrel used for forming an asymmetric balloon.
Figure 59:
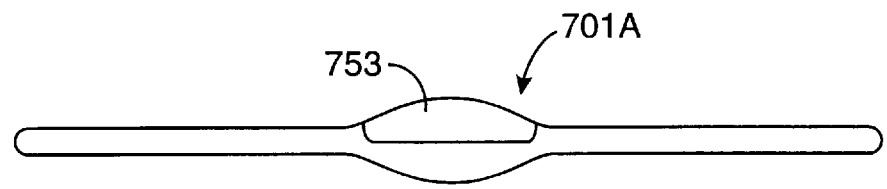
FIG. 59 is another side view of the mandrel of FIG. 58.
Figure 60:
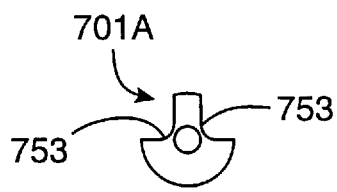
FIG. 60 is an end view of the mandrel of FIGS. 58 and 59.
Figure 61:
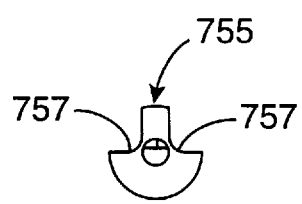
FIG. 61 is a cross-sectional view of a balloon manufactured with the mandrel of FIGS. 58–60 with the balloon in a partially expanded shape.
Figure 62:
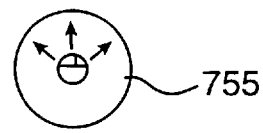
FIG. 62 is a cross-sectional view of the balloon of FIGS. 58–60 with the balloon in a more fully expanded shape.
Figure 63:
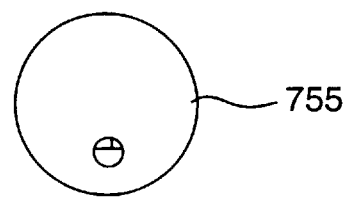
FIG. 63 is a cross-sectional view of the balloon of FIGS. 58–60 with the balloon in the expanded shape.

Referring to FIGS. 58–60, another apparatus for providing an asymmetric balloon is shown. A mandrel 701A is provided which has two longitudinal cut-outs 753. The mandrel 701A is dipped in a suitable solution and dried to produce a balloon (not shown). The balloon preferably has a constant balloon thickness, however, a varying balloon thickness may also be provided in any manner described above. Referring to FIG. 61, a cross section of a balloon 755 made with the mandrel 701A is shown in a partially expanded shape. The longitudinal cut-outs 753 form two indented portions 757 when the balloon is in the partially expanded shape. When the balloon is 755 fully collapsed, the balloon 755 preferably forms the radially extending arms of FIG. 54. Referring to FIG. 62, a cross-section of the balloon 755 is shown in a more fully expanded shape with the indented portions 757 everted. Referring to FIG. 63, a cross-section of the balloon 755 is shown in a fully expanded shape. As the balloon 755 expands, the asymmetric shape becomes more exaggerated since the larger side expands faster than the smaller side due to the larger surface area. The balloon 755 also tends to become more asymmetric due to the irregularities in the balloon 755 wall caused by the indented portions 757. The balloon 755 is preferably positioned on a shaft in the manner described above in connection with FIGS. 56–57 with the shaft having the three lumen configuration of FIGS. 10C. Although the above described methods are preferred for providing an asymmetric balloon, the asymmetric balloon may be provided by any other method without departing from the scope of the invention.

Referring to FIGS. 64–65, a partial cross-sectional view of the proximal end of the shaft 721 is shown. The proximal end of the shaft 721 is trifurcated into first, second and third independent shafts 759, 761, 763 which each have a lumen fluidly coupled to the first, second and third lumens 765, 767, 769, respectively. The first independent shaft 759 is preferably coupled to a source of cardioplegic fluid 771, the second independent shaft 761 is preferably coupled to a source of balloon inflation fluid 773, and the third lumen 769 is preferably coupled to a pressure sensor 775 for sensing a pressure distal to the balloon. Luer connections 787 are provided at each of the independent shafts 759, 761, 763.

The trifurcation of the shaft 721 is accomplished in the following manner. The second and third lumens 767, 769 of the shaft 721 are spliced at the proximal end to create openings in each of the lumens 767,769. A teflon rod is then inserted into the second independent shaft 761, through the opening in the second lumen 767, and into the second lumen 767. Another teflon rod is then inserted through the third independent shaft 763, through the opening in the third lumen 769, and into the third lumen 769. The teflon rods ensure that the lumens remain open throughout the trifurcation procedure. The second and third independent shafts 761, 763 are then positioned against the openings in the second and third lumens 767, 769. A TFE sheath is pulled over the junction of the second and third independent shafts 761, 763 and the openings in the second and third lumens 767, 769. The TFE sheath is then inserted between thermal jaws, or any other heating device, and heated to 390° for one minute to fuse the second and third independent shafts 761, 763 to the openings. During the last ten seconds of the heating process the three lumen portion of the shaft 721 and second and third independent shafts 761, 763 are pressed towards one another in the direction of arrows J to ensure that the connection is sealed. The junction of the shafts 761, 763 has a slightly larger profile due to compression of material when the shafts are urged towards one another in the direction of arrows J. The TFE sheath and teflon rods are then removed and the trifurcation thereby completing the trifurcation procedure. The shaft 721 may be trifurcated by any other method without departing from the scope of the invention.

The first lumen 765, which is coupled to the source of cardioplegic fluid 771, extends to a bellows connection 777 which increases the flexibility of the proximal end of the first lumen 765. The increased flexibility permits the surgeons to place the source of cardioplegic fluid, source of balloon inflation fluid, and pressure sensor in convenient locations without kinking the first lumen 765. Although it is preferred to use the bellows 777, the flexibility of the proximal portion of the first lumen 765 may be provided by any other structure so long as the flexibility of the first independent shaft 759 is increased. The bellows 777 preferably deflects at an angle of at least 90° and more preferably at least 135° without kinking.

The bellows 77 is formed from a single lumen tube 779 which is attached to the first lumen 765 of the shaft 721 proximal of the second and third independent shafts 761, 763. The bellows 777 is formed by inserting a teflon rod into the lumen of the single lumen tube 779 to prevent the lumen from collapsing. The single lumen tube 779 is then inserted into a forming cylinder having an inner diameter equal to the desired outer diameter of the bellows 777. The ends of the single lumen tube 779 are then held at two positions on both sides of the forming cylinder 781 and the single lumen tube 779 is then heated and compressed between the two ends so that the tube 779 buckles at a number of locations within the forming cylinder to form the bellows 777. The amount of compression is controlled to form the desired number of bellows 777 folds. The resulting single lumen tube 779 with the bellows 777 is then attached to the first independent shaft using any conventional method. Although it is preferred to provide the bellows 777 for the first lumen, the bellows 777 may also be provided with the second and/or third lumens 767, 769.

Referring to FIG. 66, a cross-sectional view of another preferred cannula 201 is shown. A specific application of the present invention is for arterial and venous cannulas for a cardiopulmonary bypass system. The methods and devices described above in connection with arresting a patient's heart and placing the patient on cardiopulmonary bypass are incorporated here for use with the cannula 201 described below. The cannula 201 includes a body 203 and a reinforced section 205. As will be discussed in greater detail below, the reinforced section 205 has a thin wall which maximizes the lumen size for a given outer diameter.

Referring to FIG. 67, an apparatus for forming the reinforced section 205 is shown. The reinforced section 205 of the cannula 201 is preferably manufactured with an elongate member 207 coated with a coating 209. The elongate member 207 may be made of any suitable material which has the requisite structural characteristics such as stainless steel, nickel titanium, or a polymer. A preferred material is 304V stainless steel wire having a 0.008 inch diameter. The elongate member 207 may have any cross-sectional shape and a preferred shape is circular.

The elongate member 207 is preferably coated with the coating 209 by coextruding the elongate member and the coating 209. Any suitable coating 209 may be used and preferred coatings include polymers and specifically polyurethane, PVC, polyether block amide which can be purchased from Elf Atochem Inc. under the name PEBAX, and styrene block copolymer which can be purchased from Shell under the name KRATON. A preferred polyurethane is polytetramethylene glycol ether which can be purchased from Dow under the name Dow 2363 PELLETHANE 80AE.

The coating 209 is extruded over the elongate member 207 so that the coating 209 has opposing sides 211, 212 which are configured to engage one another when the coated elongate member 207 is wrapped around a mandrel 213. A preferred shape is a quadrangle, and specifically a square, however, any other shape may be used including irregular shapes so long as the opposing sides 211, 212 are configured to engage one another. The square cross-sectional shape preferably has sides having lengths between 0.010 and 0.020 inch and more preferably between 0.010 and 0.015 inch and most preferably 0.014 inch.

The coated elongate member 207 is wrapped around the mandrel 213 in a helical shape. The mandrel 213 is preferably coated with a lubricious coating such as TFE to prevent sticking. An advantage of the present invention over other methods of forming a cannula is that the coating 209 encasing the reinforcing member 207 does not have to flow between adjacent portions of the elongate member 207 since the elongate member 207 is coextruded to have a shape in which the opposing sides 211, 212 already engage one another. A shrink tube (not shown), preferably a heat shrink tube such as a polyolefin or fluorinated ethylene propylene (FEP), may also be positioned around the elongate member 207 to facilitate bonding. The shrink tube is preferably removed after heating. The coated elongate member 207 may also be dipped in a polymer solution such as polyurethane and tetrahydroforan (solvent) to enhance the structural characteristics of the reinforced section 205. Furthermore, the coating or tube may also be applied over the wound coated elongate member. Alternatively, a tube may be positioned over the mandrel 213 and the coated elongate member 207 may be wound over the tube. The reinforced section 205 may be made of more than one layer of the coated elongate member 207 and the coated elongate member 207 may be wrapped in different directions to increase the hoop and tensile strength. Although it is preferred that the elongate member 207 has a constant cross-sectional profile, the elongate member 207 may also have differing sizes to provide stiff and flexible areas.

After the coated elongate member 207 has been wrapped around the mandrel 213, the coated elongate member 207 is heated to melt the coating 209 and fuse adjacent portions of the coating 209 together to form an integrated structure. The coated elongate member 207 is preferably heated using an oven, however, any other heating method may be used including an IR lamp, heating the mandrel 213, or a combination thereof. The coated elongate member 207 is then cooled and removed from the mandrel 213 thereby forming the reinforced section 205 of the cannula 201. Referring to FIG. 68, the resulting reinforced section 205 is shown. The coating 209 on the elongate member 207 fuses together so that the coating 209 forms a matrix which is reinforced by the elongate member 207. Although it is preferred to heat the coated elongate member 207 to fuse the material together, the coated elongate member may also be coated with a solvent before winding the coated elongate member around the mandrel. The solvent would fuse the adjacent material together and would flash off leaving the fused material.

Referring again to the cross-section of FIG. 66, the reinforced section 205 has a lumen 215 therethrough for delivering or withdrawing fluids from a patient. The reinforced section 205 is attached to the body 203 by any method and is preferably bonded to the body 203 by insert molding. The body 203 includes a lumen 217 which is fluidly coupled to the lumen 215 of the reinforced section 205. The body 203 has been simplified and may include valves, a Y-connection, luer connections or any other features disclosed herein. Furthermore, the body 203 is preferably configured to engage a ⅜ inch fitting which is a standard size for cardiopulmonary bypass systems. The lumen 215 of the reinforced section 205 may be any size but preferably has an internal diameter of at least 0.180 and more preferably at least 0.236 and most preferably at least 0.242 but no more than 0.375 inch.

A distal end 219 of the cannula 201 has an atraumatic tip 221 for introduction into the patient. The atraumatic tip 221 is preferably an integral extension of the coating 209 (see FIG. 68) extending beyond the reinforced section 205. The atraumatic tip 221 has a length of at least 0.100 and a thickness which is preferably the same as the reinforced section.

A proximal end 223 of the reinforced section 205 is flared outward slightly so that the proximal end 223 has a larger lumen than the distal end 219. The proximal end 223 preferably forms an angle of between 2° and 10° and more preferably between 4° and 6° with respect to a longitudinal axis of the cannula 201.

The cannula 201 is particularly useful for arterial return and venous drainage cannulas for the cardiopulmonary bypass system described above since the cannula 201 can be manufactured with a thin wall. As such, the reinforced section 205 preferably has a thickness between 0.010 and 0.025 inch and more preferably between 0.013 and 0.020 inch and most preferably between 0.014 and 0.017 inch. The preferred thickness maintains cannula strength while minimizing the wall size so that flow rates through the cannula are maximized. The cannula 201 of the present invention also has a unique spacing between adjacent portions of the coated elongate member. Referring to FIG. 68, a gap K between adjacent portions of the elongate member 207 is preferably less than 0.019 inch and more preferably less than 0.006 inch and most preferably less than 0.004 inch. A centerline spacing L between adjacent portions of the elongate member 207 is preferably less than 0.022 inch and more preferably less than 0.018 inch and most preferably less than 0.014 inch.

Figure 69:
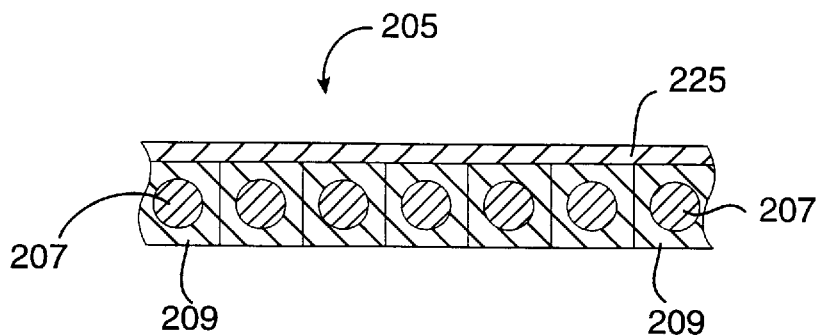
FIG. 69 is a cross-sectional view of a second construction for the reinforced section.

Referring to FIG. 69, a second preferred construction is shown for the reinforced section 205. The elongate member 207 and coating 209 are preferably the same as described above in connection with FIGS. 67–68, however, another layer 225 is positioned either over the elongate member 207 or below the elongate member 207 to increase the strength of the reinforced section 205. When the layer 225 is on the radially inner wall of the cannula 201, the layer 225 may be applied by dipping the mandrel 213 in a suitable solution, extruding the layer over the mandrel 213 or positioning a tube over the mandrel 213. The coated elongate member 207 is then wrapped around the mandrel 213 and heated to fuse the coating 209 and layer 225 together. When the layer 225 is on the radially outer wall of the cannula, the layer 225 may be applied by dipping the coated elongate member 207 in a suitable solution after wrapping the coated elongate member 207 around the mandrel 213, extruding the layer 225 over the coated elongate member 207 wound around the mandrel 213, or positioning a tube over the coated elongate member wound around the mandrel 213 and fusing it to the coated elongate member. The coated elongate member 207 and coating 209 have the same preferred dimensions described above. The layer 225 has thickness of no more than 0.007 inch and more preferably between 0.001 and 0.003 inch and is preferably made of the same materials as the coating 209 described above. FIG. 69 depicts the reinforced section 205 before heating, however, after heating the polymer layer 225 and coating 209 fuse together to form an integrated structure.

Figure 70:
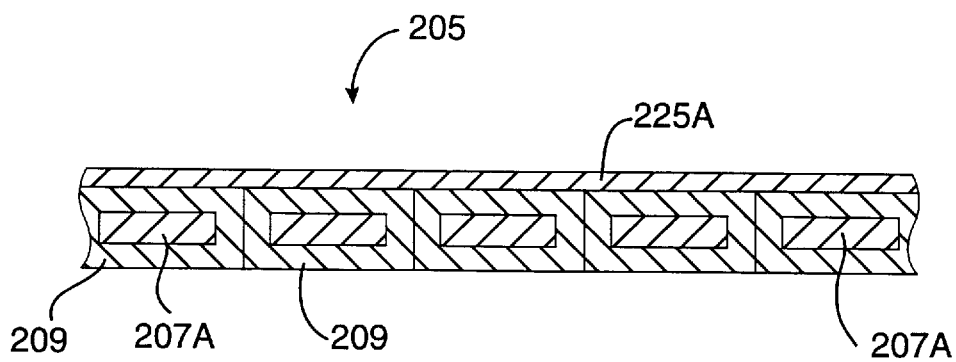
FIG. 70 is a cross-sectional view of a third construction for the reinforced section.

Referring to FIG. 70, a third preferred construction for the reinforced section 205 is shown. The reinforced section 205 is made according to the same procedure described above except that a different elongate member 207A is used. The elongate member 207A is preferably made of metal and has a quadrangle shaped cross-section. A preferred elongate member is a stainless steel flat wire having cross-sectional dimensions of 0.005 inch by 0.020 inch. The elongate member 207A is preferably coextruded with the coating 209 to a thickness of 0.003 all around although any thickness may be used. A layer 225A, which is preferably the same as the layer 225 described above, may be positioned on the radially inner or outer wall of the cannula. The resulting structure yields an inner diameter of at least 0.180 inch, more preferably at least 0.236 inch, and most preferably at least 0.242 inch and no more than 0.375 inch. The resulting reinforced section 205 has a thickness of 0.011 inch without the layer 225A and 0.013 inch with the layer 225A. The reinforced section 205 may also be formed without the layer 225A so that the wall thickness of the cannula is minimized. FIG. 70 depicts the reinforced section 205 before heating, however, after heating the layer 225A and coating 209 fuse together to form an integrated structure.

Figure 71:
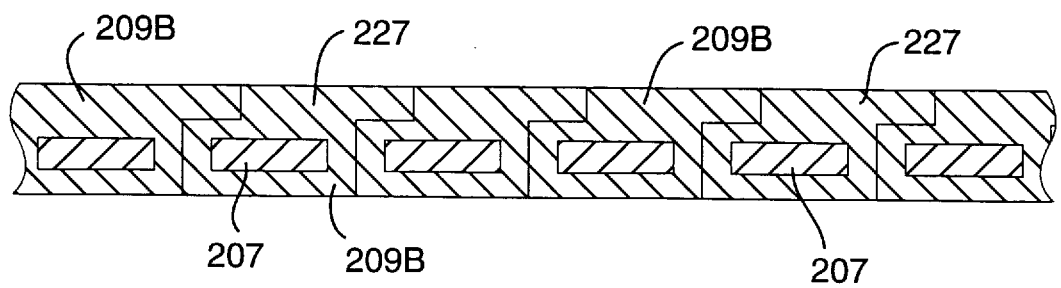
FIG. 71 is a cross-sectional view of a fourth construction for the reinforced section.

Referring to FIGS. 71, a fourth preferred construction for the reinforced section 205 is shown. The reinforced section 205 is made according to the same procedure described above and has the same elongate member 207 as described in connection with FIG. 70. The coating 209B has an overlapping portion 227 which lies over an adjacent portion of the coated elongate member 207B. The elongate member 207B is a 0.005 inch by 0.020 inch stainless steel flat wire, and the coating has a width of 0.003 inch all around the elongate member 207. The overlapping portion 227 has a thickness of 0.005 inch and a length of 0.013 inch. The overlapping portion 227 provides an interlocking relationship between adjacent portions of the coated elongate member 207. FIG. 71 depicts the reinforced section 205 before heating, however, after heating the material from adjacent portions of the coating 209 and the overlapping portion 227 fuse together to form an integrated structure.

Figure 72:
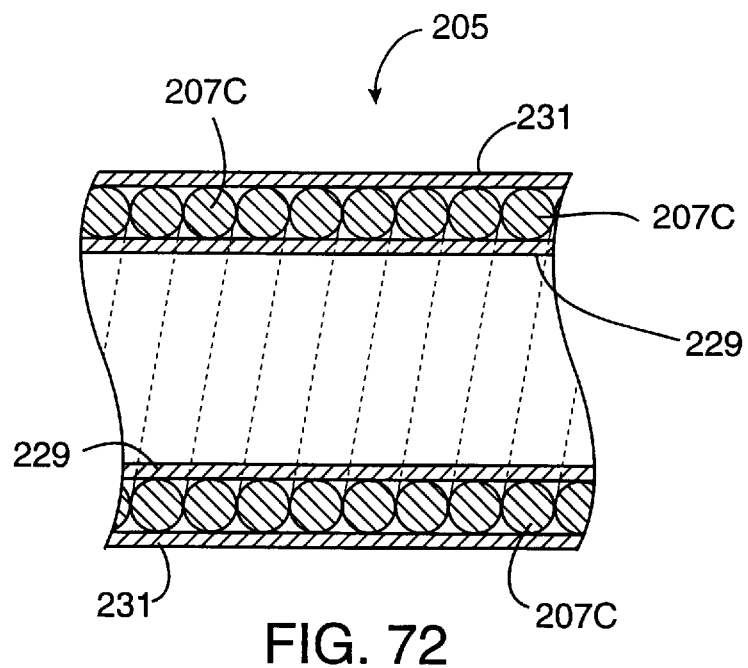
FIG. 72 is a cross-sectional view of a fifth construction for the reinforced section.

Referring to FIG. 72, a fifth preferred construction for the reinforced section 205 is shown. The fifth preferred construction differs from the first through fourth preferred constructions in that the elongate member 207C is not coated before being wrapped around the mandrel. As discussed above, a known method of manufacturing reinforced tubing is to extrude a tube, mount the tube on a mandrel, wind a metal coil around the tube and position another tube over the coil. The tubes and coil are then heated so that the inner and outer tubes bond together. A problem with the known method is that relatively thick walled tubes are formed since the layers must be relatively thick to ensure sufficient strength since the wire must be spaced apart.

The elongate member 207C of FIG. 72 is made of a polymer, preferably 75D polyurethane, so that radially inner and outer polymer layers 229, 231 can fuse to the elongate member 207C to form an integrated structure. Thus, the polymer layers 229, 231 do not need to fuse together completely to form an integrated structure which overcomes a problem with prior art methods of forming reinforced cannulas. The polymer layers 229, 231, preferably 80A polyurethane, are positioned on opposite sides of the polymer elongate member 207C. The polymer layers 229, 231 are preferably softer than the polymer used for making the elongate member 207C. The elongate member 207C preferably has a diameter between 0.005–0.020 inch and more preferably between 0.008 and 0.012 inch. The layers 229, 231 preferably have a thickness of 0.002 to 0.015 inch and more preferably 0.005 to 0.10 inch. The elongate member 207C is preferably wound so that adjacent portions of the elongate member 207C contact one another, however, the polymer elongate member 207C may be wound so that a space exists between adjacent portions of the elongate member 207C. Furthermore, although the elongate member 207C preferably has a circular cross-sectional shape the elongate member 207C may have any other shape. The polymer layers 229, 231 may be applied in any manner including coextrusion, dipping or by simply using preformed tubes.

The polymer layers 229, 231 are preferably heated so that they bond with the elongate member 207C. The polymer layers 229, 231 are preferably positioned on both sides of the elongate member 207C before heating the layers 229, 231, however, the layers 229, 231 may also be applied one at a time. By constructing the reinforced section 205 in this manner, the polymer does not need to flow completely between each part of the elongate member 207C to provide an integrated structure since the layers 229, 231 must simply bond to the elongate member 207C rather than having to bond with the opposing layer 229, 231. FIG. 72 depicts the reinforced section 205 before heating, however, after heating the polymer material from the layer 225A and coating 209 fuse together to form an integrated structure.

Figure 73:
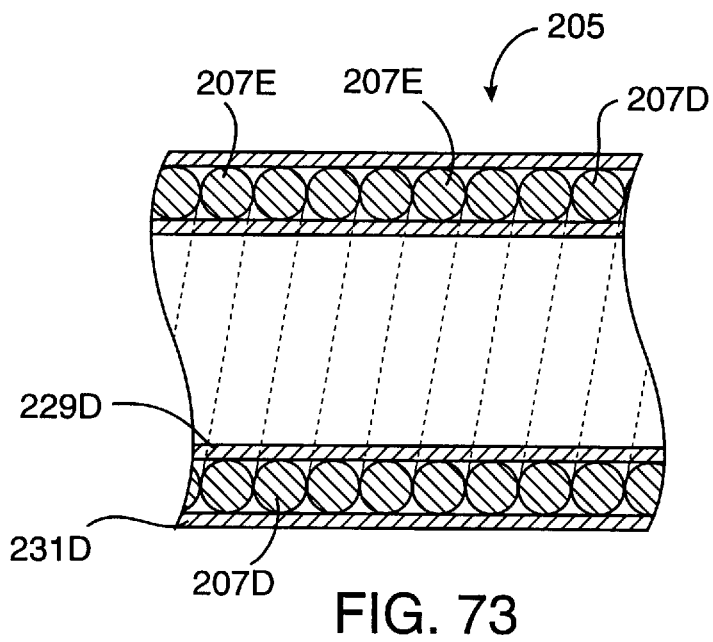
FIG. 73 is a cross-sectional view of a sixth construction for the reinforced section.

Referring to FIG. 73, a sixth preferred construction for the reinforced section 205 is shown with polymer and metal elongate members 207D, 207E wound together. Two polymer layers 229D, 231D are positioned on opposite sides of the elongate members 207D, 207E and may be provided in any manner described above. The polymer layers 229D, 231D are preferably softer than the polymer elongate member 207D. A preferred material for the polymer layers 229D, 231D is 75D polyurethane and a preferred material for the polymer elongate member 207D is 80A polyurethane. The soft polymer layers 229D, 231D are melted to bond to the polymer elongate member 207D thereby forming an integrated structure. The metal elongate member 207E provides structural strength and is preferably a stainless steel wire although any metal may be used. Although it is preferred that the elongate members 207D, 207E have circular cross-sectional shapes, the elongate members may have any other shape. Furthermore, although it is preferred that the elongate members have the same cross-sectional shape, the elongate members may also have different cross-sectional shapes. FIG. 73 depicts the reinforced section 205 before heating, however, after heating the material from the layers 229D, 231D and the elongate member 207D will fuse together to form an integrated structure.

Figure 74:
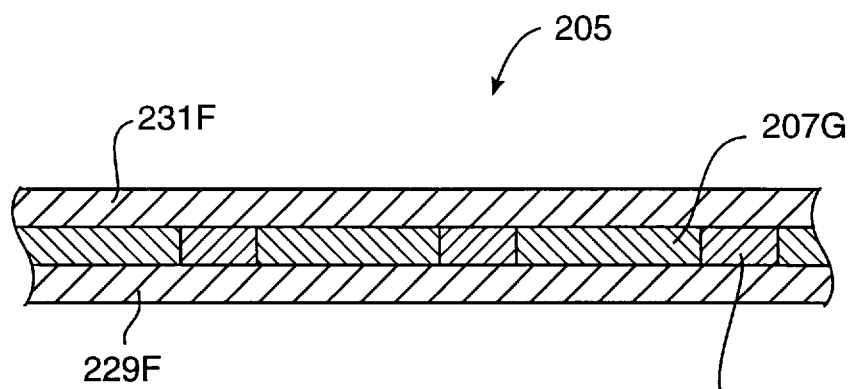
FIG. 74 is a cross-sectional view of a seventh construction for the reinforced section.

Referring to FIG. 74, a seventh preferred construction for the reinforced section 205 is shown. A polymer elongate member 207F is wound together with a flat elongate member 207G. The polymer material for the polymer elongate member 207F may be any polymer and is preferably 75D polyurethane. The flat elongate member 207G is preferably the same as the elongate member 207A described above in connection with FIG. 70. Two layers of polymer 229F, 231F encase the polymer and flat wire elongate members 207F, 207G. The polymer layers 229F, 231F are preferably softer than the polymer material of the elongate member 207F. The polymer layers 229F, 231F are preferably 80A polyurethane, however, any polymer may be used. The polymer layers 229F, 231F may be applied in any manner described above. The polymer layers 229F, 231F preferably have a thickness between 0.002 and 0.010 inch and more preferably between 0.004 and 0.008 inch. The polymer layers 229F, 231F are heated to bond to the polymer elongate member 207. FIG. 73 depicts the reinforced section 205 before heating, however, after heating the layers 229F, 231F and elongate member 207F fuse together to form an integrated structure.

Figure 75:
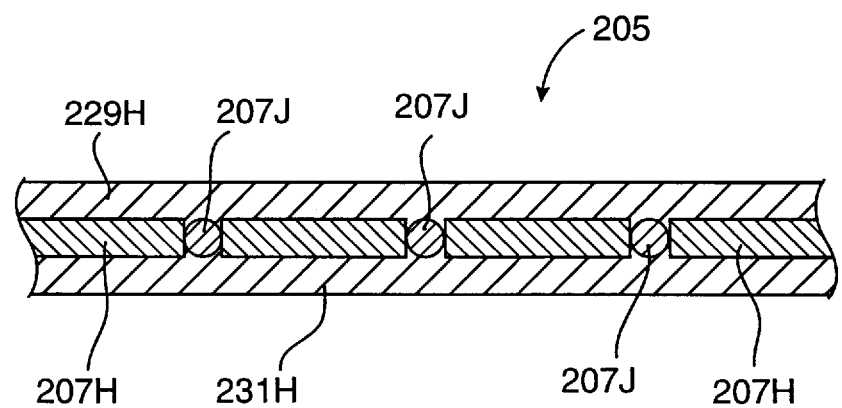
FIG. 75 is a cross-sectional view of a eighth construction for the reinforced section.

Referring to FIG. 75, an eighth preferred construction for the reinforced section 205 is shown. A first elongate member 207H is preferably the same as the elongate member 207A described above in connection with FIG. 70. A second elongate member 207J is made of a polymer and has a thickness between 0.003 and 0.008 inch and more preferably 0.005 inch. Two polymer layers 229H, 231H encase the elongate members. The layers 229H, 231H are preferably 80A polyurethane having a thickness between 0.002 and 0.010 inch and more preferably between 0.004 and 0.008 inch. The polymer layers 229H, 231H may be applied in any manner described above. The polymer layers 229H, 231H are heated to bond to the second elongate member 207J.

Figure 76:
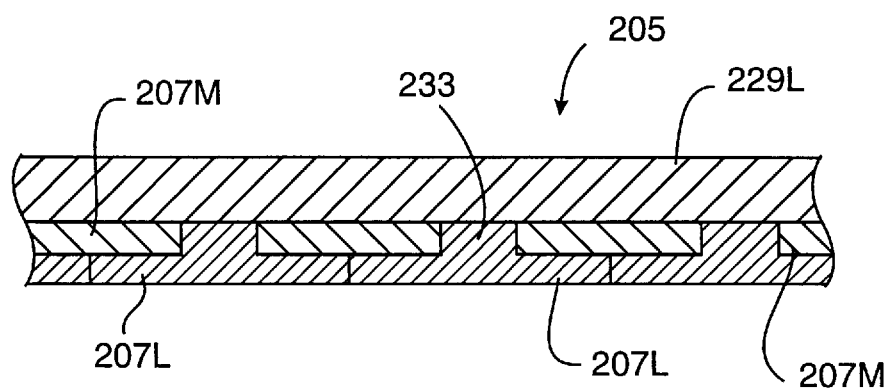
FIG. 76 is a cross-sectional view of a ninth construction for the reinforced section.

Referring to FIG. 76, a ninth preferred construction for the reinforced section 205 is shown. A first elongate member 207L is wound around a mandrel 213 (not shown). The first elongate member 207L is preferably made of polymer, preferably 80A polyurethane, and has a T-shaped cross-sectional shape. The T-shaped cross-sectional shape has a width of 0.028 inch and a height of 0.008 inch. The first elongate member 207L has a radial extension 233 having a width of 0.008 inch. A second elongate member 207M, which is preferably the same as the elongate member 207A described above in connection with FIG. 70, is wound over the first elongate member 207L. A polymer layer 229L is then positioned over the first and second elongate members 207L, 207M and is preferably 80A polyurethane having a thickness of 0.008 inch. The polymer layer 229L may be applied in any manner described above. The polymer layer 229L is then heated so that the polymer layer 229L and the radial extension 233 bond to one another to form an integrated structure.

Figure 77:
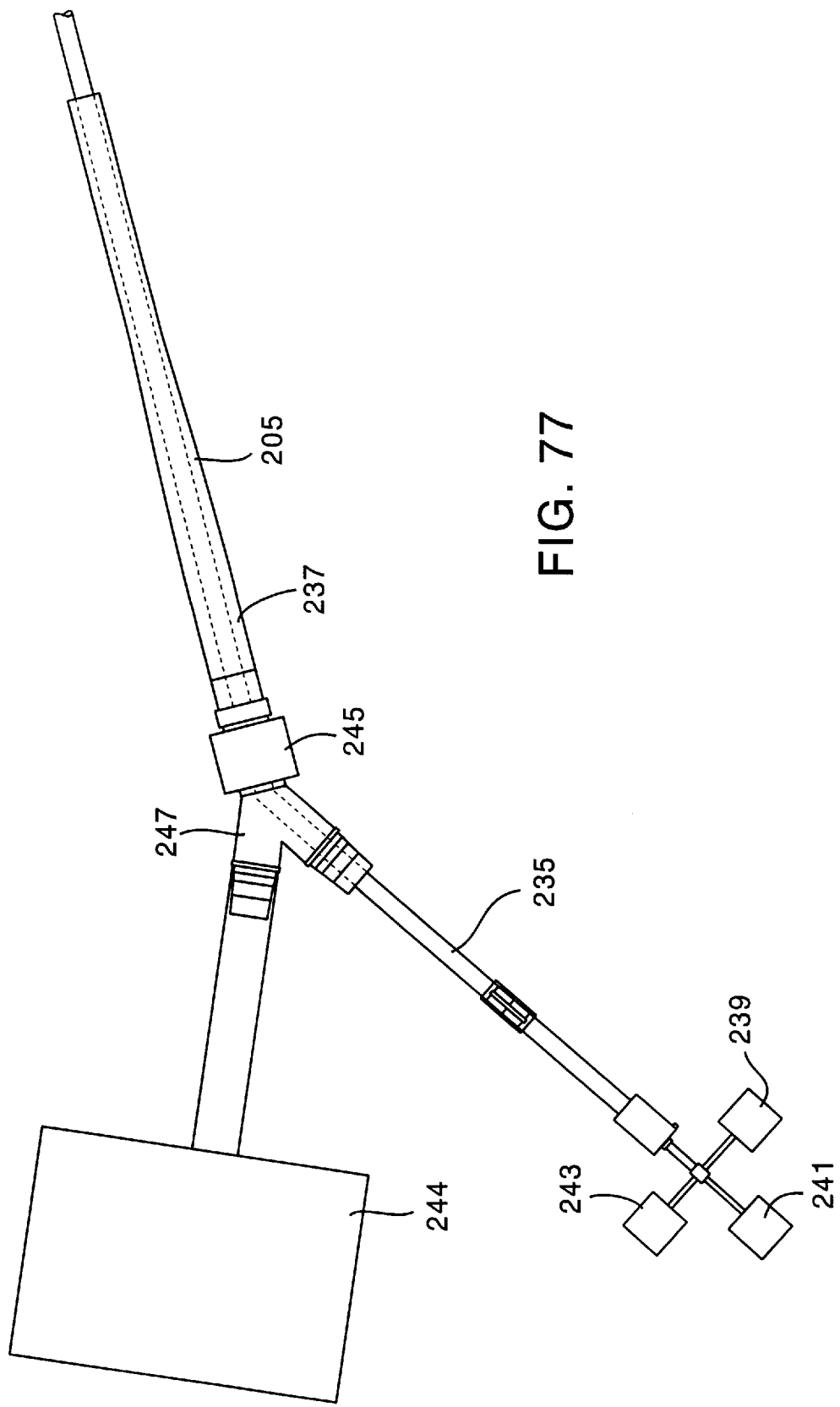
FIG. 77 illustrates an arterial return cannula having a lumen with an aortic occlusion catheter slidably received in the lumen.

Referring to FIG. 77, another aspect of the present invention is shown. An aortic occlusion catheter 235 extends through an arterial return cannula 237. The aortic occlusion catheter 235 and arterial return cannula 237 may be any of the catheters and cannulas described above and the methods described above for arresting a patient's heart and placing the patient on cardiopulmonary bypass are incorporated here. The aortic occlusion catheter 235 is slidably coupled to the arterial return cannula 237 so that the aortic occlusion catheter 235 may be advanced through a patient's artery to the ascending aorta. The aortic occlusion catheter 235 may be any of the catheters described above and is preferably the balloon catheter described above in connection with FIGS. 56 and 57. The aortic occlusion catheter 235 preferably has the three lumen construction of FIG. 54 with the lumens being fluidly coupled to a source of inflation fluid 239, a source of cardioplegic fluid 241 and a pressure sensor 243, respectively. The arterial return cannula 237 is coupled to a source of oxygenated blood 244 from a cardiopulmonary bypass system. The cannula 237 preferably has a reinforced section 205 which is manufactured in the manner described above in connection with FIGS. 66–76.

Figure 78:
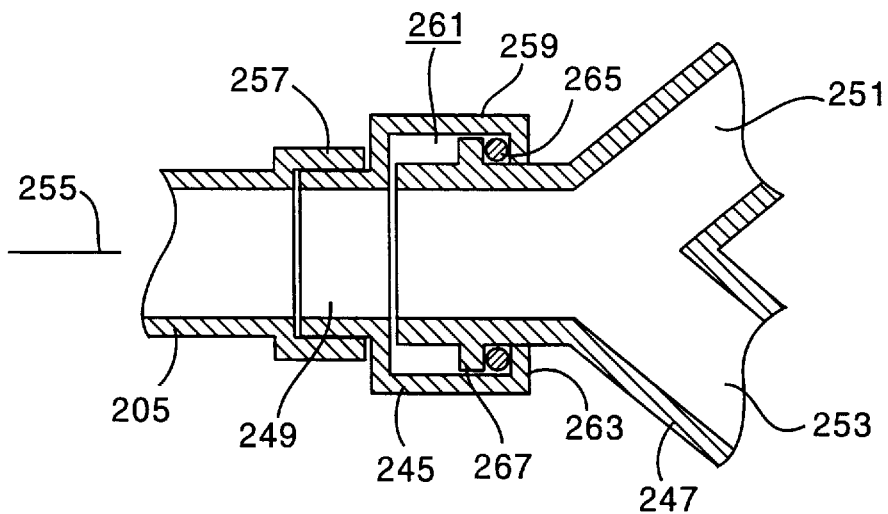
FIG. 78 is partial a cross-sectional view of the arterial return cannula of FIG. 77.
Figure 79:
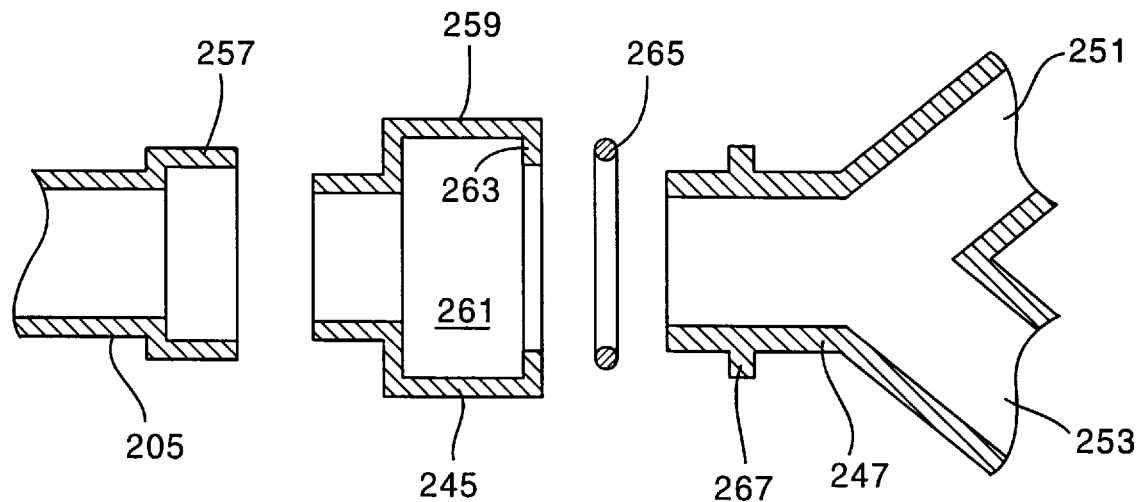
FIG. 79 is an exploded view of FIG. 78.

The arterial return cannula 237 includes a first section 245 and a second section 247. The reinforced section 205 is coupled to the first section 245 in any conventional manner. Referring to FIGS. 78 and 79, partial cross-sectional views of the arterial return cannula 237 are shown with the aortic occlusion catheter 235 removed for clarity. The first section 245 has a first lumen 249 and the second section 247 has second and third lumens 251, 253. The second and third lumens 251, 253 are both fluidly coupled to the first lumen 249. The aortic occlusion catheter 235 extends through the second lumen 251 and into the first lumen 249. The third lumen 253 is coupled to the source of oxygenated blood 244. The oxygenated blood passes in a space between the aortic occlusion catheter 235 and an inner wall of the first lumen 249. The second and third lumens 251, 253 are preferably oriented between 30° and 60° with respect to a longitudinal axis 255 of the first lumen 249 of the arterial return cannula 237. The second and third lumens 251, 253 may, of course, include conventional valves (not shown) or any of the valves described above.

The first section 245 has an enlarged proximal end 257 which receives a coupling 259. The coupling 259 has a chamber 261 and a lip 263 which contacts an o-ring 265. The second section 247 has a flange 267 which is received in the chamber 261 of the coupling 259. The o-ring 265 is compressed between the lip 263 and flange 267 to prevent fluid from leaking between the coupling 259 and second section 247. The flange 267 is preferably snap-fit into the chamber 261. The first section 245 is coupled to the coupling 259 by any conventional method such as solvent bonding.

The first section 245 is rotatable with respect to the second section 247. The rotatable connection between the first and second section 245, 247 helps prevent kinking since the second section 247 can be positioned in any angular orientation. The rotatable connection is particularly important since at least three, and preferably at least four, fluid lines lead to and from the arterial cannula 237 and aortic occlusion catheter 235 together. The rotatable connection between the first and second sections 245, 247 may be accomplished in any other manner without departing from the scope of the invention.

Figure 80:
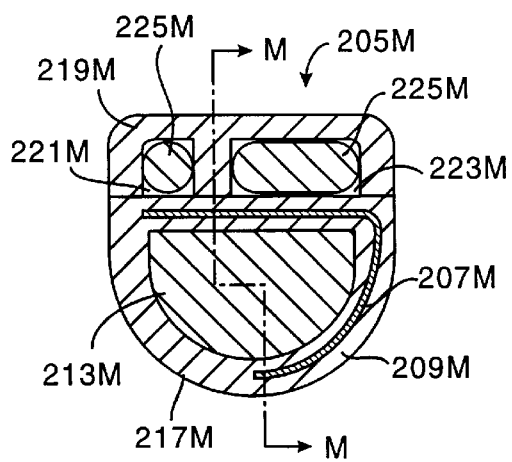
FIG. 80 is a cross-sectional view of a tenth construction for the reinforced section having a coated elongate member wrapped around a mandrel and a member positioned against the coated elongate member.
Figure 81:
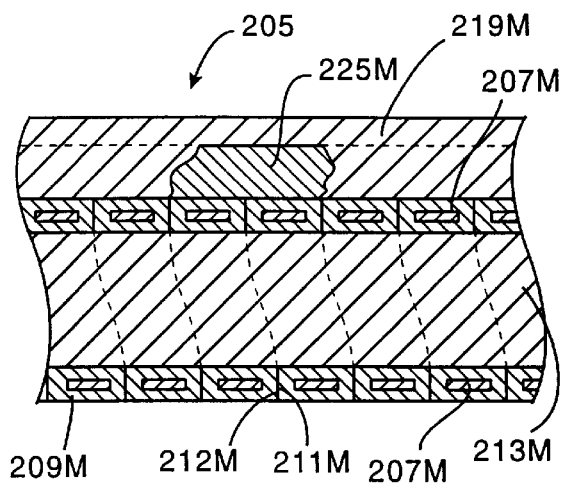
FIG. 81 is a longitudinal cross-sectional view of the tenth construction of FIG. 80 around line M—M.

Referring to FIGS. 80 and 81, a tenth preferred construction for the reinforced section 205 is shown. As discussed herein, the reinforced section 205 may be used for any hollow tube such as a catheter or cannula. As will be discussed below, a specific use for the tenth preferred construction is for an aortic occlusion catheter. Although any of the first through ninth preferred constructions may be used for constructing a multi-lumen tube, the tenth through twelfth constructions described below specifically provide multi-lumen tubes.

An elongate member 207M is coated with a coating 209M. The coating 209M is preferably extruded over the elongate member 207M but may be applied in any other manner such as dipping. The elongate member 207M may be made of any suitable material which has the requisite structural characteristics such as stainless steel, nickel titanium or a polymer. A preferred material is stainless steel ribbon having a width of between 0.006 and 0.012 inch and a height of between 0.002 and 0.004 inch. The elongate member 207M may have any cross-sectional shape, such as circular, and a preferred cross-sectional shape is a quadrangle. Any suitable coating 209M may be used and preferred coatings include polymers and specifically polyurethane, rubber, PVC or any thermoplastic elastomer.

The coating 209M is extruded over the elongate member 207M so that the coating 209M has opposing sides 211M, 212M which are configured to engage one another when the coated elongate member 207M is wrapped around a mandrel 213M. A preferred shape is a quadrangle, however, any other shape may be used including irregular shapes so long as the opposing sides 211M, 212M are configured to engage one another. The coating 209M preferably has a height of 0.006 to 0.014 inch and more preferably 0.008 to 0.012 inch and most preferably 0.008 to 0.010 inch. The coating 209M also has a length of 0.012 to 0.026 inch and more preferably 0.012 to 0.018 inch and most preferably 0.016 to 0.018 inch. The resulting thickness of the reinforced section 205 provides a thin walled tube which resists kinking.

The coated elongate member 207M is then wrapped around the mandrel 213M in a helical manner as described above for other preferred constructions for the reinforced section 205. The coated elongate member 207 is wound so that a first lumen 215M is formed when the mandrel 213M is removed. The first lumen has a D-shaped cross-sectional shape which has an arcuate portion 217M extending around at least 120 (degrees) and more preferably at least 180 (degrees). The arcuate portion 217M is preferably a segment of a circle. The mandrel 213M is preferably coated with a lubricious coating such as TFE to prevent sticking. Although the first lumen 215M is preferably D-shaped, it may take any other shape including circular or oval. Furthermore, although it is preferred to coat the elongate member 207M with the coating 209M and wind the coated elongate member 207N around the mandrel 213M, the coated elongate member 207M may be formed by any other method such as dipping or coextrusion.

A member 219M is positioned on top of coated elongate member 207M after the coated elongate member 207M has been wound around the mandrel 213M. The member 219M is preferably W-shaped so that second and third lumens 221M, 223M are formed when the member 219M is positioned on top of the coated elongate member 207. Blockers 225M, which are preferably made of Teflon, are inserted into the second and third lumens 221M, 223M so that they don't collapse when the reinforced section 205 is heated as will be discussed below. Although it is preferred that the member 219M has two open channels, the member 219M may include two closed channels which form the second and third lumens 221M, 223M without departing from the scope of the invention. An advantage of using the open channel design of the member 219M is that the overall size of the reinforced section 205 is minimized. The member 219M is preferably made of a polymer and a preferred polymer is preferably the same as for coating 209M, however, the member 219M preferably has a higher durometer than the coating 209M so that the coating 209M provides increased bendability while the member 219M provides pushability and kink resistance. The member 219M preferably has a thickness of 0.003 to 0.010 inch and more preferably 0.005 to 0.008 inch.

Figure 82:
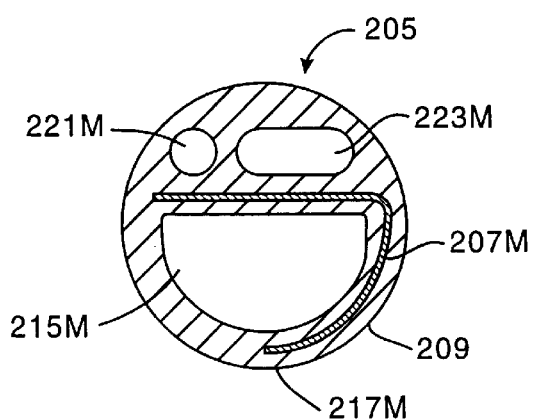
FIG. 82 is a cross-sectional view of the tenth construction after fusing together the member and coated elongate member.

A heat shrink tube (not shown) is then positioned around the coated elongate member 207M and member 219M. The coated elongate member 207M and the member 219M are then heated to melt the coating 209M and member 219M so that they fuse together to form an integrated structure. Referring to FIG. 82, the reinforced section 205 is then cooled and the shrink tube, blockers 225M and mandrel 213M are removed. The resulting reinforced section 205 preferably has a circular cross-sectional shape, however, any other shape may be used. Although it is preferred to heat the coated elongate member 207M and member 219M together, a solvent may also be used to bond the two members 207M, 219M together. The resulting reinforced section 205 preferably has a cross-sectional area of 0.0135 to 0.0154 inch (squared) and more preferably 0.0135 to 0.0145 inch (squared) which corresponds to an outer diameter of 0.131 to 0.140 inch and more preferably 0.131 to 0.136 inch. The resulting reinforced section 205 minimizes the size of the catheter while providing sufficient structural characteristics to prevent kinking when the catheter extends around the aortic arch. As will be described below, the first, second and third lumens 215M, 221M, 223M preferably have the preferred size ranges described herein in connection with aortic occlusion catheters. Further preferred sizes for the first lumen 215M are 0.00754 to 0.01053 inch(squared) and more preferably 0.00817 to 0.01053 inch(squared). Further preferred sizes for the third lumen 223M are 0.00095 to 0.0015 inch(squared) and more preferably 0.0010 to 0.0012 inch (squared).

Figure 83:
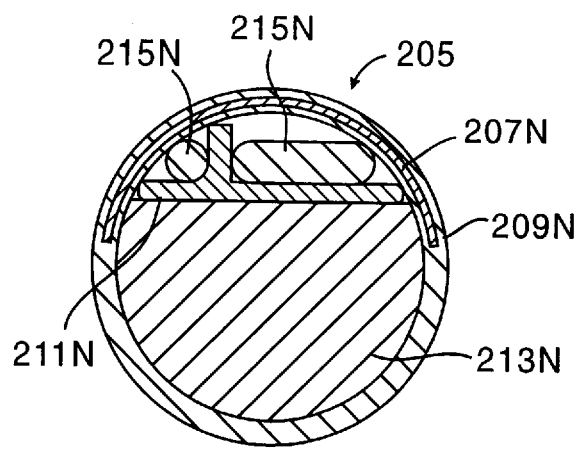
FIG. 83 is a cross-sectional view of an eleventh construction for a reinforced section having a member positioned within a coated elongate member.

Referring to FIG. 83, an eleventh construction for the reinforced section 205 is shown. The eleventh construction includes an elongate member 207N coated with a coating 207N. The elongate member 207N and coating 209N may be any of the elongate members and coatings described above and is preferably the same as the elongate member 207M and coating 209M of the tenth preferred construction for the reinforced section 205. A member 211N and blockers 215N are positioned on the member 211N. The coated elongate member 207N is then wrapped around the mandrel 213N, member 211N, and blockers 215N in a helical manner. The coated elongate member 207N preferably has the same cross-sectional shape as the coated elongate member 207M and the coated elongate member 207N is wrapped so that adjacent portions of the coated elongate member 207N engage one another in the manner described above. Although it is preferred to coat the elongate member 207N with the coating 209N and wind the coated elongate member around the mandrel 213N, 211N and blockers 215N, the coated elongate member 207M may be formed by any other method such as dipping or coextrusion.

Figure 84:
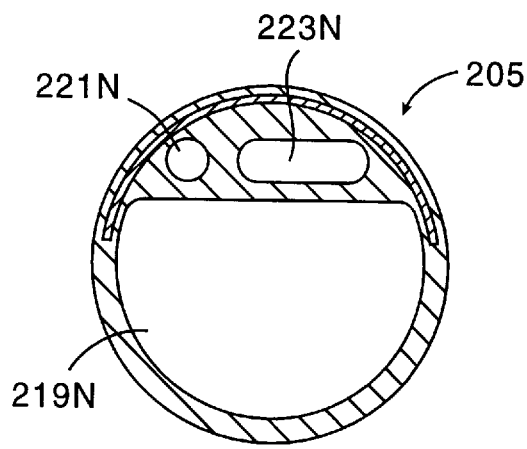
FIG. 84 is a cross-sectional view of the eleventh construction for a reinforced tube after fusing together the member and coated elongate member.

The member 211N is preferably T-shaped but may take any other shape which forms first, second and third lumens 219N, 221N, 223N. The blockers prevent the second and third lumens 221N, 223N from closing when the coated elongate member 207N and member 211N are fused together. A shrink tube (not shown) is positioned around the coated elongate member 207N and the coated elongate member 207N and member 211N are heated to produce the integrated structure of FIG. 84. The eleventh construction preferably has the same dimensions as the tenth construction and the first, second and third lumens 219N, 221N, 223N preferably have the same dimensions as the aortic occlusion catheter described above in connection with any of the aortic occlusion catheters described herein.

Figure 85:
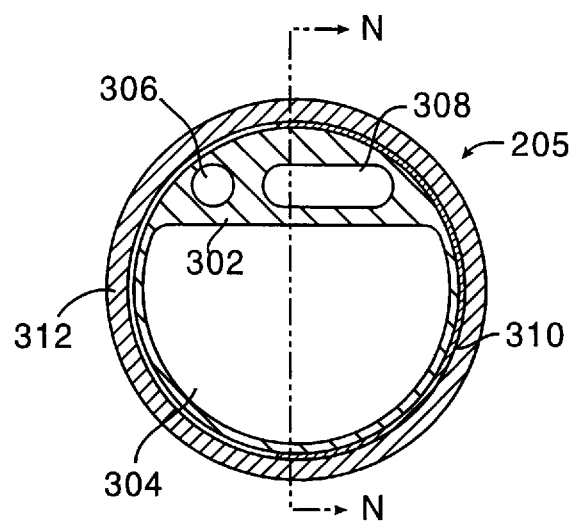
FIG. 85 is a cross-sectional view of a twelfth construction for the reinforced section.
Figure 86:
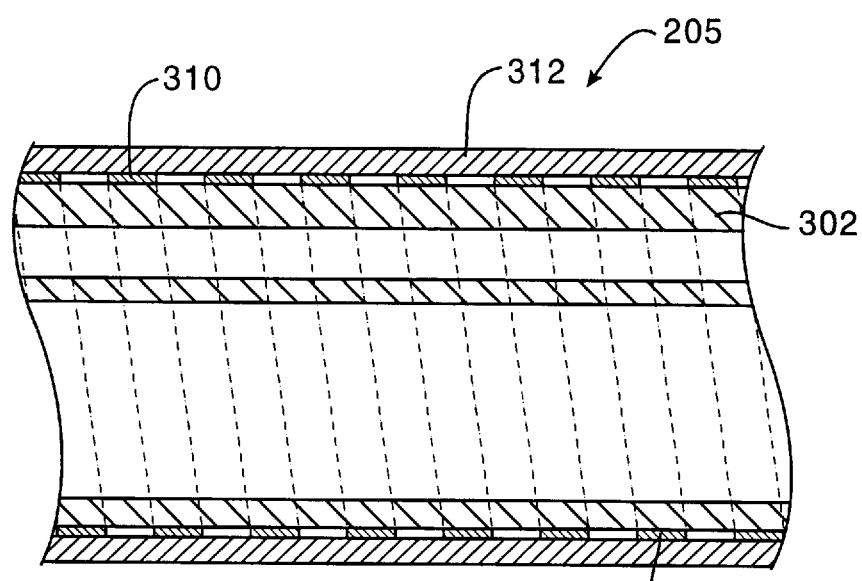
FIG. 86 is a longitudinal cross-sectional view of the twelfth construction of FIG. 85 around line N—N.

Referring to FIG. 85, a twelfth construction for the reinforced section 205 is shown. The twelfth construction includes an extrusion 302 preferably having first, second and third lumens 304, 306, 308 An elongate member 310, which may be any of the elongate members described herein, is wrapped around the extrusion 302. A preferred elongate member 310 is a stainless steel ribbon having a width of 0.003 inch and a height of 0.012 inch. Referring to FIG. 86, the elongate member 310 is preferably wound so that adjacent portions are spaced apart between 0.010 and 0.020 inch. A tube 312, which is preferably made of polyurethane and preferably has a thickness of between 0.002 and 0.006 inch, is positioned over the elongate member 310. A shrink tube (not shown) is then positioned over the tube 312 and blockers are positioned in the lumens 304, 306, 308. The tube 312 and extrusion 302 are then heated so that they bond together and form an integral structure with the elongate member 310. The shrink tube, mandrel and blockers are removed and the resulting structure is essentially the same as the reinforced section 205 of FIG. 84. Although it is preferred to provide the tube 312, the elongate member 310 may also be dipped in a polymer solution to encase the elongate member 310 in polymer.

Figure 87:
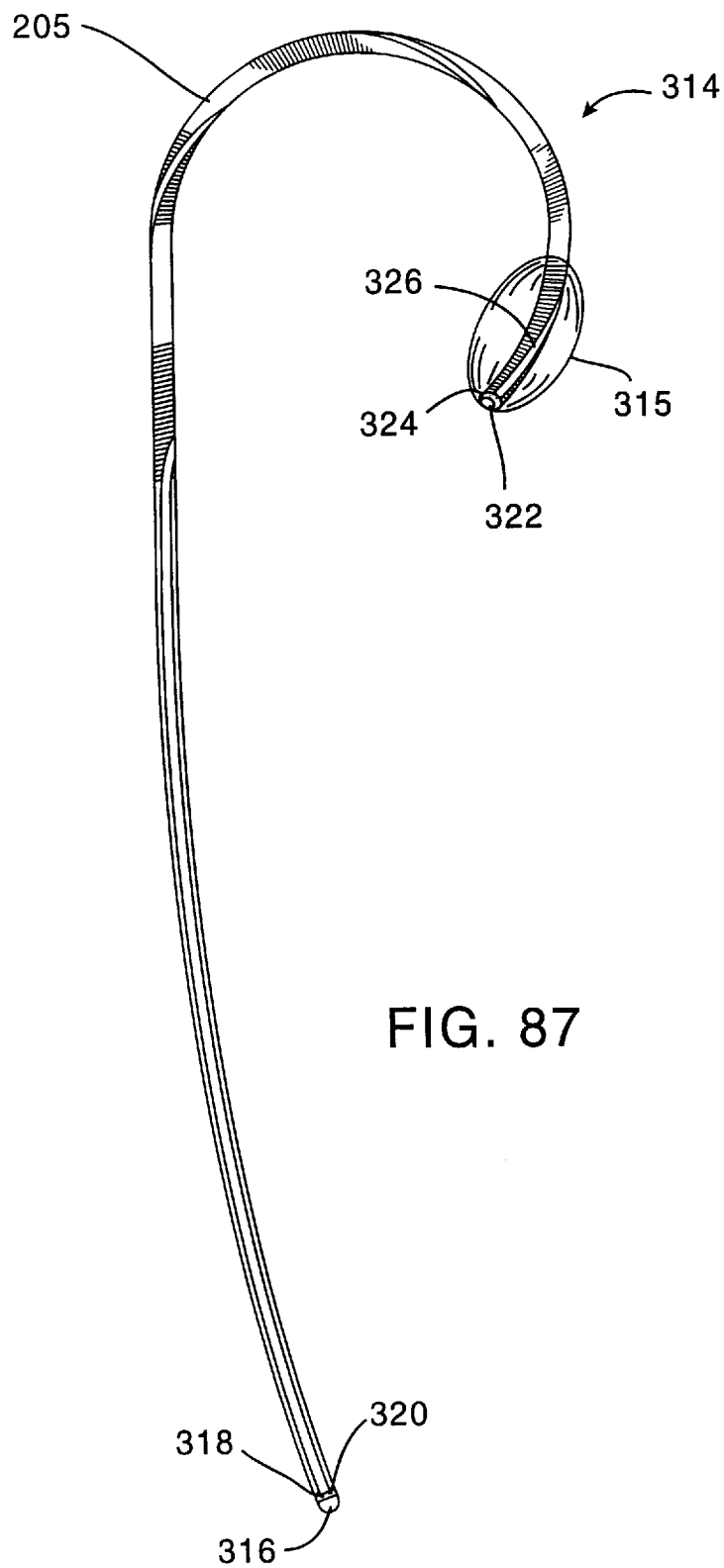
FIG. 87 shows an aortic occlusion catheter having one of the reinforced sections disclosed herein.

Referring to FIG. 87, the reinforced sections 205 described herein, in particular the tenth, eleventh and twelfth reinforced sections of FIGS. 80–86, are useful for reinforcing the distal end of an aortic occlusion catheter 314. The aortic occlusion catheter 314 may take any of the forms described herein and the entire discussion of aortic occlusion catheters herein is incorporated here including, for example, all preferred dimensions, shapes and methods of use. The aortic occlusion catheter 314 includes an occluding member 315, which is preferably an inflatable balloon, at the distal end.

The reinforced section 205 is preferably formed so that first, second and third lumens 316, 318, 320 wind in a helical manner as shown in FIG. 87. By winding the reinforced section 250 in a helical manner the reinforced section 205 does not have any particular axis which is susceptible to kinking. It has been found that when upon winding the coated elongate members around the mandrel and heating the elongate members, the resulting reinforced section twists when cooled so that the reinforced section naturally has the helical shape. Alternatively, the catheter may be twisted after forming or may be twisted during heating if pliable mandrels and blockers are used. Although it is preferred to wind the reinforced section 205 in a helical manner, the reinforced section 205 may also be formed without twisting. The first lumen 316 is used for infusion of cardioplegic fluid and an outlet 322 is provided distal to the occluding member 315 for infusing cardioplegic fluid to a patient's ascending aorta in the manner described above. The second lumen 318 also has an outlet 324 distal to the occluding member 315 which is preferably used for sensing a pressure in the patient's ascending aorta. The third lumen 320 is fluidly coupled to the occluding member 315 through an outlet 326 for inflating the occluding member 315. An advantage of using the tenth reinforced section is that the reinforcing coil does not extend around the inflation lumen 320 so that the reinforcing coil does not have to be penetrated when creating the outlet 326 in the third, inflation lumen 320. The reinforced section 205 extends around the shaped-end of the aortic occlusion catheter 314 which is particularly susceptible to kinking. The shaped-end of the aortic occlusion catheter 314 has the preferred dimensions described above in connection with other preferred aortic occlusion catheters.

The occluding member 315 is preferably mounted to the reinforced section 250. Similar to the aortic occlusion catheter of FIGS. 56 and 57, the occluding member 315 preferably extends beyond the distal tip of the shaft when in the expanded shape (not shown) so that the occluding member acts as a bumper which prevents a distal end 328 from contacting the aorta or the aortic valve. The reinforced section 205 may extend throughout the aortic occlusion catheter 314 but preferably only extends around the portion which passes through the aortic arch. As such, the reinforced section 205 preferably extends 10 inches from a distal end 328 and more preferably 15 inches from the distal end 328.

The methods and devices disclosed herein have been described in conjunction with catheters, however, it is understood that the methods and apparatus may also be used for constructing any other hollow tubes. While the above is a preferred description of the invention, various alternatives, modifications and equivalents may be used without departing from the scope of the invention. For example, the second section 247 of the arterial cannula of FIGS. 78 and 79 may have only one lumen rather than two lumens, the opposing sides of the coated elongate member 207 may have an S-shape, and the reinforced section 205 may have a varying wall thickness. Therefore, the above description should not be taken as limiting the scope of the invention which is defined by the claims.

What is claimed is:

1. A method of forming a multilumen catheter, comprising the steps of:
　forming a first tube having a first lumen and a second lumen, the first lumen having a cross sectional size between 0.00817 to 0.01053 inches$^2$ and the second lumen having a cross sectional size between 0.00095 to 0.0015 inches$^2$;
　wrapping a flexible filament around the first tube in a helical manner;
　positioning a second tube over the flexible filament, the second tube being made of a material, the second tube having a thickness of 0.002 to 0.006 inch; and melting the second tube so that the material contacts and bonds to the first tube thereby forming a body for a multilumen catheter; and mounting an occluding member to the second tube, the occluding member being movable between a collapsed position and an expanded position, the occluding member being configured to occlude a patient's ascending aorta when in the expanded position.

2. The method of claim 1, wherein:

the mounting step is carried out with the occluding member being an inflatable balloon.

3. The method of claim 1, wherein:

the melting, positioning and wrapping steps are carried out so that the first and second lumens wind in a helical manner.

4. The method of claim 1, further comprising the step of:

shaping a distal portion of the body is hook-shaped to position the occluding member in the aortic arch when body extends through a peripheral artery.

* * * * *